United States Patent
Lam et al.

(10) Patent No.: US 10,978,277 B2
(45) Date of Patent: Apr. 13, 2021

(54) APPARATUS AND METHOD FOR HANDLING AN IMPLANT

(71) Applicant: NOVA PLASMA LTD., Megiddo (IL)

(72) Inventors: Amnon Lam, Kibbutz Givat Oz (IL); Aviad Harhol, Tel Aviv (IL); Eliezer Fuchs, Kibbutz Megiddo (IL); Chen Porat, Kiryat Tivon (IL)

(73) Assignee: NOVA PLASMA LTD., Megiddo (IL)

( * ) Notice: Subject to any disclaimer, the term of this patent is extended or adjusted under 35 U.S.C. 154(b) by 498 days.

(21) Appl. No.: 15/572,454

(22) PCT Filed: May 11, 2016

(86) PCT No.: PCT/IL2016/050501
§ 371 (c)(1),
(2) Date: Nov. 7, 2017

(87) PCT Pub. No.: WO2016/181396
PCT Pub. Date: Nov. 17, 2016

(65) Prior Publication Data
US 2018/0138022 A1    May 17, 2018

Related U.S. Application Data

(60) Provisional application No. 62/159,387, filed on May 11, 2015, provisional application No. 62/239,928, (Continued)

(51) Int. Cl.
*A61L 27/18* (2006.01)
*H01J 37/32* (2006.01)
(Continued)

(52) U.S. Cl.
CPC ........ *H01J 37/32798* (2013.01); *A61L 27/18* (2013.01); *A61L 27/50* (2013.01);
(Continued)

(58) Field of Classification Search
None
See application file for complete search history.

(56) References Cited

U.S. PATENT DOCUMENTS

| 3,851,436 A | 12/1974 | Fraser |
| 4,846,101 A | 7/1989 | Montgomery |

(Continued)

FOREIGN PATENT DOCUMENTS

| CN | 101711708 A | 5/2010 |
| JP | 2008-515616 A | 5/2008 |

(Continued)

OTHER PUBLICATIONS

Duske et al., (2012) Atmospheric plasma enhances wettability and cell spreading on dental implant metals. Journal of clinical periodontology, 39(4), 400-407.

(Continued)

*Primary Examiner* — Cachet I Proctor
(74) *Attorney, Agent, or Firm* — Dorsey & Whitney LLP

(57) ABSTRACT

An apparatus for plasma treatment of an implant prior to installing the implant in a live subject is provided. The apparatus comprises an activation device and a portable container detachable from the activation device. The portable container comprises a closed compartment containing the implant immersed in a fluid, and the activation device comprises a slot configured to receive the portable container. The activation device further comprises an electrical circuit configured to be electrically associated with at least one electrode and configured to provide to the at least one electrode electric power suitable for applying a plasma generating electric field in the closed compartment, when the portable container is disposed in the slot. A container (Continued)

suitable for providing plasma treatment to a silicone implant and a method for preparing an implant for implantation surgery are also provided.

20 Claims, 19 Drawing Sheets

Related U.S. Application Data filed on Oct. 11, 2015, provisional application No. 62/300,942, filed on Feb. 29, 2016.

(51) Int. Cl.
*A61L 27/50* (2006.01)
*A61L 27/54* (2006.01)

(52) U.S. Cl.
CPC ............ *A61L 27/54* (2013.01); *H01J 37/321* (2013.01); *H01J 37/32403* (2013.01); *H01J 37/32449* (2013.01); *H01J 37/32568* (2013.01); *H01J 37/32715* (2013.01); *H01J 37/32733* (2013.01); *H01J 37/32825* (2013.01); *A61L 2300/406* (2013.01); *A61L 2400/18* (2013.01); *A61L 2430/04* (2013.01); *H01J 37/32091* (2013.01); *H01J 37/32348* (2013.01)

(56) References Cited

U.S. PATENT DOCUMENTS

| | | | | |
|---|---|---|---|---|
| 4,955,901 | A * | 9/1990 | Nishiguchi | A61F 2/1613 427/2.24 |
| 5,085,086 | A * | 2/1992 | Johnson | G01N 1/2035 73/863.86 |
| 5,188,800 | A * | 2/1993 | Green, Jr. | A61C 8/0012 134/1 |
| 5,558,230 | A | 9/1996 | Fischer | |
| 5,697,997 | A * | 12/1997 | Aronsson | A61F 2/30767 65/32.1 |
| 5,960,956 | A | 10/1999 | Langanki | |
| 6,033,437 | A * | 3/2000 | Perry | A61F 2/141 128/898 |
| 6,702,855 | B1 * | 3/2004 | Steinemann | A61L 27/06 623/23.53 |
| 7,451,870 | B2 | 11/2008 | Donahoe | |
| 8,071,042 | B2 | 12/2011 | Kuhry | |
| 8,190,271 | B2 * | 5/2012 | Overstreet | A61K 9/0046 607/116 |
| 8,518,420 | B2 | 8/2013 | Biris | |
| 2004/0037946 | A1 * | 2/2004 | Morra | A61L 33/0029 427/2.24 |
| 2005/0031689 | A1 * | 2/2005 | Shults | A61B 5/14532 424/473 |
| 2005/0035015 | A1 | 2/2005 | Bressler | |
| 2006/0157453 | A1 * | 7/2006 | Dumont | C08J 7/123 219/121.5 |
| 2006/0251795 | A1 * | 11/2006 | Kobrin | A61L 27/34 427/2.1 |
| 2007/0084144 | A1 | 4/2007 | Labrecque | |
| 2007/0225785 | A1 * | 9/2007 | Park | A61L 27/50 607/116 |
| 2008/0208347 | A1 * | 8/2008 | Muratoglu | A61L 27/52 623/18.11 |
| 2009/0192528 | A1 | 7/2009 | Higgins | |
| 2010/0047532 | A1 * | 2/2010 | Mozetic | C08J 7/12 428/195.1 |
| 2011/0008877 | A1 * | 1/2011 | Skelnik | A01N 1/0263 435/284.1 |
| 2011/0095688 | A1 | 4/2011 | Bisges | |
| 2012/0183437 | A1 | 7/2012 | Keener | |
| 2013/0118406 | A1 * | 5/2013 | Rostaing | A61L 2/14 118/723 MW |
| 2013/0230426 | A1 * | 9/2013 | Popot | A61L 2/14 422/29 |
| 2014/0224687 | A1 | 8/2014 | Schuster | |
| 2014/0377320 | A1 | 12/2014 | Pietramaggiori | |
| 2016/0000062 | A1 | 1/2016 | Chen | |
| 2016/0264274 | A1 | 9/2016 | Kulaga | |
| 2016/0331841 | A1 * | 11/2016 | Prestwich | A61K 9/0019 |
| 2017/0014553 | A1 * | 1/2017 | Antoni | A61L 29/085 |
| 2019/0099259 | A1 * | 4/2019 | Porter | A61K 33/00 |
| 2019/0365527 | A1 * | 12/2019 | Wijay | A61F 2/12 |

FOREIGN PATENT DOCUMENTS

| | | |
|---|---|---|
| WO | 9312821 | 7/1993 |
| WO | 00/14146 A1 | 3/2000 |
| WO | 2007103705 | 9/2007 |
| WO | 2008031596 A1 | 3/2008 |
| WO | 2013056844 | 4/2013 |
| WO | 2015/091104 A1 | 6/2015 |
| WO | 2015083155 | 6/2015 |
| WO | 2015087326 | 6/2015 |

OTHER PUBLICATIONS

Heinlin et al., (2010) Plasma medicine: possible applications in dermatology. JDDG: Journal der Deutschen Dermatologischen Gesellschaft, 8(12), 968-976.

Lee et al., (2011) Improvement of Hydrophilicity of Interconnected Porous Hydroxyapatite by Dielectric Barrier Discharge Plasma Treatment. IEEE Transactions on Plasma Science, 39(11), 2166-2167.

Moriguchi et al., (2012) Plasma Surface Modification of Artificial Bones for Bone Regeneration. Orléans-France, 48.

* cited by examiner

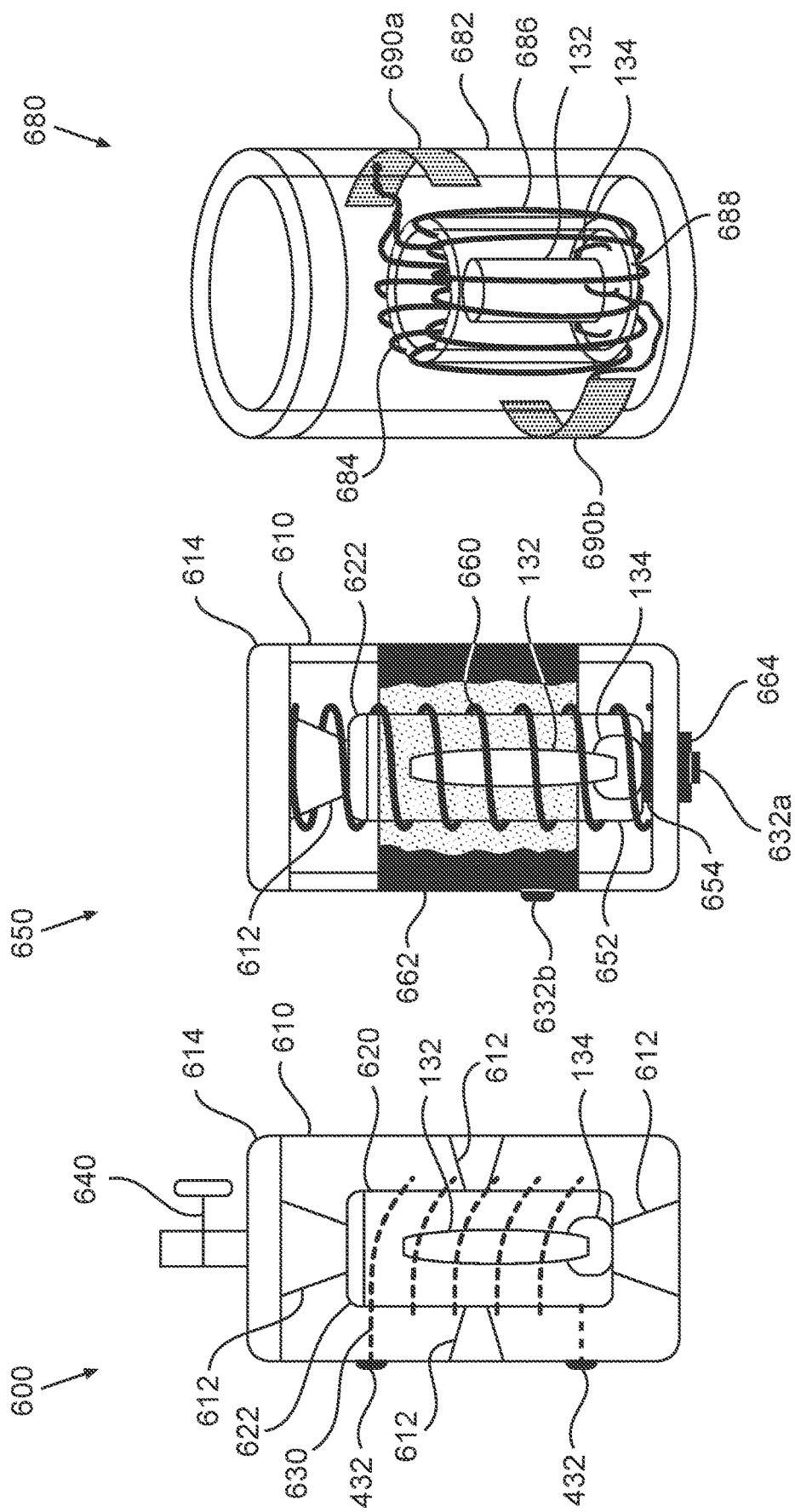

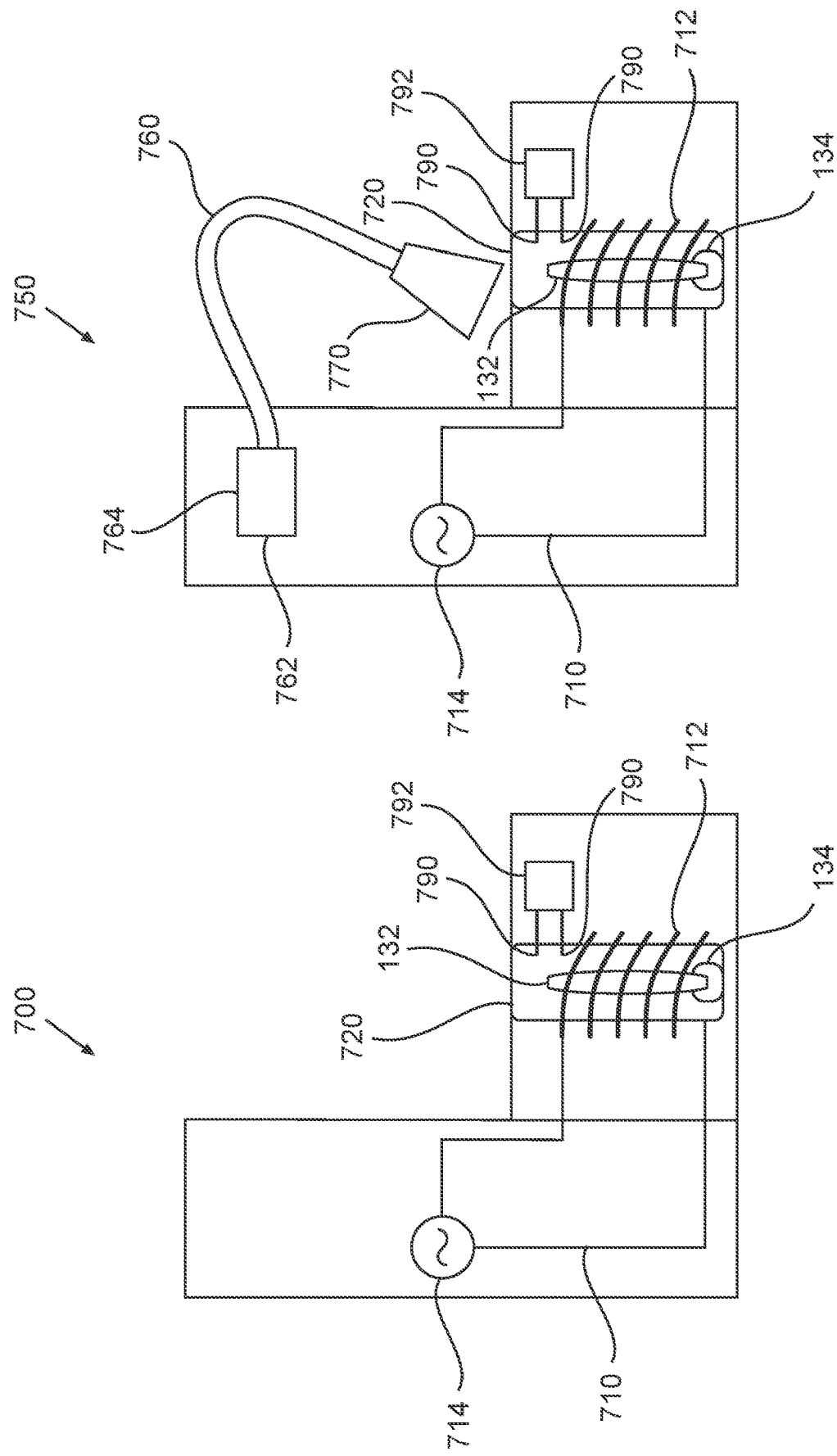

APPARATUS AND METHOD FOR HANDLING AN IMPLANT

FIELD OF THE INVENTION

The invention, in some embodiments, relates to the field of treating and handling an implant prior to using the implant in a body of a live subject and to related devices, apparatuses and methods.

BACKGROUND OF THE INVENTION

Plasma is known to affect surfaces of objects that are exposed to the plasma. Generally, plasma refers herein to ionized gas, including positively charged ions and negatively charged electrons, wherein the whole volume of the ionized gas is roughly neutral. Positively charged ions are generally referred to herein simply as "ions", negatively charged electrons are referred to as "electrons", and neutral atoms and molecules are referred to as "neutrals".

Surfaces of objects exposed to plasma may often be affected so that some characteristics of the surface change following such exposure. It is believed that surface energy and chemistry may change due to the generation of reactive species in the plasma, and possibly due to deposition of chemical substances on the surface. A featured result may be a modification of the surface properties. For example, plasma generated in a gaseous atmosphere comprising argon or helium possibly with an admixture of oxygen, or in air at low pressure or at atmospheric pressure, may render a surface of an object more hydrophilic.

SUMMARY OF THE INVENTION

Aspects of the invention, in some embodiments thereof, relate to treating and handling an implant prior to using the implant in a body of a live subject. More specifically, aspects of the invention relate to devices, apparatuses and methods for plasma-treating an implant in a clinic or in a medical care center prior to installing the implant. According to some aspects of the invention, the implant is a silicone implant, for example a silicone breast implant.

If an object intended to be installed in a body of a live subject is exposed to plasma under certain conditions, biocompatibility of the object tends to improve. Such biocompatibility, associated with surface properties of the object, may include higher wettability, more suitable topography and improved drug delivery. For example, following suitable plasma treatment of an implant, hydrophilic properties of the surface of the implant tend to improve. Hydrophilic properties substantially enhance the wettability of the surface and improve the initial attachment of blood platelets to the treated implant. Consequently, better healing process may be achieved with substances that have been exposed to plasma prior to use.

The term "implant" is used herein for any object or substance which is to be installed in a body of a live subject in a medical procedure of implantation or installing or grafting, particularly such that is not autologous. Thus, "implant" may include an artificial implant such as an implant made of metal, e.g. a dental implant or an abutment for a dental implant; or an implant made of polymer material such as silicone; or made of ceramic; or any combination thereof, for example an artificial joint or, generally, an implant having metallic and ceramic parts. "Implant" may also include biomaterial, where biomaterial is referred to herein as a substance which is configured to direct a diagnostic or therapeutic process in a body of a live subject, by controlling interactions with components of living system in the body. Examples of biomaterial may include bone graft used during a bone grafting procedure, e.g. prior to installing a dental implant; polymers, and textile-based polymers in particular; hernia mesh, used in a hernia repair procedure; or collagen membrane used in dental surgery procedures.

Better healing process and faster and enriched osseointegration may be achieved with implants, bone graft or other biomaterial that have been exposed to plasma prior to installing ("osseointegration" herein means the direct structural and functional connection between a live bone and an artificial implant or bone graft or other biomaterial installed or used therewith). For example, Atmospheric plasma enhances wettability and cell spreading on dental implant metals (J Clin Periodontol 2012; 39: 400-407) by Duske et. al. describes significant reduction of contact angle of titanium discs (baseline values: 68°-117°) to close to 0°, irrespective of surface topography, after the application of argon plasma with 1.0% oxygen admixture for 60 s or 120 s. The cell size of osteoblastic cells grown on argon-oxygen-plasma-treated titanium discs was significantly larger than on non-treated surfaces irrespective of surface topography. As another example, D.-S. Lee et al. in Improvement of Hydrophilicity of Interconnected Porous Hydroxyapatite by Dielectric Barrier Discharge Plasma Treatment (IEEE Trans. Plasma Sci. 39 (11) 2166 (2011)) show that a dielectric barrier discharge (DBD) plasma treatment promotes hydrophilicity of interconnected porous calcium hydroxyapatite (IP-CHA) surfaces. Further, in Plasma Surface Modification of Artificial Bones for Bone Regeneration (published in ICPM 5, May 18-24, 2014, Nara, Japan), Moriguchil et. al. show that plasma-treatment can improve bone healing by IP-CHA, enhancing hydrophilicity of IP-CHA and its osteogenic potential in vitro. As yet another example, plasma surface treatment often improves biocompatibility of polystyrene cell culture surfaces, affecting adhesion and proliferation of cells cultures on such surfaces. For example, plasma surface modification of cell-culture materials may assist in establishing a stable culturing process for cells obtained from a patient's own body, for a later regeneration medicine process with the patient.

Notwithstanding the beneficial effects of plasma treatment discussed above, such beneficial effects of exposure to plasma on implant surfaces are often temporary, and demonstrated improved or enhanced healing decreases as the time interval between exposure of the implant to plasma and installing the implant in a body, increases. Such temporal deterioration often renders an activation of an implant by exposing the implant to plasma at the implant's manufacturing site useless, because it may not be possible to ensure using the implant within a short period of time after the exposure to plasma, so as to maintain the benefits of such exposure. It would therefore be advantageous to provide for plasma treating an implant in a medical care center, soon before a medical procedure for installing the implant is carried out.

Characteristics of the electric field that could generate plasma in a fluid, may depend strongly on characteristics of the fluid itself, in addition to the geometry involved (such as shape and configuration of electrodes used for the application of the electric filed, distance between the electrodes etc.). Generally, if the fluid is a gas, the higher the pressure of the gas, the higher the electric field should be to ignite plasma. Also, some gases ignite at lower fields than others. For example, helium gas at atmospheric pressure ignites at an RF field (in a frequency between 1 MHz and 15 MHz) of about 7 KV over a distance of 1 cm between (plate) electrodes, and at a voltage of about 200V in 0.8 KPa with the same electrodes configuration. With a similar configuration of electrodes and at similar field frequencies, air ignites at a voltage of about 20 KV in atmospheric pressure and at a voltage of about 800V in 0.8 KPa.

According to some techniques, a closed compartment containing an implant may thus be filled at the implant's manufacturing site or at a packaging site with an ionizable fluid, wherein the fluid is adapted for plasma ignition at a later time in a clinic. An ionizable fluid stands for a fluid capable of being excited to plasma upon the application of a suitable electromagnetic field. However, maintaining an ionizable fluid in the closed compartment for storing periods that might last for months or even years, and such that following the storing period the fluid in the closed compartment will ignite easily (that is to say, at a relatively low electric field)—may involve considerable technical difficulties. For instance, very good sealing should be ensured to the closed compartment, so that gas at a low pressure—and possibly at a different composition from that of air—is maintained within the closed compartment. If the sealing is compromised—for example, if, over time, the pressure rises or the composition of the fluid changes inside the closed compartment—plasma generation may not be possible any more with the same electric field characteristics sufficient for plasma generation, had the atmosphere in the closed compartment been steady. It would therefore be advantageous to provide for plasma treating of an implant in a clinic or a medical care center wherein the implant is inside a portable container, possibly the same container in which the implant was transported or shipped to the clinic. The portable container is configured to allow plasma generation there inside, without necessarily being sealed and without necessarily being configured to maintain the implant in low-pressure atmosphere during long periods of storage.

There is thus provided according to an aspect of the invention an apparatus for plasma treatment of an implant prior to installing the implant in a live subject. The apparatus comprises an activation device and a portable container which is detachable from the activation device. The portable container comprises a closed compartment containing the implant, and further comprising a fluid—a liquid or gas—in which the implant is immersed. According to some embodiments, the portable container is used for storing the implant after manufacturing and for shipping the implant from the manufacturing site or a packaging site to the clinic where the implant is to be installed in the subject. The activation device comprises an electrical circuit and a slot configured to receive the portable container. According to some embodiments, the activation device may be used in the clinic where an installment of the implant is intended to be performed, just prior to such installment. The portable container with the implant inside may be positioned in the slot and the electrical circuit may be activated to generate plasma within the closed compartment, in the vicinity of the implant and around it. The electrical circuit is configured to electrically associate with at least one electrode and to provide to the electrode(s) electric power suitable for applying a plasma-generating electric field in the closed compartment. According to some embodiments the electrode may be a part of the activation device, and according to some embodiments the electrode may be part of the portable container, whereas the electrical circuit electrically associates with the electrode as the portable container is placed in the slot. Thus, upon activation of the electric circuit, plasma may be generated within the closed compartment in a space adjoining portions of the implant which are to be plasma-treated.

According to some embodiments the fluid in the closed compartment is maintained at ambient pressure and may even change slightly in the course of time as ambient conditions around the portable container vary. According to some embodiments the closed compartment may contain gas, in which the implant is immersed. According to some embodiments, the closed compartment, although closed, is not sealed, and the gas may penetrate into or out from the closed compartment. According to some embodiments, the closed compartment—when not positioned in the slot of the activation device—contains gas at ambient pressure and composition. According to some embodiments the closed compartment is microbially sealed. Being "microbially sealed" herein means that microbial organisms may not penetrate into the microbially sealed closed compartment, wherein microbial organisms may include any form of viruses, prokaryotic cells or eukaryotic cells, including fungi and bacteria. In some embodiments the closed compartment is microbially sealed using a suitable filter that allows passage of fluid molecules therethrough (e.g. gaseous molecules) but prevents passage of microbial organisms therethrough.

According to some embodiments the apparatus is configured and operable to apply a plasma-generating electric field in the closed compartment at ambient conditions. That is to say that a portable container having a closed compartment containing an implant immersed in air at ambient pressure may be placed in the slot of the activation device, and plasma may be generated thereinside by activating the electric circuit. The electric circuit then applies the plasma-generating electric field and plasma is generated, substantially without any further intervention with the portable container or with the gas inside.

According to some embodiments a fluid transfer system of the activation device is fluidly associated with the portable container when the portable container is placed in the slot, and is used to flush the closed compartment with an ionizable gas or to pump the closed compartment for reducing the pressure therein—thereby facilitating plasma generation (namely enabling plasma generation at a lower voltage compared to plasma generation in air).

There is further provided according to an aspect of the invention a portable container for handling an implant configured to be installed in a live subject. The portable container comprises a closed compartment containing therein the implant, the closed compartment being configured to be opened by a user, thereby enabling removing the implant from the portable container. The portable container further comprises a field transponder configured to transmit a signal, the signal being configured to certify an identity of the portable container or a position thereof relative to a receiver configured to receive the signal. The portable container is further configured to enable plasma excitation of an ionizable fluid near the implant inside the closed compartment when the ionizable fluid is subject to a plasma-generating electric field generated by an activation device detachable from the portable container.

There is further provided according to an aspect of the invention a plasma chamber for plasma treating an implant made of an electrically isolating material prior to implanting the implant in a live subject. The plasma chamber comprises a closable compartment having walls defining an internal space adapted to house the implant therein. The plasma chamber further comprises a spacer projecting from a floor of the compartment and configured to support the implant above the floor while contacting the implant along a surface area smaller than about 5% of a total surface area of the implant. The plasma chamber further comprises at least two electrodes positioned on the walls facing one another across the internal space of the closable compartment. Each electrode has a tip positioned in a hollow cavity depressed in the wall on an internal side thereof. The electrodes are configured to electrically associate with an EM power source to generate a plasma generating EM field inside the closable compartment.

There is further provided according to an aspect of the invention a method for preparing a silicone implant to implanting the implant in a live subject. The method comprises a step of generating plasma in a plasma chamber housing the implant. The method further comprises a step of wetting the implant with a polar liquid comprising at least one therapeutically effective agent after the step of generating plasma. The method further comprises a step of removing the implant from the plasma chamber, after the step of generating plasma, for installing the implant in the live subject. According to some embodiments the wetting is performed prior to the removing of the implant from the plasma chamber. According to some embodiments the removing of the implant from the plasma chamber is performed prior to the wetting.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 5A schematically depicts an embodiment of a portable container of the invention, configured for enabling plasma generation therein, comprising an external capsule and a closed compartment inside the external capsule;

FIG. 5B schematically depicts an embodiment of a portable container of the invention, configured for enabling plasma generation therein, comprising an external capsule, a closed compartment inside the external capsule and a floating electrode disposed between the external capsule and the closed compartment;

FIG. 6 schematically depicts a configuration of an electrode for plasma generation in a portable container according to the teachings herein;

FIG. 7A schematically depicts an embodiment of an activation device configured for plasma treating an implant in a chamber thereof at ambient conditions;

FIG. 7B schematically depicts an embodiment of an activation device different from the activation device of FIG. 7A in having a fluid transfer system for flushing the chamber with gas or pumping gas from around the implant;

DETAILED DESCRIPTION OF SOME EMBODIMENTS

The principles, uses and implementations of the teachings herein may be better understood with reference to the accompanying description and figures. Upon perusal of the description and figures present herein, one skilled in the art is able to implement the teachings herein without undue effort or experimentation.

Ventilated Portable Container

Figure 1A:
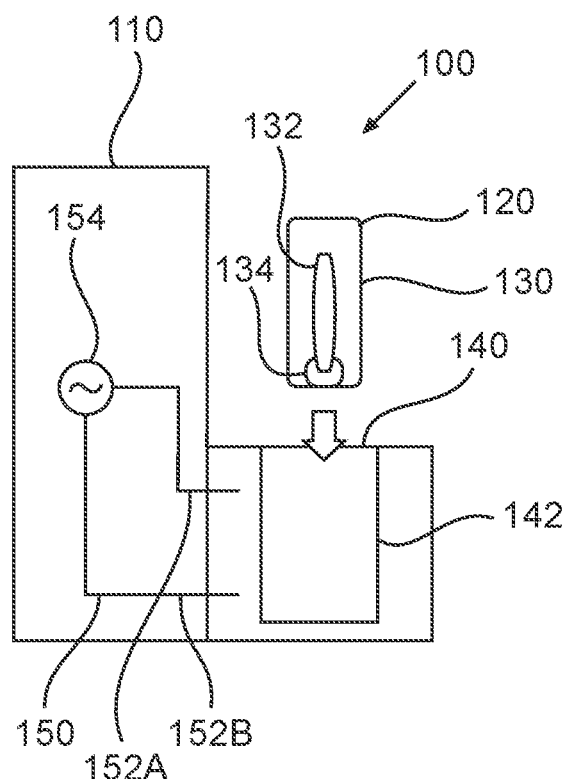
FIG. 1A schematically depicts an embodiment of an apparatus for plasma treatment of an implant, comprising a portable container and an activation device comprising an electrical circuit for applying a plasma-generating electromagnetic (EM) filed in the portable container, according to the teachings herein.

FIGS. 1A-1D schematically depict embodiments of an apparatus 100 for plasma treatment of an implant (implant—including artificial implant, abutment for an implant or graft or biomaterial) prior to installing the implant in a live subject. FIG. 1A depicts a portion of apparatus 100, according to some various embodiments. Apparatus 100 comprises an activation device 110 and a portable container 120. Portable container 120 comprises a closed compartment 130 which contains therein an artificial implant 132 supported by a holder 134 and immersed in a fluid (not shown). Closed compartment 130 may be opened by a user for extracting implant 132 therefrom. The activation device comprises a slot 140 comprising a chamber 142 configured to receive portable container 120 therein.

The closed compartment may be made of or may comprise, in some embodiments, a dielectric material such as plastic or glass. According to some embodiments the closed compartment may be made substantially of metal. According to some embodiment the fluid may be gas, comprising a predefined gaseous composition at a pre-defined pressure. According to some embodiments the gas may be air at ambient conditions (room temperature and pressure). According to some embodiments the fluid comprises a liquid having a pre-defined composition, such as a saline composition at a pre-defined concentration. The closed compartment further contains therein at least one implant configured to be installed in a live subject. In some embodiments the implant—for example, a dental implant—may be metallic, typically being made from a hard alloy such as titanium or stainless steel. In some embodiments the implant may comprise metallic and non-metallic materials such as polymer materials or ceramics, e.g. a joint implant. In some embodiments the implant may comprise silicone, e.g. a breast implant. In some embodiments the implant may be void of metal. In some embodiments the implant may comprise or consist of biomaterial intended to be used in a transplantation procedure, such as bone graft or other types of tissue or artificial substance used for grafting, or a combination thereof. The closed compartment is configured to be opened by a user, thereby enabling removing the implant from the portable container.

Activation device 110 further comprises an electrical circuit 150 comprising electrical conductors 152A and 152B. The electrical circuit comprises an electric power source 154 electrically associated with electrical conductors 152A and 152B and configured to controllably generate an AC electric power (voltage and current) at a desired magnitude and frequency. The electrical circuit may receive energy from an energy source such as a wall outlet or a portable energy source such as an electrical battery. The electrical circuit is configured to drive an AC current through an electrode or electrodes which are electrically associated with power source 154 via electrical conductors 152A and 152B. Various configurations of electrodes are contemplated for applying a plasma-generating electric field inside closed compartment 130, when portable container 120 is disposed in slot 140. According to some embodiments portable container 120 does not include electrodes and plasma is generated in closed compartment 130 thereof using electrodes of the activation device, as described herein. Some non-limiting examples of electrodes configurations are detailed in FIGS. 1B-1D, wherein the electrode or electrodes described in each Figure are electrically associated with the power source 154 by the electrical conductors 152A and 152B.

Figure 1B:
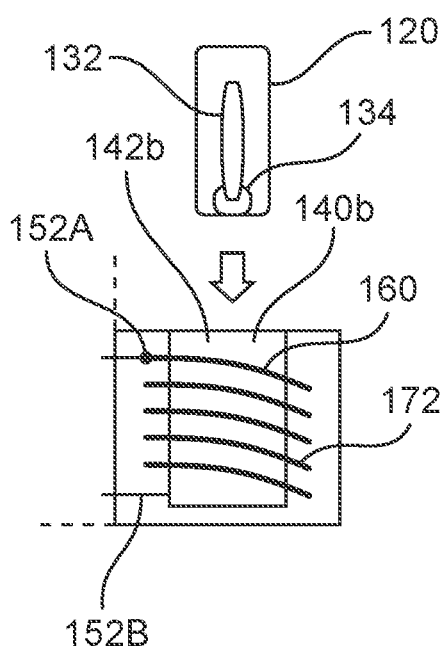
FIG. 1B depicts an exemplary configuration of electrodes of the activation device, suitable to be used with the portable container of FIG. 1A for plasma generation therein.

FIG. 1B schematically depicts a portion of an embodiment of activation device 110 including a chamber 142b and a single electrode 160. Electrode 160 comprises an elongated conductor 162 substantially wound around chamber 142, thereby being wound around implant 132 when portable container 120 is disposed in slot 140b. According to some embodiments, plasma may be generated around implant 132 in chamber 142b, in an Inductive Coupled Plasma (ICP) mode of operation.

Figure 1C:
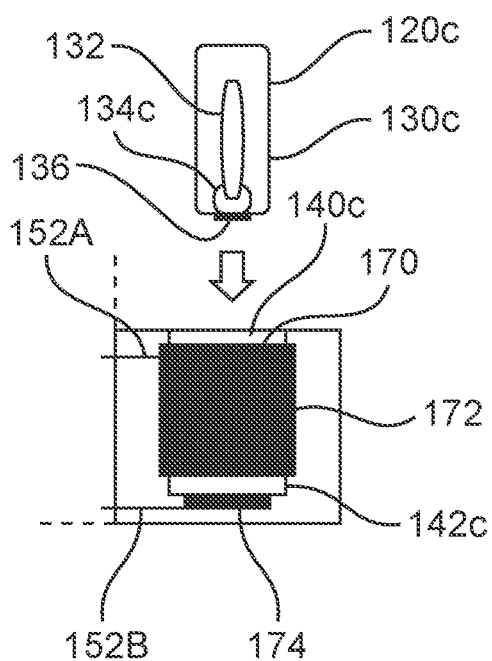
FIG. 1C depicts another exemplary configuration of electrodes of the activation device, suitable to be used with the portable container of FIG. 1A for plasma generation therein.

FIG. 1C schematically depicts a portion of an embodiment of activation device 110 including a chamber 142c and an electrode 170. Electrode 170 comprises a cylindrical conductor 172 substantially enveloping chamber 142c, thereby enveloping implant 132 when portable container 120c is disposed in slot 140c. Portable container 120c comprises an electric contact 136 on a bottom side thereof, being in galvanic contact with an electrically conducting holder 134c inside the closed compartment 130c. A contact 174 inside chamber 142c is configured to deliver electric power to implant 132 via electrically conducting holder 134c when portable container 120 is disposed in slot 140c. Thus a plasma-generating electric field may be generated (upon activation of electrical circuit 150) between cylindrical electrode 170 and at least a portion of a surface of implant 132. According to some embodiments, plasma may be generated around implant 132 in chamber 142c, in a Capacitance Coupled Plasma (CPC) mode of operation and/or in a Dielectric Breakdown Discharge (DBD) mode of operation.

Figure 1D:
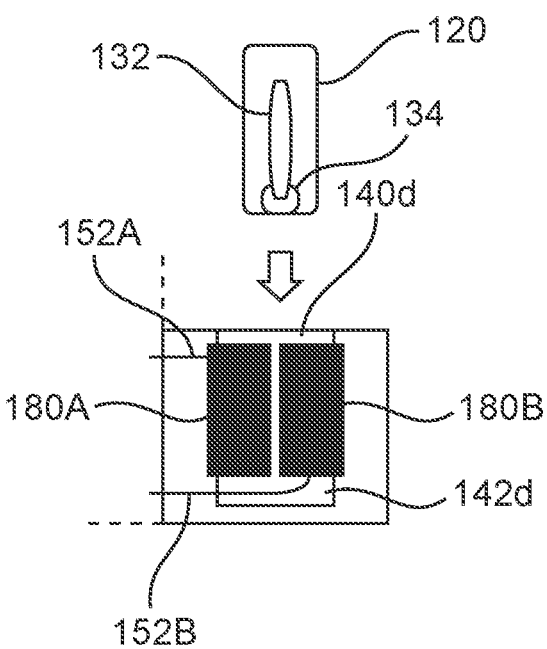
FIG. 1D depicts yet another exemplary configuration of electrodes of the activation device, suitable to be used with the portable container of FIG. 1A for plasma generation therein.

FIG. 1D schematically depicts a portion of an embodiment of activation device 110 including chamber 142d and a pair of electrodes 180A and 180B. Electrodes 180A and 180B are electrically disconnected from one another, and arranged on opposite sides of chamber 142d, being thereby configured to apply a plasma-generating electric field therebetween (and inside in closed compartment 132) is a Capacitance Coupled Plasma (CPC) mode of operation and/or in a Dielectric Breakdown Discharge (DBD) mode of operation, when portable container 120 is disposed in slot 140d.

According to some embodiments the apparatus is configured and operable to apply a plasma-generating electric field in the closed compartment at ambient conditions. That is to say that portable container 120 containing an implant immersed in air at ambient pressure may be placed in slot 140 of the activation device 110, and plasma may be generated in closed compartment 130 by activating the electric circuit. The electric circuit then applies the plasma-generating electric field and plasma is generated, substantially without any further intervention with the closed compartment or with the gas inside. It is noted that the electric field necessary for plasma ignition at such ambient conditions of the atmosphere inside the closed compartment may depend strongly on various factors such as the dielectric barrier imposed by gap between electrodes assuming ambient air fills the gap; and dielectric barrier imposed by the walls of the closed compartment, in embodiments wherein at least one of the electrodes is outside the closed compartment. It is further noted in this regard that the closed compartment may, according to some embodiments, have relatively thin walls, of a relatively penetrable material to air, e.g. such as Perspex, thereby enabling a lower dielectric barrier at the time of plasma activation (compared to a compartment having thick enough walls to maintain vacuum for a period of years).

Figure 2A:
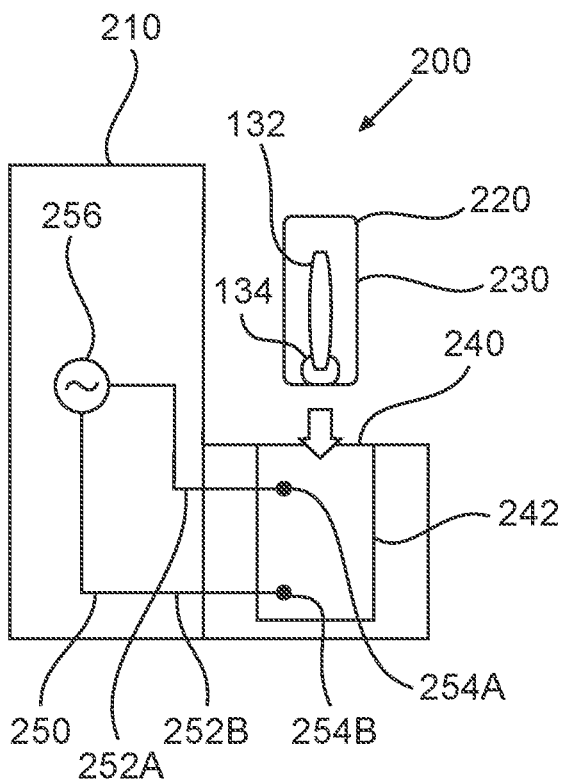
FIG. 2A schematically depicts an embodiment of an apparatus for plasma treatment of an implant, comprising an activation device and a portable container comprising electrodes for applying a plasma-generating electromagnetic (EM) filed therein, according to the teachings herein.

FIGS. 2A-2D schematically depict embodiments of an apparatus 200 for plasma treatment of an implant prior to installing the implant in a live subject. FIG. 2A depicts a portion of apparatus 200, according to some various embodiments. Apparatus 200 comprises an activation device 210 and a portable container 220. Portable container 220 comprises a closed compartment 230 which contains therein implant 132 supported by holder 134 and immersed in a fluid (not shown). Closed compartment 230 may be opened by a user for extracting implant 132 therefrom. The activation device comprises a slot 240 comprising a chamber 242 configured to receive portable container 220 therein.

Activation device 210 further comprises an electrical circuit 250 comprising electrical conductors 252A and 252B, electrically associated with contacts 254A and 254, respectively. The electrical circuit comprises an electric power source 256 electrically associated with electrical conductors 252A and 252B and configured to controllably generate an AC electric power (voltage and current) at a desired magnitude and frequency.

Activation device 210 is different from activation device 110 in that activation device 210 does not include electrodes for applying a plasma-generating electric field. Instead, Activation device 210 is configured to provide electric power to electrodes incorporated in portable container 220 as is further described herein. Various configurations of electrodes are contemplated for applying a plasma-generating electric field inside closed compartment 230, when portable container 220 is disposed in slot 240. Examples of electrodes configurations are detailed in FIGS. 2B-2D, wherein the electrode or electrodes described in each Figure are electrically associated with the power source 256 via the electrical conductors 252A and 252B and electrical contacts 254A and 254B.

Figure 2B:
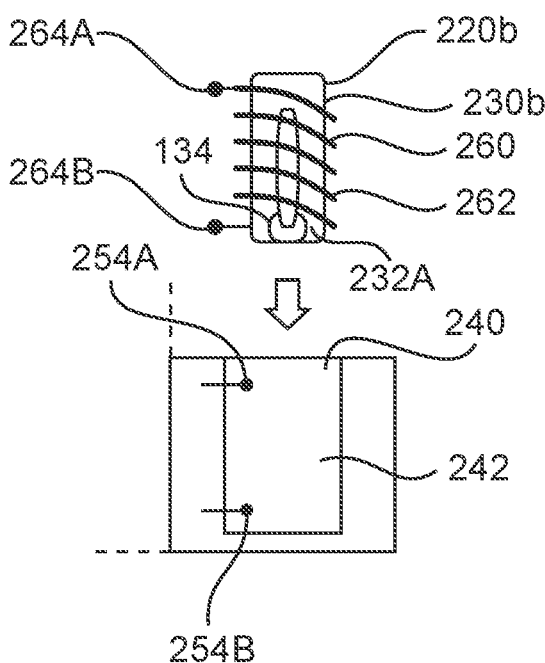
FIG. 2B depicts an exemplary configuration of electrodes of the portable container, suitable to be used with the activation device of FIG. 2A for plasma generation in the portable container.

FIG. 2B schematically depicts an embodiment of apparatus 200, displaying a portion of activation device 210 including slot 240 and a portable container 220b. Portable container 220b comprises closed compartment 230b and an electrode 260 comprising an elongated conductor 262 substantially wound around closed compartment 230b, thereby being wound around implant 132. Electrode 260 is electrically associated with two electrical contacts 264a and 264b. When portable container 220b is disposed in slot 240, electrical contacts 254a and 254b contact electrical contacts 264a and 264b, respectively, thereby allowing supplying to electrode 260 plasma-generating electric filed from power source 256. According to some embodiments, plasma may be generated around implant 132 in portable container 220b, in an Inductive Coupled Plasma (ICP) mode of operation.

Figure 2C:
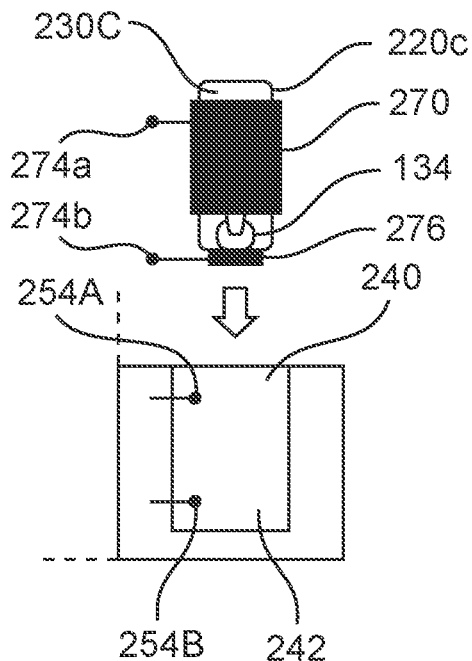
FIG. 2C depicts another exemplary configuration of electrodes of the portable container, suitable to be used with the activation device of FIG. 2A for plasma generation in the portable container.

FIG. 2C schematically depicts an embodiment of apparatus 200, displaying a portion of activation device 210 including slot 240 and a portable container 220c. Portable container 220c comprises a closed compartment 230c and a cylindrical electrode 270 substantially enveloping implant 132. According to some embodiments, electrode 270 substantially envelops closed compartment 230c, thereby enveloping implant 132. A conductor 276 on portable container 220c is electrically associated with implant 132. According to some embodiments, conductor 276 is in galvanic contact with implant 132 via holder 134. Cylindrical electrode 270 is electrically associated with an electrical contact 274a, and conductor 276 on portable container 220c is electrically associated with an electrical contact 274b. Further, when portable container 220c is disposed in slot 240, electrical contacts 254a and 254b contact electrical contacts 274a and 274b, respectively, thereby allowing supplying a plasma-generating electric field from power source 256 between cylindrical electrode 270 and at least a portion of a surface of implant 132. According to some embodiments, electrode 270 is positioned inside closed compartment 230c, e.g. on an inner surface of a wall of the closed container, being thereby facing directly implant 132. According to some embodiments, plasma may be generated around implant 132 in portable container 220c, in a Capacitance Coupled Plasma (CPC) mode of operation and/or in a Dielectric Breakdown Discharge (DBD) mode of operation.

Figure 2D:
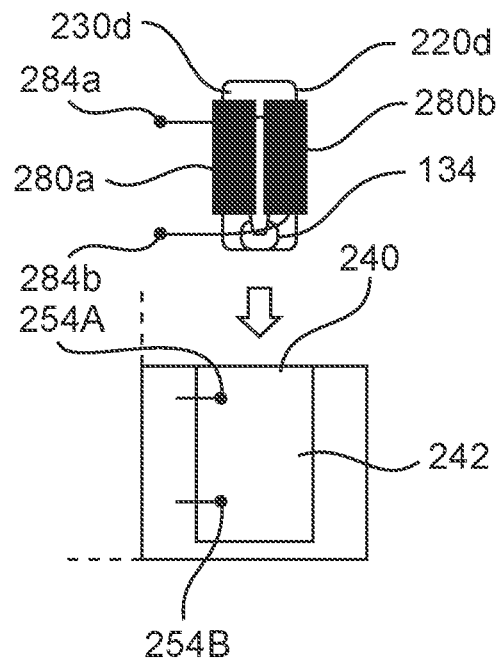
FIG. 2D depicts yet another exemplary configuration of electrodes of the portable container, suitable to be used with the activation device of FIG. 2A for plasma generation in the portable container.

FIG. 2D schematically depicts a portion of activation device 210 including slot 240 and an embodiments of a portable container 220d. Portable container 220d comprises closed compartment 230d and a pair of electrodes 280a and 280b. Electrodes 280a and 280b are electrically disconnected from one another, and arranged on opposite sides of closed compartment 230d. Electrodes 280a and 280b are electrically associated with electrical contacts 284a, and 284b, respectively. Further, when portable container 220d is disposed in slot 240, electrical contacts 254a and 254b contact electrical contacts 284a and 284b, respectively, thereby allowing supplying a plasma-generating electric field from power source 256 between cylindrical electrodes 280a and 280b, thereby generating plasma around at least a portion of the surface of implant 132. According to some embodiments plasma may be generated around implant 132 in portable container 220d in a Capacitance Coupled Plasma (CPC) mode of operation, and/or in a Dielectric Breakdown Discharge (DBD) mode of operation when portable container 220d is disposed in slot 240.

Figures 3, 4A, 4B:
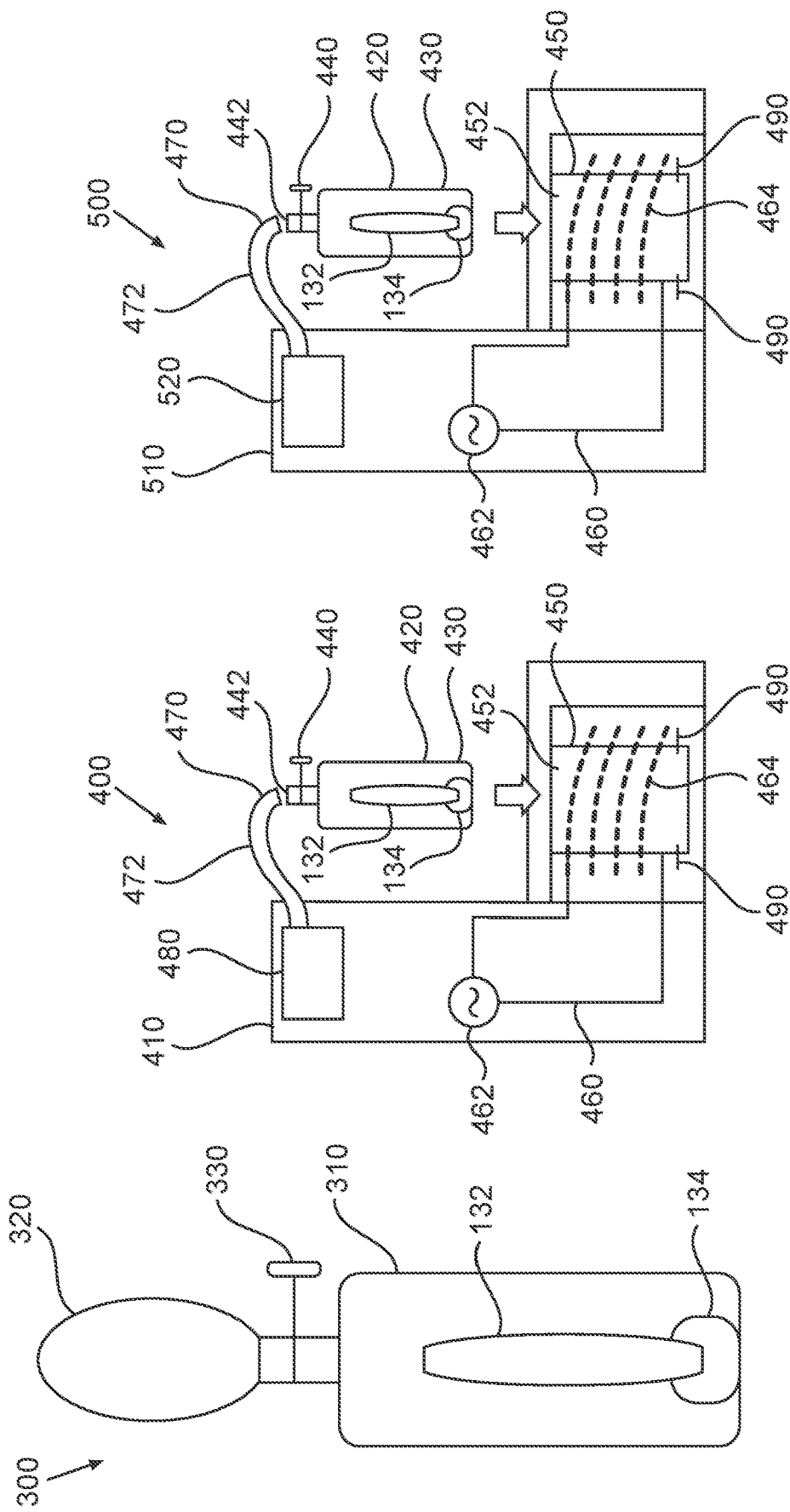
FIG. 3 schematically depicts an embodiment of portable container of the invention, comprising a gas reservoir.
FIG. 4A schematically depicts an embodiment of an apparatus for plasma treatment of an implant, comprising a portable container and an activation device comprising a gas reservoir.
FIG. 4B schematically depicts an embodiment of an apparatus for plasma treatment of an implant, comprising a portable container and an activation device comprising a gas pump.

FIG. 3 schematically depicts an embodiment of a portable container 300 according to an aspect of the invention. Portable container 300 comprises a closed compartment 310 substantially similar to closed compartment 130 described above and containing implant 132 immersed in a fluid. Portable container 300 further comprises a gas reservoir 320 and a valve 330 operable to be opened and closed, which is fluidly associated with closed compartment 310 and with gas reservoir 320. When valve 330 is opened fluid communication between closed compartment 310 and gas reservoir 320 is allowed, and when valve 330 is closed fluid communication between closed compartment 310 and gas reservoir 320 is disabled. According to some embodiments, gas reservoir 330 may contain pressurized ionizable gas such as an inert gas, e.g. helium, argon, nitrogen etc., suitable for plasma ignition. According to some embodiments gas reservoir 320 may contain gas at a very low pressure (e.g. 0.1 atmosphere or even 0.01 atmosphere or even less). According to some embodiments, portable container 300 may be used for storing and shipping implant 132 in ambient conditions (that is, implant 312 being immersed in air, which may be ionized at a higher field compared to other gases such as argon at atmospheric pressure, or compared to air at a lower pressure). Accordingly, stringent sealing may not be required of closed compartment 310, thereby reducing cost and complexity of closed compartment 310. For plasma treating implant 132 inside closed compartment 310 prior to using implant 312, valve 330 may be opened, thereby flushing closed compartment 310 with the gas of gas reservoir 320. According to some embodiments closed container 310 may be closed but not sealed, thereby allowing excess gas to exit from closed compartment 310 and thereby maintain the pressure inside closed compartment 310 substantially equal to ambient pressure. Alternatively, gas reservoir 320 contains gas at a very low pressure and valve 330 may be opened thereby partially evacuating closed compartment 310 into gas reservoir 320. According to some embodiments closed compartment 310 may be sealed so that vacuum is maintained inside (if closed compartment is evacuated into gas reservoir 320) for a period of time sufficient to carry out plasma treatment to the implant—e.g. for 10 minutes or for 2 minutes or even for 1 minute. Portable container 300 may be further disposed in a slot of an activation device such as activation device 110 or 210 as described above, and an electric circuit may be activated to apply a plasma-generating electric field inside closed compartment 310. Various embodiments of portable container 300 are contemplated, that are compatible with the activation devices described herein. Further, embodiments of portable container 300 are compatible with electrodes configurations described in FIGS. 1A-1D and/or with the activation device and electrodes configurations described in FIGS. 2A-2D.

FIG. 4A schematically depicts an embodiment of an apparatus 400 for plasma treatment of an implant prior to installing the implant in a live subject. Apparatus 400 comprises an activation device 410 and a portable container 420. Portable container 420 comprises a closed compartment 430 substantially similar to closed compartment 120 described above and containing implant 132 immersed in a fluid. Portable container 420 further comprises a valve 440 and a valve port 442. Valve 440 is operable to be opened and closed, thereby fluidly associating and disassociating, respectively, valve port 442 with closed compartment 430.

Activation device 410 comprises a slot 450 comprising a chamber 452 configured to receive portable container 420 therein. Activation device 410 further comprises an electrical circuit 460 comprising an electric power source 462 configured to controllably generate an AC electric power (voltage and current) at selected magnitude and frequency. Electrical circuit 460 may be embodied in various configurations, including the configurations illustrated in FIGS. 1B-1D and 2B-2D, with electrodes associated with the slot of the activation device or alternatively with the closed compartment of the portable container 420. An electrode 464 comprising an elongated conductor wound around chamber 452 and illustrated with a dashed line exemplifies one particular, non-limiting, possible configuration of such electrodes.

Activation device 410 is different from activation devices 110 or 210 described above in comprising a fluid port 470 which is configured to fluidly connect to valve port 442 when portable container 420 is disposed in slot 450. Fluid port 470 may be used according to some embodiments to flush closed compartment 430 with a desired ionizable gas such as an inert gas, e.g. helium, argon, nitrogen etc., suitable for plasma ignition and generation. Accordingly, fluid port 470 may be fluidly associated, via a controlled valve (not shown here) with a fluid source such as a gas reservoir 480 (maintained either inside activation device 410 or separated from the activation device). According to some embodiments fluid port 470 may be fluidly associated with gas reservoir 480 via a hose or a pipe 472. Thus, according to some embodiments, portable container 410 may be used for storing and shipping implant 132 in ambient conditions (that is, implant 312 being immersed in air). As described above, stringent sealing may not be required of closed compartment 430, thereby reducing cost and complexity of portable container 420. For plasma treating implant 132 inside closed compartment 430 prior to using implant 132, portable container 420 may be placed in slot 450 and fluid port 470 may be connected to valve port 442. Valve 440 (and the controlled valve, not shown here, associated with fluid port 470) may then be opened, thereby fluidly connecting fluid port 470 with closed compartment 430 and enabling flushing closed compartment 430 with the gas of gas reservoir 480. According to some embodiments closed compartment 430 may be closed but not sealed, thereby allowing excess gas to exit from closed compartment 430 and thereby maintain the pressure inside closed compartment 310 substantially equal to ambient pressure (e.g. atmospheric pressure), alas with the gas of gas reservoir 480, which may be ionized at a lower field compared to air.

FIG. 4B schematically depicts an embodiment of an apparatus 500 for plasma treatment of an implant prior to installing the implant in a live subject. Apparatus 500 comprises an activation device 510 and portable container 420. Apparatus 500 is different from apparatus 400 in that activation device 510 comprises, instead of gas reservoir 480, a vacuum pump 520 fluidly associated with fluid port 470 via a controlled valve (not shown here) and possibly via a hose or a pipe 472. Accordingly, during activation of device 510, fluid port 470 may be used to fluidly connect valve port 442 with vacuum pump 520 to pump closed compartment 430 to a desirable low pressure, e.g. 0.1 atmosphere or even 0.01 atmosphere, for a period of time required to activate the plasma inside closed compartment 430 and carry out the plasma treatment of implant 132. Thus, according to some embodiments, portable container 410 may be used for storing and shipping implant 132 in ambient conditions (that is, implant 312 being immersed in air substantially at atmospheric pressure). As described above, stringent sealing may not be required of closed compartment 430, thereby reducing cost and complexity of portable container 420. For plasma treating implant 132 inside closed compartment 430 prior to using implant 132, portable container 420 may be placed in slot 450 and fluid port 470 may be connected to valve port 442. Valve 440 may then be opened, thereby fluidly connecting vacuum pump 520 with closed compartment 430 and enabling pumping closed compartment 430 using pump 520. According to some embodiments closed compartment 430 may be sealed to such as extent so as to maintain a desired low pressure for a desired period of time sufficient for the plasma treatment (e.g. for 10 minutes, or for 1 minute or even for 0.5 minute), thereby considerably facilitating plasma ignition and maintaining.

To conform to sterility standards related to handling an implant prior to installment in a live subject, plasma activation is performed in a non-sterile environment (e.g. a non-sterile room and using hands and tools that have not necessarily been sterilized). Then the portable container may be carried, e.g. using unsterilized tools or hands, into sterile surroundings. The sterile implant may then be removed from the sealed compartment and disposed onto a sterile tray for the use of a surgeon, or directly to the sterile hands of a surgeon or the like. According to some embodiments the portable container may comprise an external capsule and an internal capsule contained in the external capsule and containing the implant therein. Following plasma treatment (in the space around the implant inside the internal capsule), the external capsule may be opened for removing the internal capsule with the implant therefrom. Then, in the sterile environment and using sterile tools and hands, the internal capsule may be opened and the sterile implant may be extracted therefrom to be installed in the patient.

Accordingly, the external capsule may further be configured and dimensioned for freely releasing the internal capsule when the external capsule is opened. Being configured for freely releasing the internal capsule herein means that following opening the external capsule, the internal capsule may be extracted and removed from the opened external capsule without touching the internal capsule. For example, the external capsule may have an opening that may be closed by a cap. A user may open the external capsule by removing the cap and then freely releasing the internal capsule from the external capsule by holding the external capsule so that the opening faces downwards, thereby letting the internal capsule fall down and out from the external capsule through the opening. In some embodiments the internal capsule may be held tight inside the external capsule, whereas a releasing mechanism operated by the user may be used to release the internal capsule from the holding without having the user touch directly the internal capsule, thereby freely releasing the internal capsule from the external capsule.

According to some embodiments activation devices 410 and 510 may comprise one or more ignition electrodes 490 positioned proximal the slot 450, preferably in the chamber 452 and specifically proximal the portable container 420 when the portable container is disposed in the slot. Ignition electrodes 490 are connected to a high voltage ignition pulse generator (not shown here) and configured for applying a high-voltage ignition pulse to facilitate plasma ignition and plasma generation, as is further described and detailed herein below, specifically concerning a plasma chamber depicted in FIGS. 10A and 10B, and concerning a high voltage ignition pulse generator depicted in FIG. 13. It should be understood that all activation devices described here may similarly include ignition electrodes electrically connected to a high voltage ignition pulse generator for facilitating plasma ignition and plasma generation.

FIG. 5A schematically depicts an embodiment of a portable container 600 according to the teachings herein, comprising an external capsule 610 and an internal capsule 620 inside external capsule 610. External capsule 610 and internal capsule 620 are made substantially of electrically isolating materials such as a polymer or glass. Internal capsule 620 is supported inside external capsule 610 by supporters 612. External capsule 610 comprises an openable cap 614, enabling opening external capsule 610, and extracting internal capsule 620 therefrom. According to some embodiments, external capsule 610 may be dimensioned and configured for freely releasing internal capsule 620 when external capsule 610 is opened. Internal capsule 620 may function as a closed compartment as described above, containing therein implant 132 supported by holder 134 and being immersed in a fluid. Internal capsule 620 comprises an openable cap 622 enabling opening internal capsule 620 for extracting implant 132 therefrom.

Portable container 600 may further comprise according to some embodiments an electrode 630 for applying a plasma-generating electric field inside the internal capsule 620 and around implant 132. Electrode 630 may be electrically connected to electrical contacts 432 outside external capsule 610, for enabling connecting to a suitable power supply for supplying to the electrode a plasma-generating electric field. Various electrode configurations are contemplated in various embodiments of portable container 600. According to some embodiments at least one electrode or all of the electrodes may be inside the internal capsule or outside the internal capsule and inside the external capsule or outside the external capsule. According to various embodiments, various electrical configurations of the electrodes are contemplated, e.g. as described above in FIGS. 1B-1D.

According to some embodiments, external capsule 610 and internal capsule 620 are closed but not sealed, hence implant 132 may be stored and shipped inside portable container 600 at ambient conditions. According to some embodiments, plasma is generated inside internal capsule 620 whereas implant 132 is immersed in air at atmospheric pressure and composition. According to some embodiments, the portable container further comprises a valve 640 fluidly associated with external capsule 610. Valve 640 may be used to flush external capsule with a gas from a gas reservoir, as is described above, for example, in FIG. 4A. Valve 640 may further be used to pump external capsule 610 as is described above, for example, in FIG. 4B. According to some embodiments internal capsule 620 may be closed but not sealed, allowing pressure and composition inside external capsule 610 and internal capsule 620 to equalize relatively quickly (e.g. within about 10 minute or even within 1 minute or even within 10 seconds) when external capsule 610 is flushed with gas or pumped. According to some embodiments inner capsule 620 comprises a unidirectional valve (not shown here) allowing gas flow out from internal capsule 620 into external capsule 620, but prevents gas flow in the opposite direction. Thus, according to some such embodiments, evacuating the external chamber may lead to the (partial) evacuation of the internal capsule. For employing plasma treatment to implant 132, portable container 600 may be used with an activation device as described above, e.g. such as activation devices 100, 200, 400 or 500.

FIG. 5B schematically depicts an embodiment of a portable container 650 according to the teachings herein, comprising an external capsule 610 and an internal capsule 652 inside external capsule 610. External capsule 610 and internal capsule 652 are made substantially of electrically isolating materials such as a polymer or glass. Portable container 650 further comprises a floating electrode 660, configured to facilitate plasma excitation inside internal capsule 652 when subject to a plasma-generating electric field applied by electrodes outside the external capsule, as is detailed below. Internal capsule 652 may be supported inside external capsule 610 by one or more supporters 612. External capsule 610 comprises an openable cap 614, enabling opening external capsule 610, and extracting internal capsule 652 therefrom. According to some embodiments, external capsule 610 may be dimensioned and configured for freely releasing internal capsule 652 when external capsule 610 is opened. Internal capsule 652 may function as a closed compartment as described above, containing therein implant 132 supported by holder 134 and being immersed in a fluid. Internal capsule further comprises an electrically conducting plate 654 on a bottom side thereof. Functioning substantially similarly to conductor 276 in FIG. 2C, electrically conducting plate 654 enables a galvanic contact between the outside of internal capsule 254 and implant 132, via holder 134. Internal capsule 652 further comprises an openable cap 622 enabling opening internal capsule 652 for extracting implant 132 therefrom.

Portable container 650 may further comprise according to some embodiments a first electrode 662 and a second electrode 664 for applying a plasma-generating electric field inside the internal capsule 620 and around implant 132. First electrode 662 and second electrode 664 may be electrically connected, respectively, to electrical contacts 432a and 432b outside external capsule 610, for enabling connecting to a suitable power supply for supplying to the electrodes a plasma-generating electric field. Various electrode configurations are contemplated in various embodiments of portable container 650. FIG. 5B depicts an exemplary embodiment wherein first electrode 662 is cylindrical, enveloping external capsule 610 on the outside thereof. Second electrode 664 comprises a plate or a slab on the bottom of external capsule 610, on the outside thereof.

Floating electrode 660 is made substantially of an electrically conducting material and may be formed as a helical elongated conductors as depicted in FIG. 5B. Additionally or alternatively, floating electrode 660 may be shaped as a hollow cylinder, or any other suitable shape dimensioned to be disposed inside external capsule 610 and outside internal capsule 652. It is noted that floating electrode 660 is electrically (galvanically) disconnected from first electrode 662 and from second electrode 664.

In operation second electrode 664 induces (e.g. via capacitive coupling) an electric field onto electrically conducting plate 654, and hence onto implant 132. First electrode 662 induces an electric field in the inside of external capsule 610. Floating electrode 660 is configured to diminish the electrical potential barrier formed by the gap between external capsule 610 and internal capsule 652, thereby facilitating considerably plasma excitation inside the internal capsule by voltage (e.g. RF high voltage) supplied between the first electrode 662 and the second electrode 664.

It should be understood by the person skilled in the art that a floating electrode disposed in a gap between an external capsule and an internal capsule of the invention may be effective in facilitating plasma excitation inside the internal capsule also when electrodes different from first electrode 662 and second electrode 664 in FIG. 5b are employed. In other words, in a portable container comprising an external capsule and an internal capsule inside the external capsule and one or more electrodes disposed outside the external capsule configured to receive electric power from a power source, a floating electrode disposed between the external capsule and the internal capsule and electrically isolated form the other electrodes may facilitate plasma excitation inside the internal capsule. For example, various electrode configurations are contemplated in various embodiments of portable container 650 e.g. as described above in FIGS. 1B-1D. According to some embodiments, portable container 650 may be equipped with a fluid port (not shown here) as described above in FIG. 5A, for evacuating the external capsule or fir flushing the external capsule with a gas from a gas reservoir. Thus, for generating plasma inside closed compartment 652, portable container 650 may be used with an activation device as described above, e.g. such as activation devices 100, 200, 400 or 500.

FIG. 6 schematically depicts an embodiment of a portable container 680 according to an aspect of some embodiments, comprising a closed compartment 682 containing implant 132 inside and an electrode 684 comprising an elongated conductor 686 wound around a cylindrical core 688 made of a dielectric, non-magnetic material, conductor 686 having both ends electrically interconnected. Electrode 684 is disposed inside the closed compartment, substantially surrounding the implant. Electrode 684 is electrically connected to a first contact 690a outside closed compartment 682 e.g. via a sealed feed-though (nor shown here). Implant 132 is electrically connected to a second contact 690b outside closed compartment 682 e.g. via a sealed feed-though (not shown here) and via holder 134. Portable container 680 may be used for providing plasma treatment to implant 132 as described herein, for example together with activation device 210 of FIG. 2A.

According to an aspect of the invention, for plasma-treatment prior to installing, an implant may be removed from the container in which it was stored and shipped, and then be placed in an activation device for the plasma treatment. FIG. 7A schematically depicts an activation device 700 for plasma treatment of an implant 132 prior to installing the implant in a live subject. Activation device 700 comprises an implant holder 134 configured to support the implant during plasma treatment, and an electrical circuit 710 comprising at least one electrode 712 and an electric power source 714. The electric circuit is configured to provide to the at least one electrode 712 electric power suitable for applying a plasma generating electric field near the implant 132 when the implant is supported by the implant holder 134. According to some embodiments the activation device comprises a chamber 720, dimensioned to contain the implant therein when the implant is supported by holder 134. Chamber 720 may be an open chamber according to some embodiments and may be a closable chamber, having a closure (not shown) configured to close the chamber according to some embodiments. According to some embodiments the chamber may be closed but not sealed.

In the activation device 700 the implant may undergo plasma treatment (upon activation of the electric circuit 710) at ambient conditions, that is to say when immersed in air substantially at atmospheric pressure. Various electrode configurations allowing generating plasma in air at ambient conditions are contemplated, including, e.g. the configurations described in FIGS. 1B-1D and in FIG. 6. For generating plasma in air using voltages that are as low as possible so as to avoid working at very high voltages (e.g. avoid working above 10 KV or even avoid working above 5 KV), air gaps over which plasma is ignited should be minimized in width. Accordingly, the electrode or electrodes 712 are shaped and dimensioned according to the implants shape and dimension. It is further noted that direct contact between an electrode and the implant should also be avoided to allow space for plasma to ignite, to prevent arcing and to prevent the focusing of the plasma in one location on the surface of the implant. According to some embodiments electrode(s) 712 may be distanced from implant 132 during the plasma activation by less than about 2 mm or by less than about 1 mm or even by less than about 0.5 mm. According to some embodiments the electrodes are isolated, that is to say coated by an isolating material (e.g. glass or a polymeric material) thereby generating plasma in a dielectric breakdown discharge (DBD) mode of operation. Preferably, the electrode isolation is thin enough to ensure a gap between the isolation and the implant, thereby ensuring non-contact of the implant with the electrode or with the electrode isolation.

According to some embodiments facilitating plasma generation around implant 132 is achieved by reducing the pressure around the implant or by flushing the implant surroundings by an ionizable gas in which plasma ignition is easier (that is to say—may be achieved using a lower voltage) compared to air. As described above an inert gas such helium, argon or nitrogen may be used. FIG. 7B schematically depicts an activation device 750 for plasma treatment of an implant 132 prior to installing the implant in a live subject. Device 750 is different from device 700 by further comprising a fluid transfer system 760 configured to fluidly connect to chamber 720 and to transfer fluid into chamber 720 or out from chamber 720. According to some embodiments fluid transfer system 760 comprises a gas reservoir 762 which, during plasma generation, is fluidly connected to chamber 720. According to some embodiments chamber 720 may be closed during plasma generation using a cap 770 connected to fluid transfer system 760, thereby being fluidly connected with gas reservoir 762. According to some embodiments chamber 720 may be closed but not sealed so that excess gas flushing the chamber from gas reservoir 762 may flow out of chamber 720, thereby maintaining atmospheric pressure in the chamber. According to some embodiments fluid transfer system 760 may comprise a gas pump 764 (rather than gas reservoir 762), thereby enabling pumping gas from chamber 720 and reducing the pressure therein during plasma activation. It is noted that effective pressure decrease (e.g. to a pressure of 0.1 atmosphere or even to a pressure of 0.01 atmosphere) to facilitate plasma ignition and generation may be obtained even if chamber 720 is closed but not entirely sealed, because chamber 720 is dimensioned to fit to the dimensions of implant 132, thereby containing relatively small free volume that should be pumped. According to some embodiments an effective plasma treatment to an implant using the apparatuses described herein, including time required for flushing or for pumping, may be less than 10 minutes, or less than about 2 minutes or even less than about 1 minute. According to some embodiments an activation device (not depicted here) is provided, having a gas reservoir such as gas reservoir 762 configured to be fluidly connected with chamber 720 via a first cap such as cap 770, the activation device also comprises a (separate) gas pump such as gas pump 764, configured to be fluidly connected with chamber 720 via a second cap such as cap 770. According to some embodiments, the activation device is configured to flush the chamber with gas from the gas reservoir while removing excess gas from the chamber via the gas pump, thereby reaching a desired composition and pressure of the gas inside the chamber for plasma generation.

According to some embodiments activation devices 700 and 750 may comprise one or more ignition electrodes 790 positioned in the chamber 720 and specifically proximal the implant 132 when the implant is disposed in the chamber. Ignition electrodes 790 are connected to a high voltage ignition pulse generator 792 and configured for applying a high-voltage ignition pulse to facilitate plasma ignition and plasma generation, as is further described and detailed herein below, specifically concerning a plasma chamber depicted in FIGS. 10A and 10B, and concerning a high voltage ignition pulse generator depicted in FIG. 13.

Certifying the Portable Container

According to an aspect of the invention, it would be advantageous to certify a portable container housing an implant therein, for activating plasma, prior to such plasma activation and/or during such plasma activation. For example, it may be necessary or at least advantageous to certify that a portable container is properly positioned in a dedicated slot of an activation device, to ensure proper plasma activation inside the compartment of the container. For example it may be advantageous to prevent the generation of high-voltage (intended to ignite plasma or to generate plasma or to maintain plasma inside the container), if a container in absent from the slot or misplaced in the slot. Such prevention of high-voltage generation may be needed to prevent accidental electrification of a user or undesired arcing, or other undesired results of unsuccessful delivery of the plasma generating field to the container. According to some embodiments accurate positioning of the container inside the slot may be necessary to ensure suitable coupling of the electric voltage generated by the activation device to the compartment housing the implant. For example, it may be necessary or at least desired to ensure electric contact of the RF power supply in the activation device with electrodes of the container. In some embodiments such accurate positioning of the container in the slot may be necessary to ensure suitable and proper impedance matching between the container and the activation device. According to some embodiments, it is necessary or at least desirable to ensure that plasma has actually ignited inside the compartment of the container, to validate the plasma treatment and to prevent mistaken implantation of an implant that did not undergo plasma treatment. According to some embodiments it may be necessary, or at least desirable, to associate and apply a particular plasma treatment protocol to a particular type of implant, by identifying the container in which the implant is stored. In other words, different types of implants may be stored for plasma treatment in different containers, wherein each type of implant may be identified by an identification component embedded in the container. When the container is positioned in the slot of the activation device, the activation device may identify the type of the implant by recognizing the identification component of the container, thereby preventing applying plasma according to a wrong protocol, and ensuring applying plasma according to a correct and suitable protocol. Thus, according to an aspect of the invention, an apparatus for plasma treatment of an implant is provided comprising an activation device and a portable container (detachable from the activation device). The apparatus further comprises a container certification system comprising a field transponder attached to one of the activation device and a portable container and a receiver, attached to the other of the activation device and a portable container. A signal transmitted from the field transponder may be received by the receiver, thereby certifying the identity of the portable container or the position thereof relative to the activation device. According to some embodiments the certification system further comprises transmitter positioned also on the other one of the activation device and a portable container. According to some embodiments, the transmitter may transmit a transmitted signal to which the field transponder may respond with a response signal which is received by the receiver. The filed transponder may be passive (such as a reflector) or may be active (powered by an energy source).

Figure 8B:
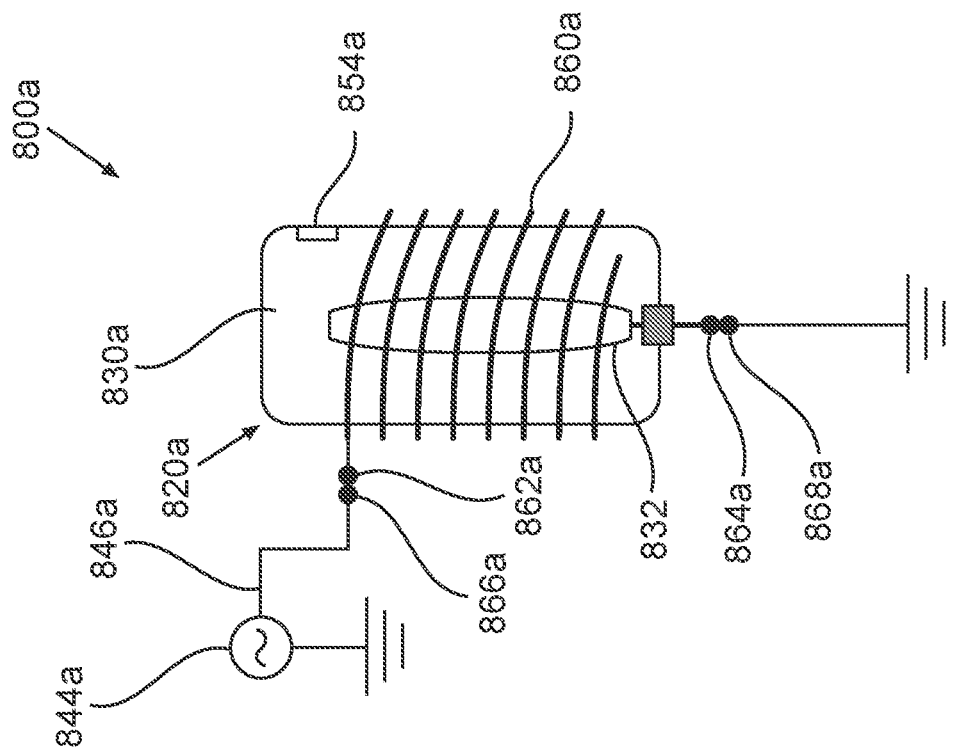
FIG. 8B schematically depicts an embodiment of an apparatus different from the apparatus of FIG. 8A in that the electrode for producing a plasma-generating electric field, is accommodated with the portable container and not with the activation device.
Figure 8A:
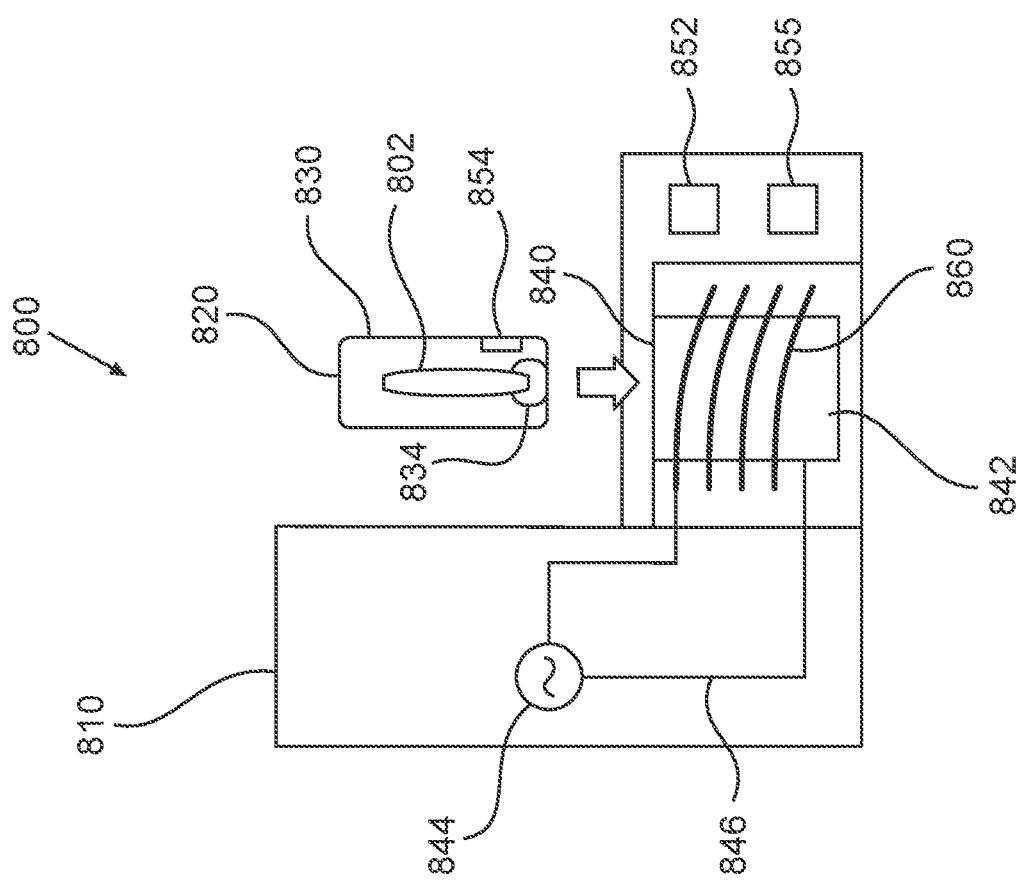
FIG. 8A schematically depicts an embodiment of an apparatus, according to the teachings herein, for plasma treatment of an implant inside a portable container comprising a field transponder, the apparatus being configured to certify a suitable positioning of the portable container relative to the activation device, or the type of the implant there inside.

FIG. 8A schematically depicts an embodiment of an apparatus 800 for plasma treatment of an implant 802 (implant—including artificial implant, abutment for an implant or graft or biomaterial) prior to installing the implant in a live subject substantially according to the teachings herein. Apparatus 800 comprises an activation device 810 and a portable container 820. Portable container 820 comprises a closed compartment 830 which contains therein artificial implant 802 supported by a holder 834. According to some embodiments closed compartment 830 may be sealed, thereby maintaining therein vacuum or an atmosphere that is markedly different in pressure and composition from ambient atmosphere (i.e. air). According to some embodiments, closed compartment 830 is not sealed, as described herein above. The activation device comprises a slot 840 comprising a chamber 842 configured to receive portable container 820 therein. Activation device 810 comprises a power generator 844 configured to generate electric power—e.g. power at a high voltage and high frequency—suitable to produce a plasma-generating electric field in closed compartment 830. Closed compartment 830 may be opened by a user—preferably following a plasma treatment—for extracting implant 802 therefrom.

Activation device 810 further comprises a transmitter 850 configured to transmit a signal towards portable container 820. According to some embodiments, transmitter 850 is configured to transmit the signal towards portable container 820 when portable container 820 is proximal to slot 840 or inside slot 840. Activation device 810 further comprises a receiver 852 configured to receive from portable container 820 a response signal, namely a reflected or transmitted signal respective to the transmitted signal transmitted from transmitter 850. Portable container 820 comprises a field transponder 854, configured to reflect or to transmit the response signal, in response to the signal transmitted from transmitter 850. The signal transmitted towards the portable container and/or from the portable container towards receiver 852 may be wireless (e.g. an electromagnetic signal such as a RF signal or an optical signal) or may be wired using electrical contacts, as is exemplified herein below.

According to some embodiments transmitter 850 is a directional transmitter, configured to transmit along a predetermined direction, and field transponder 854 is localized, so that only when portable container is suitably positioned in a well-defined position, e.g. in slot 840, field transponder 854 is positioned in the direction of the transmitted signal from transmitter 850, and consequently responds back a response signal. According to some embodiments field transponder 854 is passive, thereby passively reflecting a portion of the transmitted signal. According to some embodiments field transponder 854 is active thereby actively transmitting a response signal (which may be different in frequency or have a stronger intensity compared to the transmitted signal from transmitter 850). According to some embodiments an active field transponder 854 may be energized by a portable energy source such as a battery. According to some embodiments transmitter 850 is not necessary, and active field transponder 854 may be configured to actively transmit a certifying signal which certifies the validity of portable container 820 or the position thereof when received by receiver 854. According to some such embodiments, active field transponder 854 may include a light source, or a directed light source such as a laser or a LED, configured to be directed towards received 852 in the activation device when the portable container is suitably positioned in the slot. According to some embodiments active field transponder 854 may transmit a coded RF signal which may be received by receiver 852 when the portable container is suitably positioned in the slot. According to some embodiments, active field transponder 854 may be energized by a portable energy source such as a battery which is comprised by the portable container. According to some embodiments active field transponder 854 may be energized—either wirelessly or through electric wires—by an energy source of the activation device. According to some embodiments electric contacts on the portable container and on the slot of the activation device may come into mutual electric contact when the portable container is inserted into the slot, so as to close an electric circuit that allows activation (energizing) active field transponder 854. According to some embodiments activation device 810 may further comprise a controller (not shown here) functionally associated with receiver 852. According to some embodiments the controller may receive an output from receiver 852 indicating receiving a response signal from field transponder 854. According to some embodiments the controller may be functionally associated with power source 844, to control power source 844 to generate power when a response signal is received in receiver 852, and not to generate power when a response signal is not received in receiver 852.

Apparatus 800 is configured so that activation device 810 comprises an electrode 860 electrically associated with power source 844 to produce a plasma-generating EM field in portable container 820. Accordingly, portable container 820 is void of (lacking) an electrode for producing a plasma-generating field. FIG. 8B schematically depicts an embodiment of an apparatus 800*a* comprising an activation device (not shown) which comprises a power source 844*a*, and a portable container 820*a*. Apparatus 800*a* is different from apparatus 800 in that the activation device of apparatus 800*a* is void of an electrode for producing a plasma-generating electric field, and correspondingly, portable container 820*a* comprises an electrode 860*a* suitable for producing a plasma-generating electric field inside the closed compartment 830*a*. It is noted that electrode 860*a* may be electrically associated with power source 844*a* when portable container 820*a* is suitably positioned in the slot (not shown here) of the activation device, so that contacts 862*a* and 864*a* of portable container 820*a* electrically contact contacts 866*a* and 868*a*, respectively, of the activation device.

According to the teachings herein, portable container 820*a* comprises a field transponder 854*a* configured to reflect or transmit a response signal in response to a transmitted signal from the activation device, as is described above regarding FIG. 8A. According to some embodiments, a response signal is reflected or transmitted by field transponder 854*a* only when portable container 820*a* is suitably positioned inside the slot of the activation device, thereby certifying that electrode 860*a* is electrically associated with power source 844*a* via contacts 862*a*, 866*a*, 864*a* and 868*a*.

According to some embodiments, transmitter 850, receiver 852 and field transponder 854 (and transmitter 850*a*, receiver 852*a* and field transponder 854*a*, respectively) may be shielded, e.g. by an electromagnetic shield (not shown here), to prevent interference of the plasma excitation filed with their operation. Each of the transmitter, the receiver and the field transponder may or may not be shielded. Such shielding may be required or not depending on several considerations including whether or not interference from the plasma excitation field impairs the operation of the transmitter, the receiver or the field transponder.

Figure 9A:
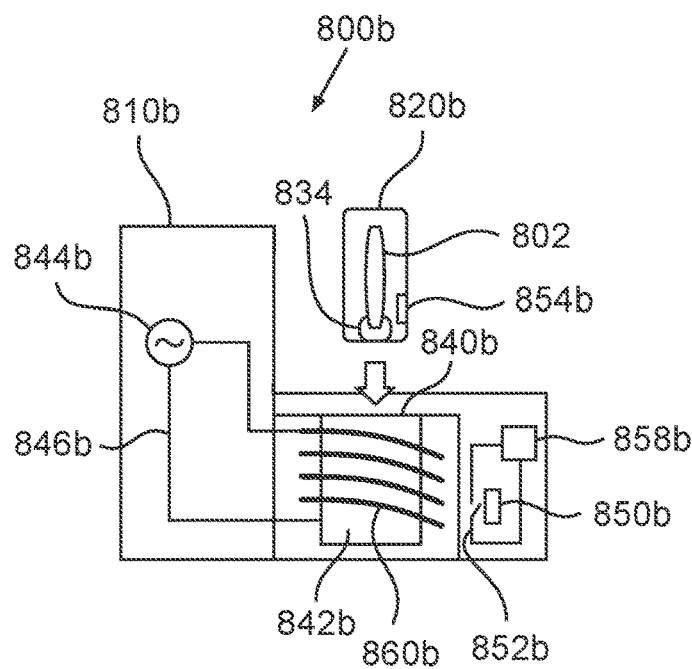
FIG. 9A schematically depicts an exemplary embodiment of the apparatus of FIG. 8A, wherein a magnetic field is used for the certification of the portable container.

FIGS. 9A-9F schematically exemplify some embodiments of corresponding apparatuses configured for certifying a portable container having a field transponder according to the teachings herein. FIG. 9A schematically depicts an apparatus 800*b*, comprising an activation device 810*b* and a portable container 820*b*. Activation device 810*b* comprises a ferromagnet 850*b* positioned near slot 840*b* and mechanically associated with a switch 852*b*. Portable container 820*b* comprises a ferromagnetic slab 854*b* (e.g. a slab of iron or a magnet). When portable container 820*b* is inserted into slot 840*b*, a magnetic field between ferromagnet 850*b* and ferromagnetic slab 854*b*, together, causes switch 852*b* to close a circuit thereby certifying that portable container 820*b* is suitably positioned in slot 840*b*. Switch 852*b* may be functionally associated with a controller 858*b*, the controller being configured to control the activation of power source 844*b* (or otherwise control the application of a plasma-generating EM field in the portable container) as described above, according the state (open or close) of switch 852*b*. According to various embodiments, both ferromagnet 850*b* and ferromagnetic slab 854*b* are magnets; or ferromagnet 850*b* is a magnet whereas ferromagnetic slab 854*b* is not a magnet; or ferromagnetic slab 854*b* is a magnet whereas ferromagnet 850*b* is not a magnet.

Figure 9B:
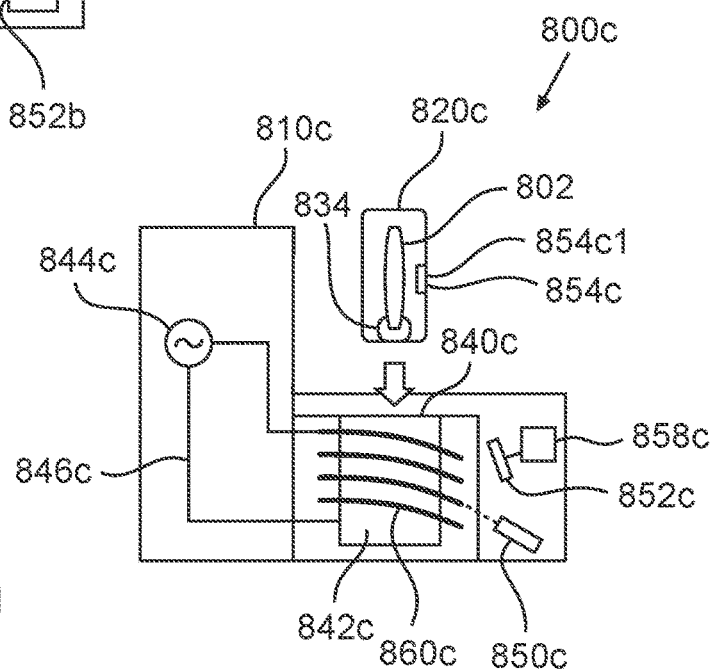
FIG. 9B schematically depicts an exemplary embodiment of the apparatus of FIG. 8A, wherein a light beam is used for the certification of the portable container.

Activation device 800*c* schematically depicted in FIG. 9B comprises light source 850*c* such as a LED or a focused beam source such as a laser. Light produced by light source 850*c* is directed towards chamber 842*c*, possibly through a window or an opening in the chamber (not shown here). When portable container 820*c* is suitably positioned inside slot 840*c*, the light beam produced by the light source is reflected from a reflector 854*c* (such as a mirror) accommodated on portable container 820*c*, towards a light detector 852*c* in activation device 810*c*. A detection signal from the light detector may then certify the position of portable container 820*c* inside chamber 842*c*, being thereby configured to allow (e.g. to controller 858) activation of plasma in the portable container. According to some embodiments, activation device 800*c* does not include light source 852*c* whereas portable container 820 comprises a light source 854*c*1, for example a directional light source, energized by a battery (not shown here). Light source 854*c*1 is configured to direct light towards light detector 852*c* when portable container 820*c* is positioned in slot 840*c*.

Figure 9C:
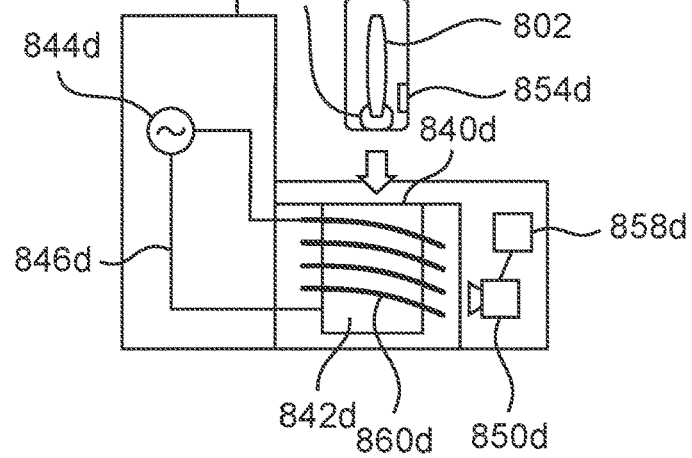
FIG. 9C schematically depicts an exemplary embodiment of the apparatus of FIG. 8A, wherein an identification sticker and an optical reader are used for the certification of the portable container.

FIG. 9C schematically depicts an embodiment of an apparatus 800*d* allowing certifying the validity of a related portable container 820*d* or the position thereof in slot 840*d*, without a transmitter. Portable container 820*d* comprises a code sticker 854*d* whereas activation device 810*d* comprises an optical reader 850*d* configured to read—possibly through a window or an opening in the chamber (not shown here)—a code on the code sticker when portable container 820*d* is suitably positioned inside slot 840*d*. Such reading may be accomplished, in some embodiments, without a dedicated light source using ambient light. According to some embodiments, the portable container 820*d* may comprise a code reader, whereas the activation device 810*d* may comprise a respective code sticker. The code reader may be energized from a battery on the portable container, or through electric contacts of the slot, from an energy source in the activation device.

Figure 9D:
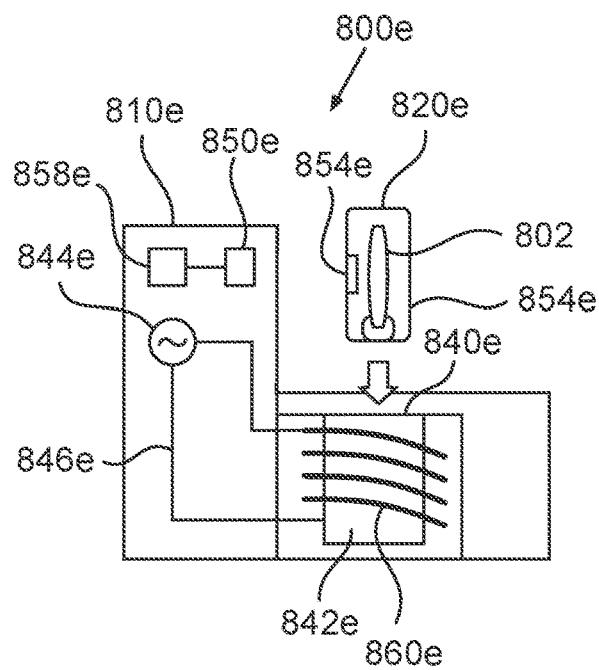
FIG. 9D schematically depicts an exemplary embodiment of the apparatus of FIG. 8A, wherein RFID is used for the certification of the portable container.

FIG. 9D exemplifies an embodiment of an apparatus 800*e* allowing certifying the validity of a related portable container 820*e*, regardless of the portable container's position. Activation device 810*e* comprises an RFID reader 850*e* functionally associated with a controller 858*e*, whereas portable container 820*e* comprises an RFID chip 854*e*. When portable container 820*e* is in the vicinity of activation device 810*e* (but not necessarily in slot 840*e*), RFID reader 850*e* may identify RFID chip 854*e*, thereby identifying the type of portable container 820*e*, and, possibly, certifying the adequacy of a plasma activation protocol to the type of implant inside the portable container. According to some embodiments, RFID chip 854*e* may be activated by a portable energy source of the portable container such as a battery and may transmit RF signal continuously or only when the portable container is inserted into the slot.

Figure 9E:
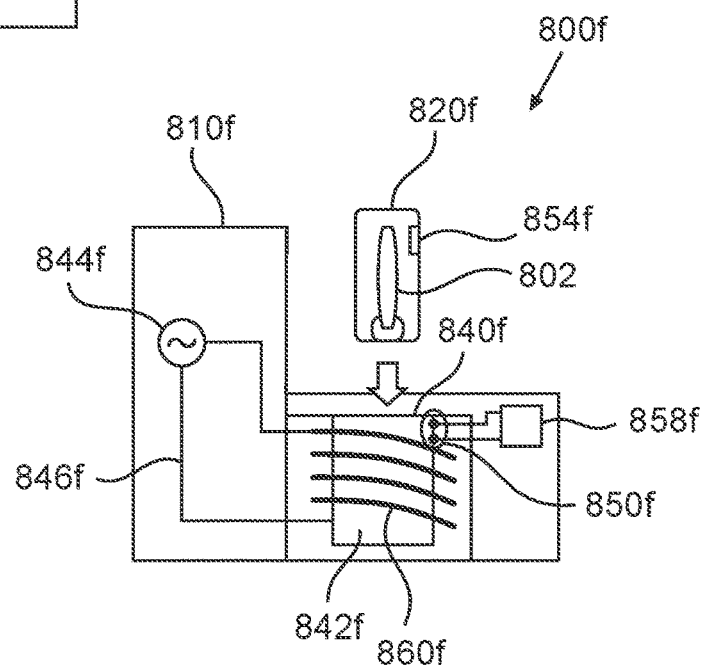
FIG. 9E schematically depicts an exemplary embodiment of the apparatus of FIG. 8A, wherein a data contactor and an identification chip are used for the certification of the portable container.
Figure 9F:
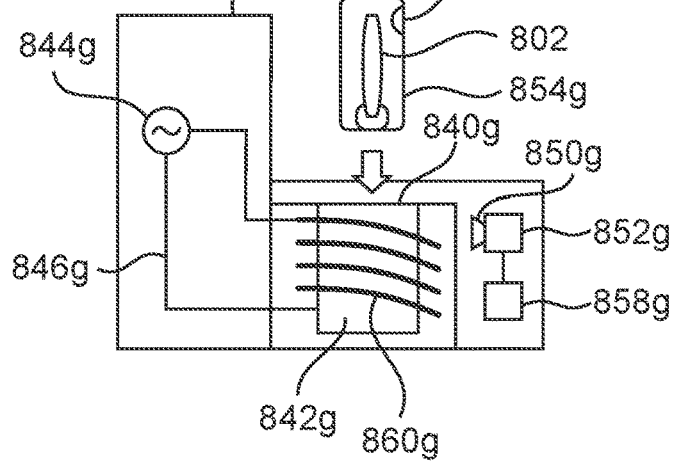
FIG. 9F schematically depicts an exemplary embodiment of the apparatus of FIG. 8A, wherein an optical filter and an optical detector are used for the certification of plasma activation in the portable container.

FIG. 9E exemplifies an embodiment of an apparatus 800*f* allowing certifying both the validity of a related portable container 820*f* and the portable container's position in slot 840*f*. Activation device 810*f* comprises a data contactor 850*f* functionally associated with a controller 858*f*, whereas portable container 820*f* comprises an identification chip 854*f*. When portable container 820*e* is in slot 840*f*, data contactor 850*f* may identify identification chip 854*f*, thereby certifying both the adequate position of the portable container in the slot and identifying the type of portable container 820*f* as explained above. According to some embodiments, the activation device 810*f* may comprise the data contactor whereas the portable container 820*f* may comprise the respective identification chip. The data contactor may be energized from a battery on the portable container, or through electric contacts of the slot, from an energy source in the activation device. FIG. 9F exemplifies an embodiment of an apparatus 800*g* allowing certifying both the position of a portable container 820*g* in slot 840*g*, and also the proper, actual activation of plasma inside the portable container, using a feedback loop. Activation device 810*g* comprises a light detector 852*g*, possibly optically coupled with an optical (e.g. spectral) filter 850*g*. Light detector 852*g* may be functionally associated with a controller 858*g* as described above. Portable container 820*g* comprises a window 854*g* allowing light of the plasma generated inside the portable container to pass through. According to some embodiments, window 854*g* may be optically coupled with an optical filter (e.g. a spectral filter such as a bandpass filter), allowing light having substantially a wavelength of the glare of the plasma generated inside the portable container to selectively pass through the window. Controller 858*g* may be configured according to some embodiments, to receive a signal from light detector 852*g*, certifying that plasma was ignited inside the portable container. Controller 858*g* may be programmed, according to some embodiments, to deactivate power source 844*g* if, for example, a signal is not received from the light detector (signifying that plasma is not ignited inside the portable container) within a pre-determined time period (e.g. 1 second) following activation of apparatus 800*g*.

According to some embodiments two or more field transponders as described hereinabove, may be incorporated in a single portable container. According to some such embodiments a plurality of field transponders (or a structured filed responder, e.g. a mirror sectioned to neighboring portions that alternately reflect and do not reflect) may be used to generate spatially-coded response (e.g. spatially-coded reflections or spatially-coded transmissions) from the portable container. According to some embodiments, spatially-coded response may improve the detection accuracy of the position of the portable container in the slot of the activation device, and/or the validity of the response from the portable container. According to some embodiments field transponders on a same portable container should not necessarily be of a same type. For example, a particular portable container may have an optically reflecting slab, such as a mirror, for establishing position in the slot, and also an RFID chip, for identifying the portable the container and hence the implant stored therein. According to various embodiments, certifying the portable container using a field transponder as is described herein and exemplified in the embodiments of FIGS. 8A, 8B and 9A-9F, may be employed in various apparatuses described here. Specifically, activation devices 110, 210, 410 and 510 of apparatuses 100, 200, 400 and 500 may be equipped with a transmitter and/or a receiver according to the teachings herein. Furthermore, portable containers 120, 120*c*, 220, 220*b*-220*d*, 300, 420, 600, 650 and 680 may be equipped with a field transponder (corresponding to a receiver equipped in the respective activation device), for certifying the portable container according the teachings herein.

Portable Container for a Breast Implant

Augmentation mammoplasty involving the surgical implantation or emplacements of breast implants have a significant complication rate, involving for example a capsule contraction rate of up to 30%. Capsule contraction is believed to be promoted by infection at the implant site and around the implant. Plasma activation of the implant surface prior to the medical operation may be effectively employed to reduce risk of contamination, as is taught and demonstrated herein, for example by enhancing hydrophilicity of the surface of the implant and thereby enhancing adhesion to the implant of antimicrobial liquids (such as antibiotics and antiseptic liquids) e.g. following submersion or wetting of the implant in the antimicrobial liquids before implantation. Plasma activation of the implant surface may also directly reduce the likelihood of bacteria colonialization on the implant. Improved hydrophilicity of the implant after plasma activation may also improve body tissue adhesion to the implant, thereby reducing the likelihood of capsule contraction.

Figure 10A:
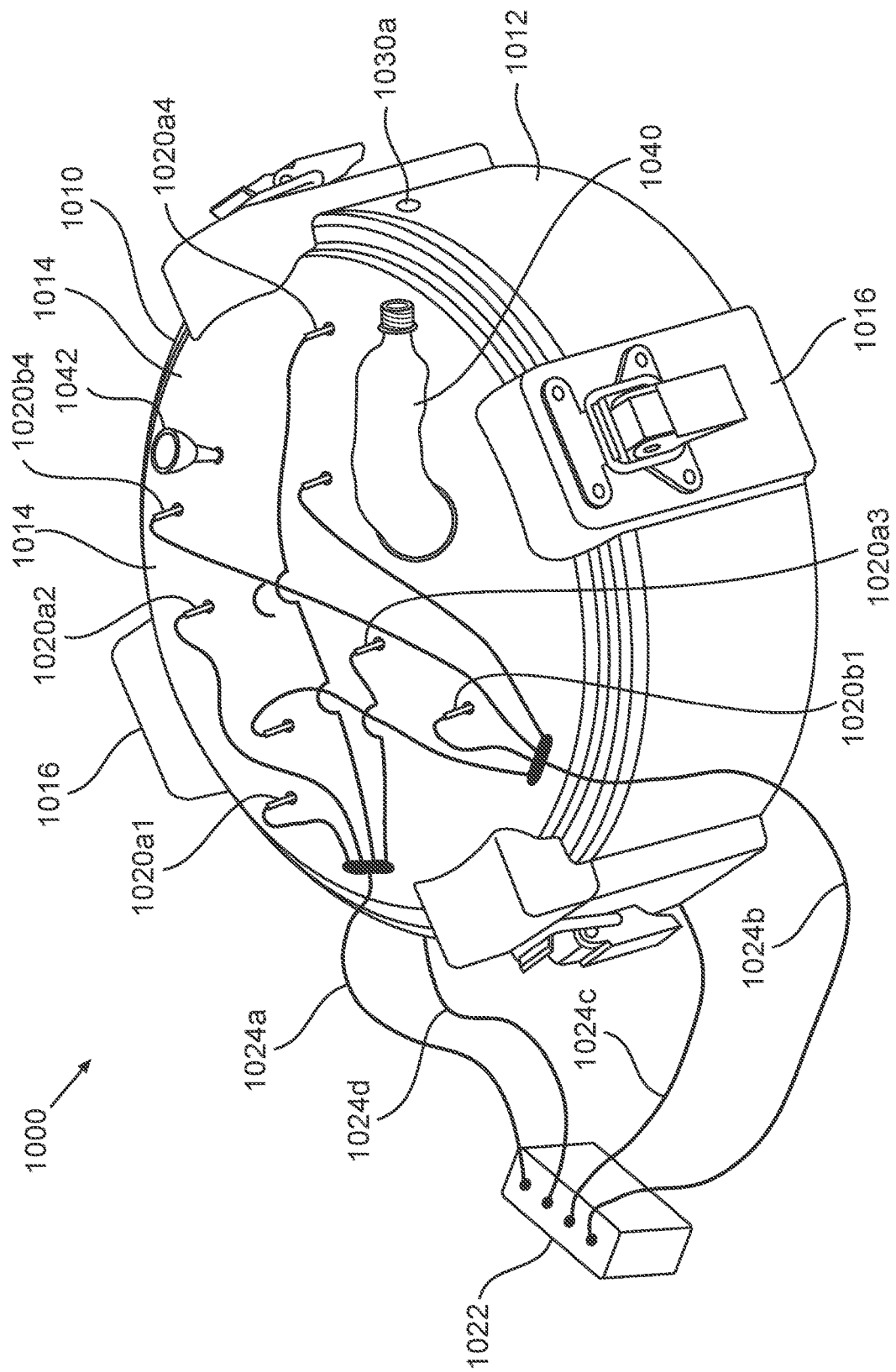
FIG. 10A schematically depicts an embodiment of a container having a compartment, configured for enabling providing plasma treatment to a breast implant therein.

FIG. 10A schematically depicts an embodiment of a container 1000 configured for enabling providing plasma treatment to a breast implant. The breast implant may comprise a silicone shell, such as in a "silicone implant" (which is typically filled with silicone gel) or as in a "saline implant" (which is typically filled with saline). According to some embodiments the plasma treatment may be provided in a clinic where a medical procedure such as an augmentation mammoplasty involving the surgical implantation or emplacement of the breast implant is intended to be carried out. According to some embodiments, the plasma treatment may be provided to the implant prior to such a medical procedure, e.g. less than 48 hours or even less than 24 hours before the surgery. According to some embodiments, the plasma treatment may be provided to the implant just prior to such a medical procedure, namely on the same day of the surgery e.g. less than six hours before the medical procedure and preferably less than one hour before the surgery. It is noted that beneficial effects of the plasma treatment decay, fade away and disappear gradually following the plasma treatment hence it is advantageous to shorten the time between the plasma treatment and the implantation.

According to some embodiments the plasma treatment may be employed to render the implant hydrophilic, thereby considerably improving wettability of an external surface of the implant which has been exposed to the plasma treatment. According to some such embodiments, the container may enable wetting the implant, e.g. with an antimicrobial liquid, after the plasma treatment and prior to removing the implant from the container and installing the implant in a subject.

Container 1000 comprises a compartment 1010 configured to house the implant therein (the implant is not shown here), during plasma activation. According to some embodiments compartment 1010 may be shaped to have an internal space of a hollow dome, dimensioned to contain therein the breast implant. The breast implant may be made as a soft lump e.g. of an elastomer, for example a silicone shell filled with silicone gel or with saline composition. Compartment 1010 comprises a compartment base 1012 and a compartment cover 1014. Compartment 1010 further comprises locks 1016 configured to close and lock compartment cover 1014 to compartment base 1012 when locks 1016 are locked, and to allow opening compartment 1010 by lifting cover 1014 relative to base 1012 when at least three of the locks 1016 are open.

Container 1000 further comprises electrodes 1020, positioned on compartment cover 1014 and on compartment base 1012. Electrodes 1020 are grouped in electrodes groups 1020*a*, 1020*b* 1020*c* and 1020*d*, wherein the electrodes in each electrodes group are electrically interconnected to one another. Each electrodes group includes four electrodes. Electrodes group 1020*a* comprises electrodes 1020*a*1, 1020*a*2, 1020*a*3 and 1020*a*4, electrodes group 1020*b* comprises electrodes 1020*b*1, 1020*b*2, 1020*b*3 and 1020*b*4, and so on to electrodes groups 1020*c* and 1020*d*. The electrodes of electrodes groups 1020*a* and 1020*b* are positioned on cover 1014, whereas the electrodes of electrodes groups 1020*c* and 1020*d* (not shown here) are positioned in base 1012.

The electrodes 1020 are wired to a connector 1022 through wires 1024. All the electrodes in a single electrodes group are electrically connected to a single electric wire, i.e. electrodes group 1020a is connected to wire 1024a, electrodes group 1020b is connected to wire 1024b and so on. Electrodes 1020 may be supplied with an electric power suitable for producing a plasma-generating electric field near the electrodes, by connecting a suitable power source (e.g. a high voltage, high-frequency power source) to the wires 1024. According to some embodiments, switching the electric power supply to the electrodes may be applied so that electric power is supplied through connector 1022 to wires 1024a, 1024b, 1024c and 1024d successively, so that the electrodes in electrodes groups 1020a, 1020b, 1020c and 1020d, respectively are supplied successively with an electric power. Electric power suitable for producing plasma-generating electric field may be, according to some embodiments, supplied at a high voltage, e.g. a voltage of a few hundreds or even a few thousands of Volts. Accordingly, connector 1022, wires 1024 and electrodes 1020, are suitably isolated (e.g. coated with a suitable electrical isolation) for high voltage to prevent arcing or accidental electrifying of a user.

It should be understood that grouping of electrodes to groups of electrodes wherein the groups are electrically distinguished and substantially isolated from each other, and the electrodes in each group are interconnected to one another, as described above and is further detailed below, is provided herein as an exemplary embodiment. Various other electrical arrangements of the electrodes are contemplated, including, for example, a single electrode on the cover and a single electrode on the base; or a multitude of electrodes on the base and on the cover, where the electrodes on the base are grouped (interconnected) together and the electrodes on the cover are grouped (interconnected) together and the electrodes groups of the cover and of the base are electrically disconnected from each other; or a multitude of electrodes on the base and on the cover wherein each electrode is electrically disconnected from the other electrodes and therefore being configured to be activated separately; and so on.

Selecting a specific configuration of the electrodes and the electrodes grouping to electrodes groups may be affected by several considerations. One consideration is the spatial extent, on a surface of the treated implant, of plasma generation by a single electrode. The wider the spatial extent of the useful generated plasma by a single electrode, the smaller the number of electrodes that may be necessary to cover the whole implant by an effective treatment. The spatial extent, in turn, may also be dependent on various factors e.g. geometrical factors such as the distance between the electrode and the implant, the shape of the electrode and the local shape of the implant, electrical factors such as the intensity of the plasma-generating electric field and ambient conditions such as the content and pressure of the gas around the implant. Another consideration is power consumption, namely the total power that may be provided by the electric power source. Generally, the higher the power generated by the power source, the more electrodes that can be supplied with electric power simultaneously. However, supplying a high power may result in disadvantages of significantly more expensive components, more complex excess heat removal from the power source, and a physically larger power source. A related consideration to the power consumption is heat that may develop in the implant and around the implant, whereas rise of temperature of the implant must be kept very limited. A further consideration is mutual interaction between close electrodes: in some embodiments, and in some modes of operation, simultaneous activation of closely-spaced electrodes results in a decrease of the spatial extent of the plasma and a decrease in the useful effect of the plasma generated by the electrodes. The spatial arrangement of the electrodes 1020 and the grouping of the electrodes to electrodes groups in container 1000 exemplifies a particular embodiment of such considerations, wherein a total of eight electrodes are used to effectively generate plasma over one side (the top or the bottom) of the breast implant. The eight electrodes on each side are grouped to two electrodes groups, each consisting of four electrodes, and the four electrodes of each group are widely spaced over the surface of a side (top or bottom) of the implant, and interleaved by the electrodes of the other group, to minimize mutual interaction between simultaneously activated electrodes.

According to some embodiments plasma generation inside container 1000 may be assisted or facilitated by an ignition field, generated by an initial high voltage ignition pulse. Such an ignition field may be configured to generate inside the closed compartment initial conditions—specifically, for example, to increase concentration of ionized molecules in the gas or ionized species on internal surfaces of the compartment of the container—so as to enable generation of plasma using a lower (RF) voltage supplied to electrodes 1020. According to some embodiments, an ignition electric pulse at a voltage higher than 10 KV and possibly higher than 100 KV can be supplied. According to some embodiments an initial high voltage pulse may facilitate plasma generation at a plasma generating field effected by a voltage lower than 5 KV, and preferably lower than 1 KV or even lower than 500V (which is supplied to electrodes 1020). According to some embodiments, the ignition field generated by the high voltage ignition pulse is configured to effect arcing inside the compartment (whereas the plasma generating field is configured to avoid arcing).

Figure 10B:
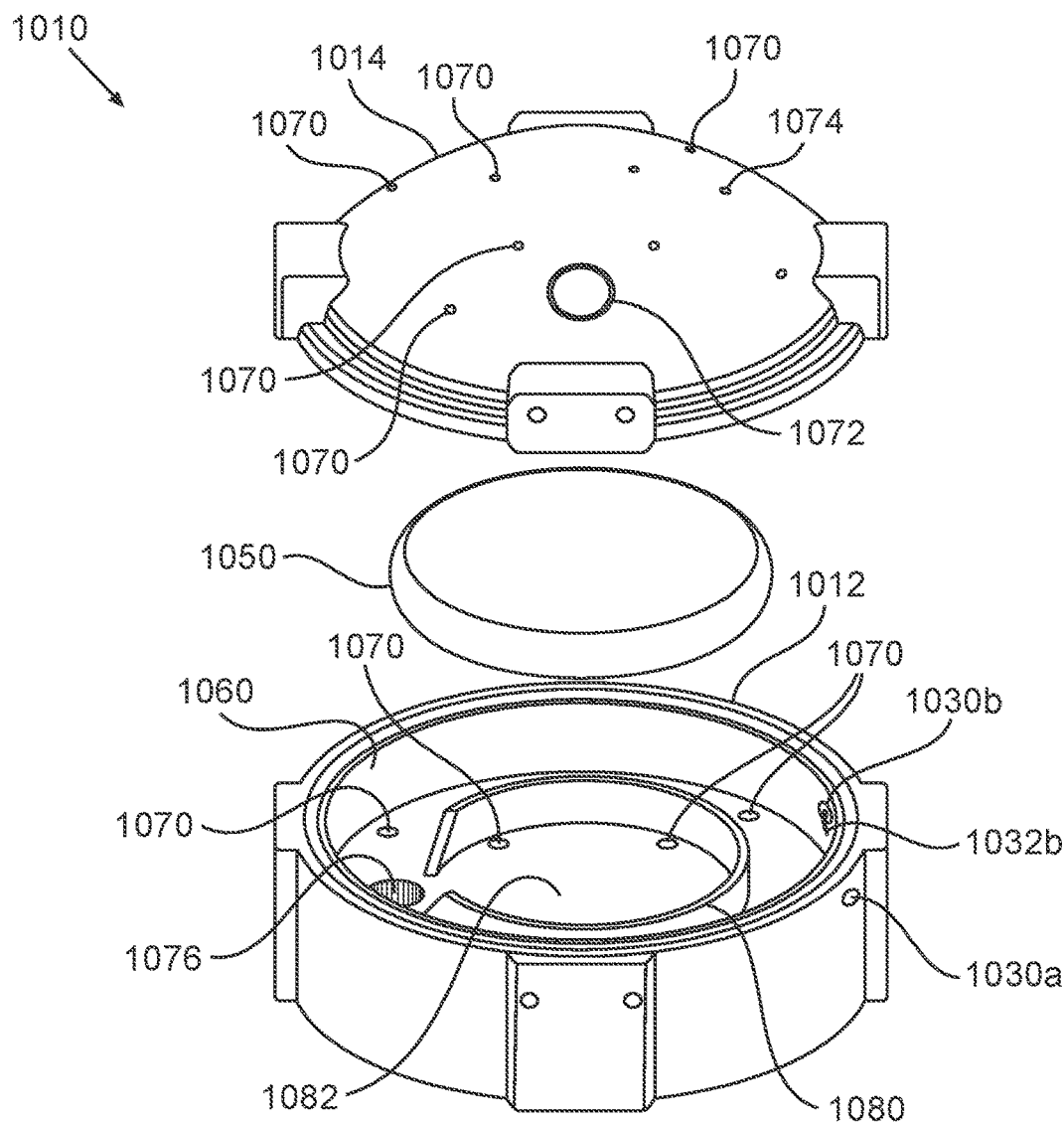
FIG. 10B schematically depicts the compartment of the container of FIG. 10A in a semi-exploded view.

Thus, according to some embodiments container 1000 further comprises at least one, and preferably two, high voltage vacuum feedthroughs 1030a and 1030b (shown in FIG. 10B). Each high-voltage vacuum feedthrough 1030a and 1030b allows conducting a high voltage from the outside of compartment 1010 to ignition electrodes 1032a and 1032b (shown in FIG. 10B), respectively positioned, preferably, inside the compartment. By connecting HV cables to feedthroughs 1030a and 1030b, respectively, high voltage may be supplied between the two ignition electrodes 1032a and 1032b positioned inside compartment 1010, and particularly an ignition pulse may be supplied to the interior of compartment 1010 through the feedthroughs. It is emphasized that high voltage vacuum feedthroughs 1030a and 1030b are configured to withstand a pressure difference between the interior of compartment 1010 and ambient atmosphere outside the compartment, thereby preventing gas leaks through the feedthroughs and assisting in maintaining a gaseous mixture (possibly different form ambient atmosphere) having desired pressure and composition thereinside.

According to some embodiments, container 1000 may further comprise a gas port 1040 configured to fluidly connect to a gas source such as a portable gas reservoir, or to a tube or a pipe connected to a gas reservoir. Thus container 1000 may be transported or shipped or stored with the implant housed inside compartment 1010 at ambient conditions (atmospheric pressure and composition), and then be adapted for plasma generation therein by flushing the compartment with easily-ionisable gas such as Argon as explained above. A portable gas reservoir (not shown here) containing between about 5 cc to about 300 cc of gas, at a pressure of about 100-200 Atm, may be used to flush the compartment with an ionisable gas prior to activating the electric power. Gas port 1040 is positioned on cover 1014 and provides fluid communication to an interior of compartment 1010 for flushing the interior of compartment 1010 with a gas from the gas source. Alternatively or additionally, gas port 1040 may be fluidly connected to a gas pump or a tube or a pipe connected to a gas pump, thereby enabling pumping the interior of compartment 1010 by the gas pump for facilitating plasma generation in low-pressure air.

Container 1000 further comprises a liquid port 1042 positioned on cover 1014 and being configured to provide fluid communication to the interior of compartment 1010. Liquid port 1042 is configured to enable injecting a fluid such as an antimicrobial liquid into compartment 1010 for rinsing or wetting the implant therein after a plasma treatment. Liquid port 1042 is normally closed or sealed thereby sealing the interior of compartment 1010 and preventing spontaneous entering of foreign substances such as gas or contaminants into the compartment, and also preventing leakage of gas out of the compartment. After the plasma treatment and for enabling injecting the fluid into the compartment through the liquid port, the liquid port may be opened or the seal thereof may be controllably broken. According to some embodiments, liquid port 1042 may be equipped with a breakable seal such as a foil of Mylar or Kapton or a metal foil for example, which may be punctured by a syringe needle. Thus, for rinsing the implant by a desired liquid through liquid port 1042, a syringe having a syringe needle and containing the desired liquid may be advanced through liquid port 1042 until the breakable seal is punctured by the needle, and then the syringe may be employed to inject the liquid into the compartment to spray or to rinse or to wet the implant or to fill the interior of the compartment so that the implant is immersed in the fluid.

FIG. 10B schematically depicts compartment 1010 in a semi-exploded view. Portions of the locks 1016 are omitted from the Figure for the sake of clarity. An implant 1050 may be disposed in the interior 1060 of compartment 1010, between base 1012 and cover 1014, for plasma treating the implant during use. Cover 1014 comprises several electrode houses 1070 shaped as through-holes, for housing several electrodes 1020, respectively, which are located on the cover, as is further detailed below. Cover 1014 further comprises an inlet hole 1072 for gas port 1040. Cover 1014 further comprises a bio-hole 1074 for liquid port 1042.

Base 1012 also comprises several electrode houses 1070 for housing the electrodes, respectively that are positioned on the base. Base 1012 further comprises an escape port 1076 for enabling escape of pressurized gas from the interior 1060 outwards from compartment 1010. Thus, if an ionisable gas such as Argon is driven through gas port 1040 into interior 1060 of compartment 1010 (which initially contains e.g. air), the excess of gas (the mixture of air and Argon) may escape outwards through escape port 1076, leaving the interior substantially filled with the ionisable gas, substantially at atmospheric pressure.

Base 1012 further comprises a spacer 1080 protruding above a floor 1082 of base 1012 towards cover 1014. Spacer 1080 is thereby configured to support implant 1050 above floor 1082 and distanced from electrodes 1070 when implant 1050 is supported inside compartment 1010, thereby establishing a free space underneath the implant where plasma may be formed. Spacer 1080 is shaped as a partially open C-ring so that fluid connectivity is maintained between the interior of the ring and the exterior thereof, even when implant 1050 is supported on spacer 1080. Thus, when the interior 1060 of compartment 1010 is flushed with an ionisable gas, the interior of the C-shaped spacer may also be ventilated with the ionisable gas though the opening of the C, thereby facilitating plasma ignition inside the ring. It should be understood however that various other arrangements may be employed to support implant 1050 distanced from the floor 1082, such as a multitude of thin pillars arranged between the implant and the floor or a thin net stretched above floor 1082 configured to support the implant, or the like.

Figure 11:
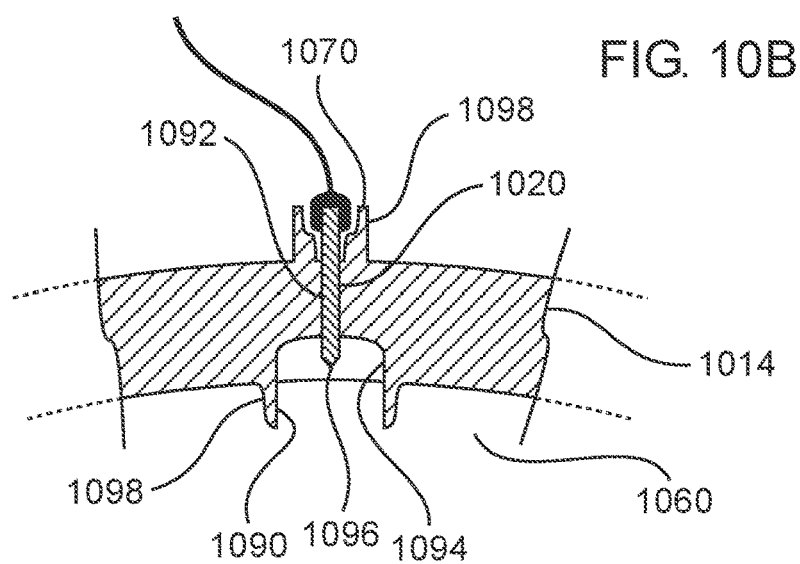
FIG. 11 schematically depicts a cross section of an electrode house in a cover of the compartment of FIGS. 10A and 10B, housing an electrode therein.

FIG. 11 schematically depicts a cross section of electrode house 1070 in cover 1014, housing an electrode 1020 therein (the electrode houses in base 1012 are shaped similarly, mutatis mutandis). Electrode house 1070 is shaped as a through hole through cover 1014, having a relatively narrow external section 1092 and a wider internal section defining a hollow cavity 1094 in a portion thereof bordering the interior 1060. Electrode 2020 is shaped as a needle, fitting in dimension to the narrow portion 1092 of electrode house 1070 so that narrow section 1092 is sealed when the electrode 1020 is disposed therein. Electrode 1020 is further shaped to have a tip 1096 positioned inside the hollow cavity 1094 of electrode house 1070. According to some embodiments the tip 10967 may be blunt. According to some embodiments the tip 1096 may be pointed. Electrode house 1070 may further comprise an isolating barrier 1098 extending outwards on an external surface of cover 1014 and extending inwards into the interior 1060 of compartment 1010, to electrically isolate and mechanically protect portions of electrode 1020 protruding from cover 1014, and to protect the implant from the tip 1096.

Power Source for Plasma-Generating Electric Field

Figure 12A:
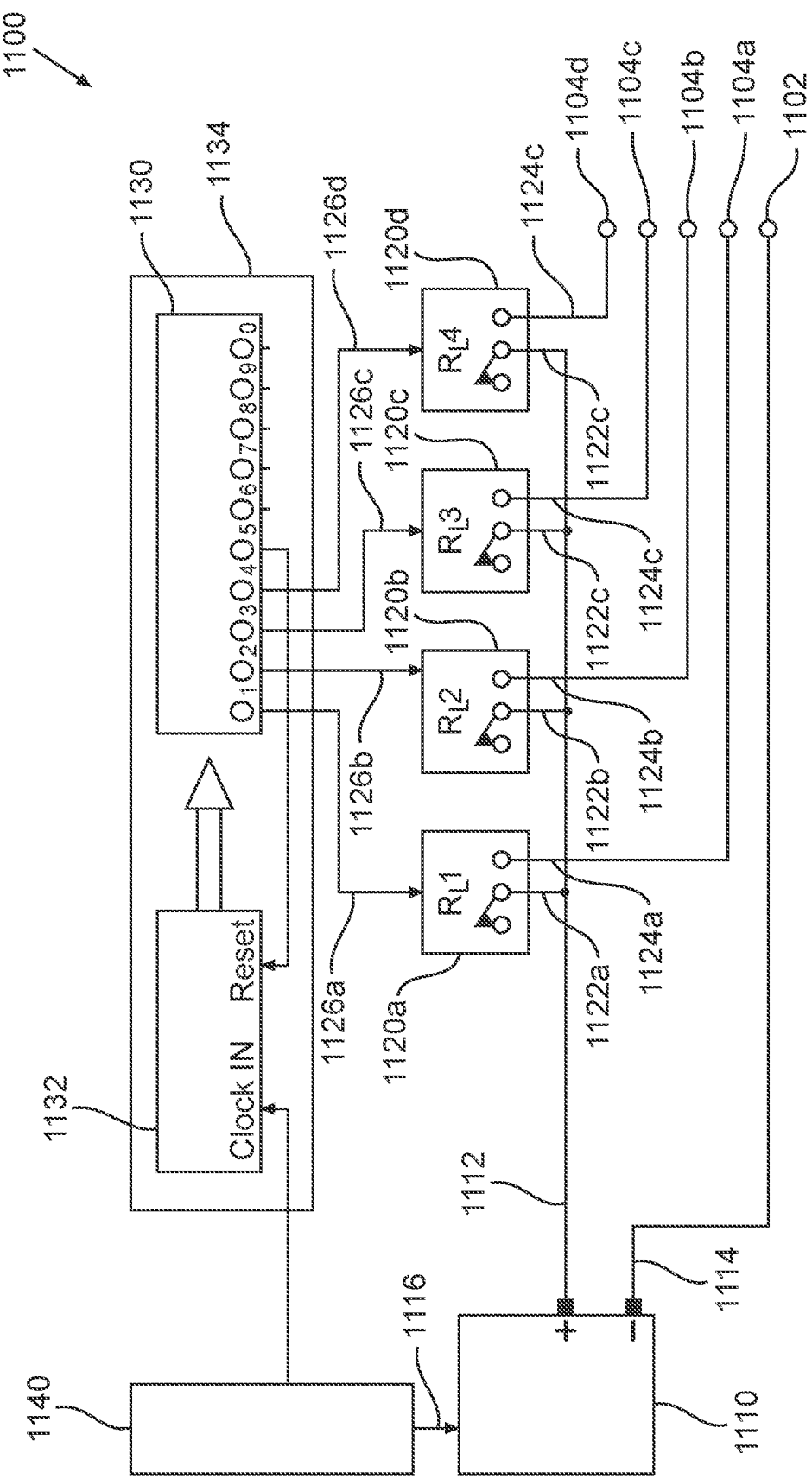
FIG. 12A schematically depicts an embodiment of an electrical circuit configured to generate electric power suitable to produce a plasma-generating electric field in the container of FIG. 10A.

FIG. 12A schematically depicts an embodiment of an electrical circuit 1100 configured to generate electric power—e.g. power at a high voltage and high frequency—suitable to produce a plasma-generating electric field in container 1000. Electrical circuit 1100 is configured to provide electric power to the electrodes groups 1020a-1020d in a successive manner, so that the electrodes groups receive electric power one after the other, and the electrodes of only one electrodes group receive electric power at a time. Electrical circuit 1100 comprises a common electrode output 1102 and four high voltage outputs 1104, namely high voltage outputs 1104a, 1104b, 1104c and 1104d, respectively. Electrical circuit 1100 is configured to generate a high voltage, high frequency signal (suitable for producing a plasma generating electric field when supplied to associated electrodes) and successively switch the high voltage, high frequency signal to the four high voltage outputs 1104a-1104d (corresponding to the four electrodes groups 1020a-1020d) so that a high-voltage high frequency signal is produced successively between each of the high voltage outputs 1104 and the common electrode output 1102.

Electrical circuit 1100 comprises a high-voltage power generator 1110. High-voltage power generator 1110 is configured to generate a high-voltage, high frequency signal between a high output terminal 1112 and a low output terminal 1114. High-voltage power generator 1110 is further configured to generate the high-voltage, high frequency signal according to a pre-determined scheme and according to signal parameters which are supplied to the high-voltage power generator 1110 in an input terminal 1116. According to some embodiments the high-voltage, high frequency signal may have a voltage between 100-500V or between 250-1000V or between 500-2000V or between 1 KV-10 KV or between 10 KV-20 KV or even between about 20 KV-100 KV. According to some embodiments the high-voltage, high frequency signal may have a frequency in the range between 100 KHz-100 GHz. According to the some embodiments, the high-voltage, high frequency signal may be modulated, for example pulse modulated as is further exemplified below.

Electrical circuit 1100 further comprises four high-voltage switches 1120—namely high-voltage switches 1120a, 1120b, 1120c and 1120d, respectively. Each high-voltage switch 1120 comprises a switch input terminal 1122, electrically associated with high output terminal 1112. Each high-voltage switch 1120 further comprises a switch output terminal 1124 selectively electrically associated with one of the high voltage outputs 1104, so that switch output terminal 1124a is electrically associated with high voltage output 1104a, switch output terminal 1124b is electrically associated with high voltage output 1104b and so on. Each high-voltage switch 1120 further comprises a switch command terminal 1126. Each high voltage switch 1120 is configured to switch—that is to say to connect or to disconnect—the high voltage, high frequency signal between the switch input terminal 1122 and the switch output terminal 1124, according to a command signal provided on the switch command terminal 1126.

Electrical circuit 1100 further comprises a switch controller 1130, selectively electrically associated with switch command terminals 1126a-1126d. Switch controller 1130 is configured to command successively high-voltage switches 1120a-1120d to switch the high voltage high frequency signal to the high voltage outputs 1104a-1104d, respectively. According to some embodiments switch controller 1130 comprises a decade counter 1132, feeding a 1-of-10 decoder/driver 1134, to generate suitable command signals to the high voltage switches 1120 from an input clock signal. Four outputs of 1-of-10 decoder/driver 1134, namely O1-O4, are respectively connected to switch command terminals 1126a-1126d, whereas a reset signal from a fifth output O5 of 1-of-10 decoder/driver 1134 is connected to a reset input of decade counter 1132 for producing successive sequential command signals to switch command terminals 1126a-1126d, as is well known in the art.

Electrical circuit 1100 further comprises a controller 1140 such as a CPLD, configured to control high voltage power source 1110 and switch controller 1130. Controller 1140 feeds switch controller 1130 with a timing signal such as a clock signal for determining the timing of the successive switching of the high voltage high frequency signal to the high voltage outputs 1104. Controller 1140 further controls high voltage power source 1110 for determining parameters of the high voltage high frequency signal such as the voltage and frequency of the signal and possible modulation parameters such as pulses parameters and timings, such as pulse width (PW) and pulse repetition rate (PRF).

Figure 12B:
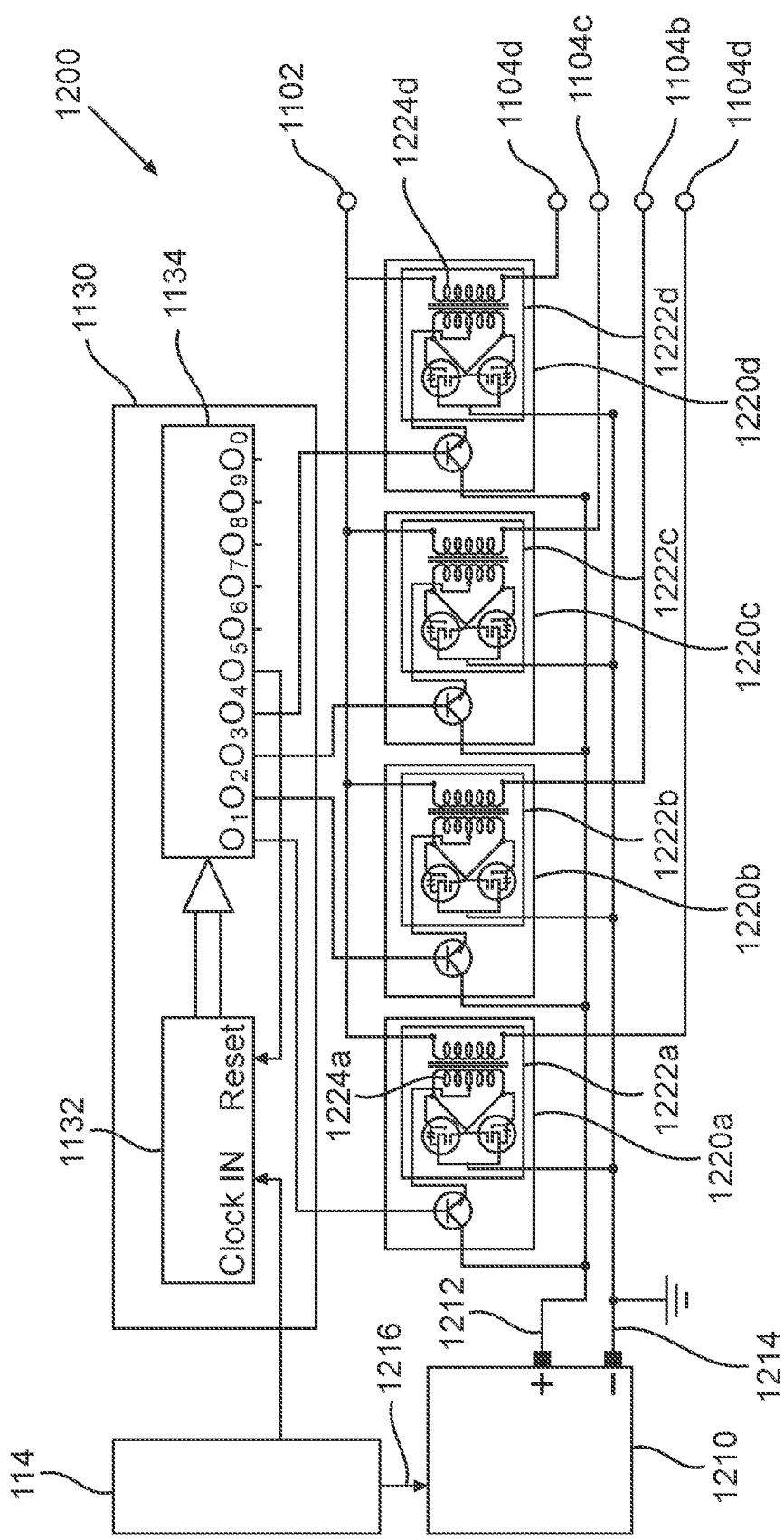
FIG. 12B schematically depicts an embodiment of another electrical circuit configured to generate electric power suitable to produce a plasma-generating electric field in the container of FIG. 10A.

According to some embodiments an electrical circuit 1200, depicted schematically in FIG. 12B, may be employed as a power source for providing electric power suitable for producing a plasma-generating electric field in container 1000. Electrical circuit 1200 is different from electrical circuit 1100 in that a high voltage high frequency signal is separately generated in one of four high voltage power sources 1220 wherein each high voltage power source 1220 comprises an oscillator 1222 comprising a step-up transformer 1224 (e.g. a 1:90 step-up transformer) and is configured to be exclusively electrically associated with one electrodes group (e.g. voltage power source 1220a is configured to be electrically associated with electrodes group 1020a via high voltage output 1104a, voltage power source 1220b is configured to be electrically associated with electrodes group 1020b via high voltage output 1104b and so on). Thus, electrical circuit 1200 avoids the use of possibly complex and expensive high voltage switches as employed in electrical circuit 1100, yet requires four high voltage power sources instead of a single high voltage power source in electrical circuit 1100. A further possible advantage of electrical circuit 1200 over electrical circuit 1100 is that each high-voltage power source 1220 resonates in a resonance frequency determined, inter alia, by the load of the high-voltage power source. In other words, each high-voltage power source 1220 may spontaneously tune to a resonance frequency, thereby affecting an optimum power delivery to the electrodes of the container and hence optimum plasma generation, thereby rendering a step of impedance matching redundant.

The high voltage power sources 1220 are supplied with a low voltage, high current power supply from a low voltage power source 1210. For generating plasma around implant 1050 in container 1000, using a power source such as electric circuit 1100 or electric circuit 1200, high voltage outputs 1104 are electrically selectively connected to wires 1024 so that high voltage output 1104a is electrically connected to wire 1024a, high voltage output 1104b is electrically connected to wire 1024b and so on, possibly using high-voltage connector 1022. Common electrode output 1102 is electrically connected to a common (reference) electrode (not shown in the Figures) which is positioned proximal to implant 1050. The common electrode may be shaped as a conducting plate such as a metal plate positioned under container 1000 during the activation of the cover electrodes (electrodes groups 1020a and 1020b), and above the container during activation of the base electrodes (electrodes groups 1020c and 1020d). Additionally or alternatively, electrodes groups 1020c and 1020d may be employed together (i.e. being electrically interconnected) as a common electrode when high voltage is supplied to electrodes groups 1020a and 1020b and, likewise, electrodes groups 1020a and 1020b may be employed together, being electrically interconnected, as a common electrode, when high voltage is supplied to electrodes groups 1020c and 1020d. In other words, according to some embodiments, the use of a dedicated common electrode may be avoided. Further, according to some embodiments, particularly in variants of electrical circuit 1200, both outputs of each high voltage power source 1220 are selectively electrically connected to a pair of electrodes in container 1000, namely one electrode on cover compartment 1014 and one electrode on compartment base 1012. Thus, sequentially alternating the operation of high voltage power sources 1220 may affect a plasma-generating electric field between alternating pairs of electrode, thereby generating plasma within the compartment (and avoiding the use of a dedicated common electrode).

Figure 12C:
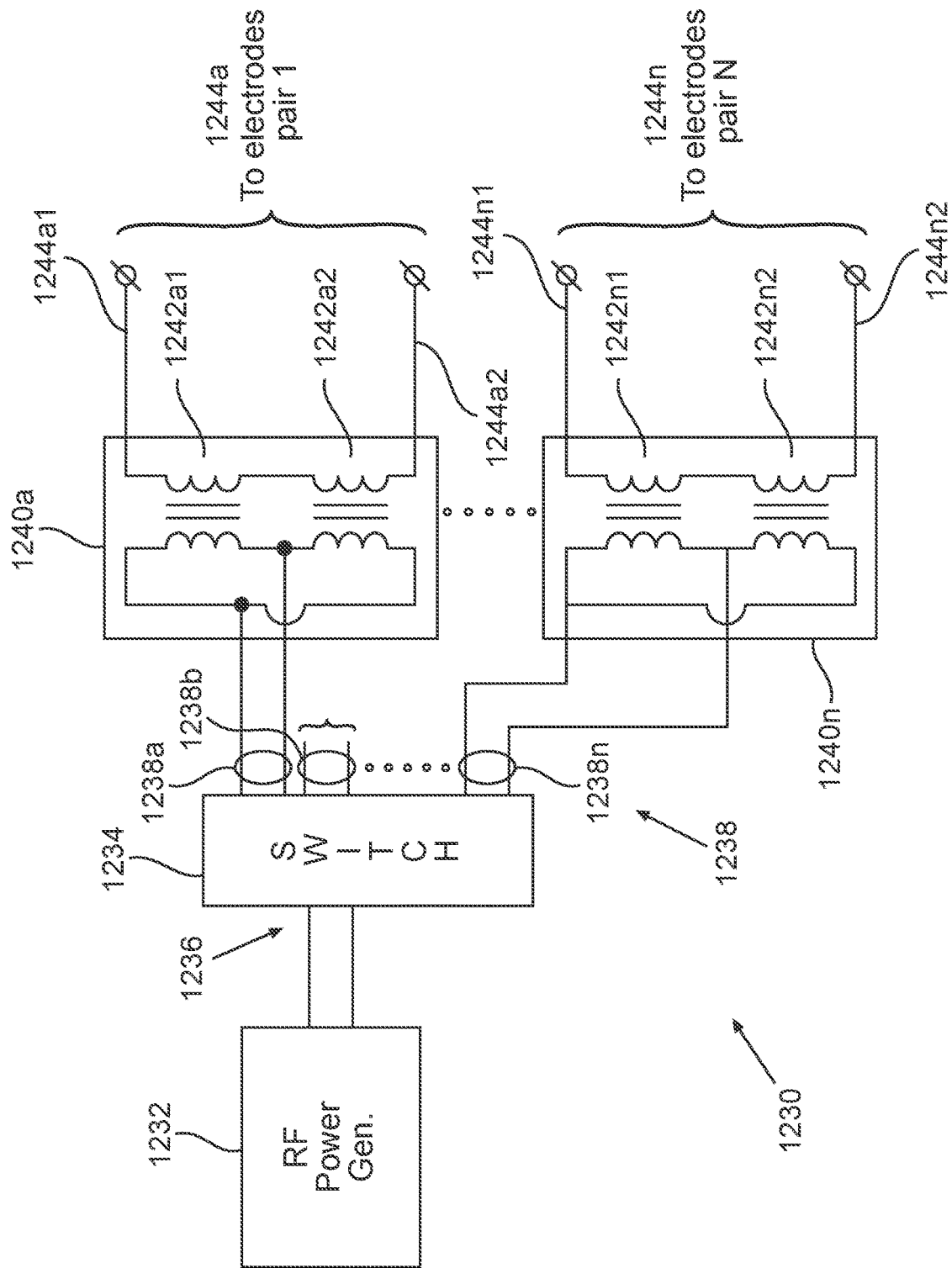
FIG. 12C schematically depicts an embodiment of yet another electrical circuit configured to generate electric power suitable to produce a plasma-generating electric field in a container or a plasma chamber of the invention, between electrodes of selected pairs, while sequentially switching the supply between the electrodes pairs.

FIG. 12C schematically depicts an embodiments of yet another electrical circuit 1230 configured to generate electric power suitable to produce a plasma-generating electric field in a container or a plasma chamber (not shown here) for plasma-treating a breast implant. More particularly, electrical circuit 1230 is configured to apply a plasma-generating RF electric field between electrodes of selected pairs, while sequentially switching the supply between the electrodes pairs. In other words, electrical circuit 1230 may sequentially distribute the electric power to various electrodes pairs such that at any instant only a single pair is supplied with electric power. According to variant embodiments of electrical circuit 1230, several pairs of electrodes may simultaneously be supplied with electric power. According to some variant embodiments of electrical circuit 1230, sequential distribution of electric power to the electrodes pairs may be interleaved with time intervals wherein no electric power is supplied, as is exemplified in FIG. 14 herein below.

An exemplary container (not shown here) suitable for use with electric circuit 1230 may have a compartment such as compartment 1010 of container 1000. The container may further be different from container 1000 in that all the electrodes of the container are electrically disconnected from one another. According to this embodiment, power is supplied, sequentially, to single electrodes pairs, one pair after the other, wherein each electrodes pair consists of one electrode in the bottom of the compartment (on compartment base 1012) and one electrode in the top of the compartment (on compartment cover 1014).

Electrical circuit 1230 comprises a high-current, low-voltage RF power generator 1232 and an RF switch 1234 electrically associated with RF power generator 1232 via input pair leads 1236. RF switch 1234 is configured and operable to divert electric power supplied to input pair leads 1236 to one (or, according to some embodiments, more than one) output pair lead 1238—e.g. to output pair lead 1238a or to output pair lead 1238b and so on. RF switch 1234 may be commanded to so distribute the electric power between the output pair leads by a command input (not shown hear) as is well known in the art.

Electrical circuit 1230 further comprises a multitude of high-voltage power sources 1240, namely power source 1240a to power source 1240n. Each high-voltage power source 1240 is electrically associated with an output pair leads 1238, namely, high-voltage power source 1240a is electrically associated with output pair leads 1238a, high-voltage power source 1240n is electrically associated with an output pair leads 1238n, and so on. Each high-voltage power sources 1240 comprises two step-up transformers 1242a1 and 1242a2, respectively, electrically connected so as to provide on a high voltage output 1244 of the high voltage power source a sum voltage of the output of the two transformers 1242a1 and 1242a2. For providing a plasma-generating electric field to pairs of electrodes, each high-voltage output is electrically associated with one electrodes pair, so that a first lead 1244a1 in high voltage output 1244a is connected to one electrode in electrodes pair 1, and a second lead 1244a2 in high voltage output 1244a is connected to the other electrode in electrodes pair 1.

Figure 13:
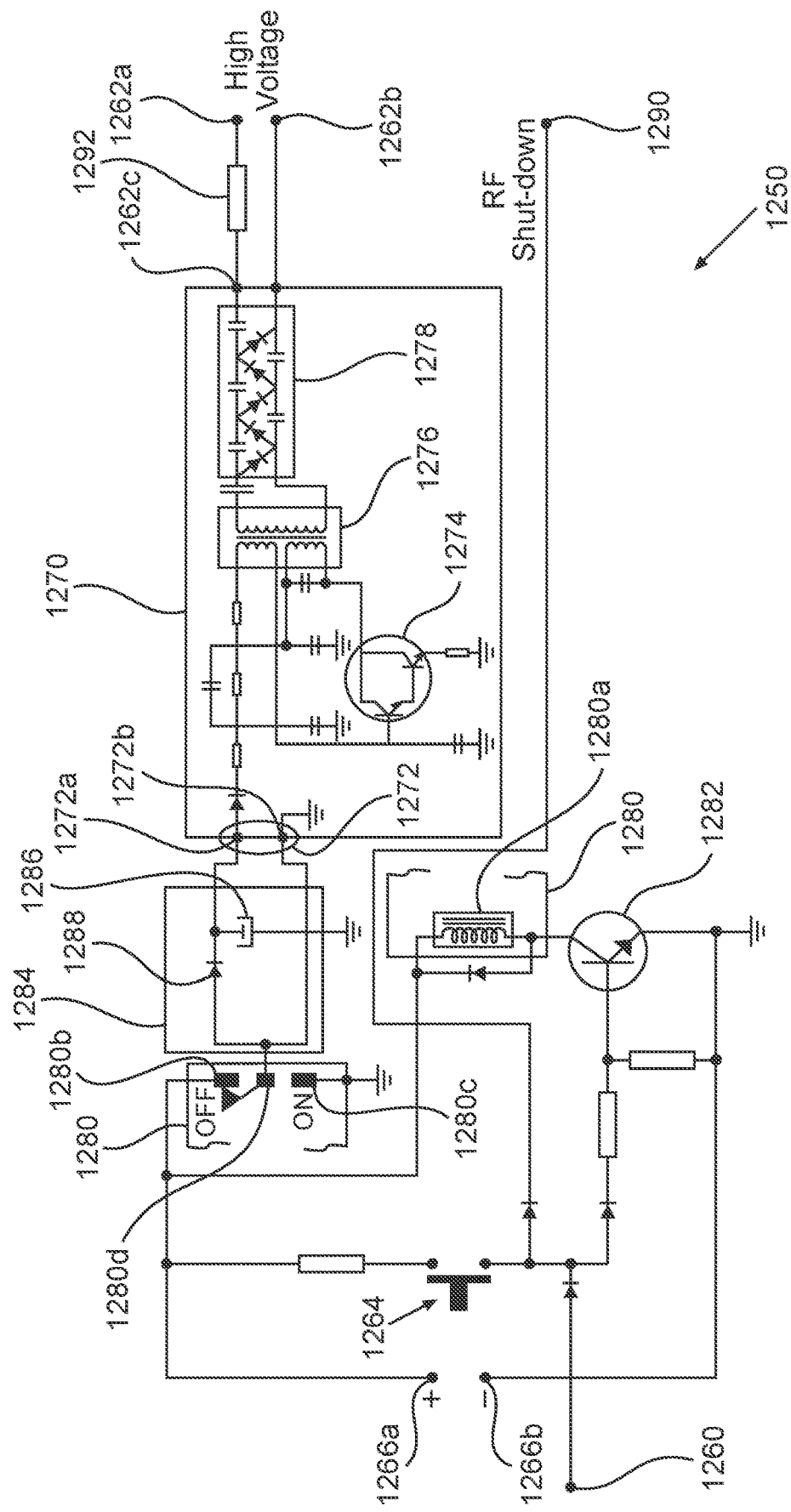
FIG. 13 schematically depicts an embodiment of an initial high voltage pulse generator (HVPG) according to the teachings herein.

FIG. 13 schematically depicts an embodiment of an initial high voltage pulse generator (HVPG) 1250. HVPG 1250 is configured to receive a triggering pulse in input electrode 1260, and to generate as a response a high voltage pulse, having, generally, an amplitude above 1 KV, between output electrodes 1262a and 1262b. HVPG 1250 further comprises a manual-start button 1264 configured to enable a user to generate manually an initial high voltage pulse upon pressing the button. HVPG 1250 is configured to be energized by a 6V/0.5 A DC power source, connected between DC power supply contacts 1266a and 1266b.

HVPG 1250 comprises an igniter 1270 configured to transform a low voltage in an input 1272 thereof to a high voltage over output electrodes 1262c and 1262b. The low voltage in input 1272 may be for example of a few volts or a few tens of volts, e.g. 6V or 12V or 24 volts. The high voltage between output electrodes 1262a and 1262b may be above 1 KV or above 10 KV or even above 100 KV, for example 1.5 KV or 40 KV or even 200 KV. Igniter 1270 may comprise for example an amplification stage 1274 coupled to a step-up transformer 1276, forming together an oscillator. Step-up transformer 1276 may have an effective step-up ratio (secondary to primary turns ratio) of about 800, or a step-up ratio greater than 1000 or even a step-up ratio greater than 5000. A voltage doubler 1278 coupled to the step-up transformer may be used to further increase the output voltage. It should be appreciated by a person skilled in the art that the particular voltage doubler 1278 depicted in FIG. 13 is a ×5 voltage doubler, thereby being configured to multiply the input voltage thereof (the output of step-up transformer 1276) 5 times.

HVPG 1250 further comprises a relay 1280 having an activating coil 1280a connected to a current driver 1282. Relay 1280 further comprises a normally-closed input contact 1280b, a normally-open input contact 1280c and an output contact 1280d which is electrically connected to normally-closed input contact 1280b when coil 1280a is not activated, and to normally-open input contact 1280c when coil 1280a is activated. HVPG 1250 further comprises a pulse energy store 1284 comprising a capacitor 1286 and a diode 1288, functionally associated between output contact 1280d and input 1272 of igniter 1270.

In operation, prior to a generation of an initial high-voltage pulse, capacitor 1286 is charged up from power supply contact 1266 via relay 1280 and via diode 1288. An equal voltage is supplied to both input contacts 1272a and 1272b of igniter 12780, hence igniter 1270 is inactive when capacitor 1286 is being charged or during when it is fully charged.

For generating an initial high-voltage pulse, a start pulse (e.g. a 200 msec pulse width) may be supplied to input electrode 1260, thereby activating current driver 1282 and consequently activating relay 1280. By activating relay 1280, output contact is electrically connected with normally-open input contact 1280c thereby connecting input contact 1272b of igniter 1270 to ground. It is noted that capacitor 1286 may not discharge to ground via diode 1288 and hence discharges via igniter 1270. The capacitor voltage of capacitor 1286 is then transformed into a high voltage pulse between the output contacts 1262c and 1262b of igniter 1270, which lasts until capacitor 1286 is substantially discharged.

An initial high-voltage pulse may additionally or alternatively be generated by pressing manual start button 1264. Pressing manual start button 1264 provides an activating voltage to current driver 1282 causing current driver 1282 to activate relay 1280, and consequently generating an initial high voltage pulse as described above. It is emphasized that the duration of the initial high-voltage pulse is not related to the time during which manual start button 1264 is pressed and is determined, as explained above, by the time it takes to capacitor 1286 to discharge via igniter 1270. According to some embodiments the initial high voltage pulse may endure for a time period in the range from as short as less than 1 micro-second (usec) to as long as more than 1 sec. According to some embodiments the initial high-voltage pulse may be exponentially decaying. According to some embodiments the initial high-voltage pulse width may be between 1 mili-second (ms) to 500 ms. According to some embodiments the initial high-voltage pulse may be about 250 msec long.

HVPG 1250 further comprises a RF shut-down output 1290 for providing an indication on the generation of an initial high voltage pulse, e.g. for allowing forced shut-down of a plasma-generating electric power or for disconnecting a plasma-generating electric power source from electrodes of the container that are subject to such an initial high voltage pulse, as is further described below. It is noted that when a start pulse is supplied to input electrode 1260 and/or when manual start button 1264 is pressed, RF shut down output 1290 receives a positive voltage signal, indicating the concurrent generation of an initial high voltage pulse. According to some embodiments, RF shut down output 1290 may be electrically associated with a control input of a high-voltage switching device (not shown here) connected between a high voltage high frequency power source—such as electrical circuit 1100 or electrical circuit 1200—and container 1000. For example a high voltage high frequency relay (not shown here) may be used to controllably connect or disconnect a high-voltage high frequency power source to electrodes 1020 of container 1000, whereas the high-voltage high frequency relay is commanded by the RF shut down signal provided from RF shut down output 1290 of HVPG 1250. Thus, when an initial high voltage ignition pulse is generated by HVPG 1250, the power source or power sources that feed electrodes 1020 are being disconnected, thereby protecting the high-voltage high frequency power source from being damaged by high-voltage leaks from HVPG 1250 through parasitic conducting paths, e.g. on the container. According to some embodiments, for facilitating plasma ignition and plasma generation in container 1000 (details of such plasma ignition and plasma generation are provided further below), an initial high voltage pulse may be supplied to electrodes of the container. According to some embodiments, an initial high voltage pulse may be supplied between high-voltage electrodes 1032a and 1032b by connecting high voltage cables between, e.g., high-voltage output 1262a of igniter 1270 to feedthrough 1030a, and high-voltage output 1262b to feedthrough 1030b (and activating HVPG 1250 as described above). It is noted that HVPG 1250 further comprises a protection resistor 1292 between output electrode 1262c and output electrode 1262a, for limiting the current that may be supplied through output electrodes 1262.

It should be emphasized that HVPG 1250 may be used for facilitating plasma ignition also in other containers than container 1000 described herein. In other words, the description of operation of HVPG 1250 in conjunction with container 1000 is provided for exemplary and demonstrative purpose and should not be considered limiting. According to some exemplary embodiments HVPG 1250 may be used for facilitating plasma ignition in containers for dental implants of in containers storing inside biological material or in containers storing orthopedic implants or in containers intended for storing any object or article intended to be installed or implanted in a subject's body. According to some embodiments an initial high voltage pulse as described herein may be successfully applied to facilitate later plasma ignition between electrodes that are positioned outside the space where plasma is to be activated. In other words, according to some embodiments the two (or more) electrodes for applying the initial high voltage pulse may be arranged outside a closed compartment or a sealed compartment (the compartment may be made, partially or wholly, of dielectric materials), being thereby detached and electrically isolated from the gas inside the compartment which is to be excited to plasma. According to some embodiments, the container for storing the implant may comprise an external capsule housing an internal capsule which houses the implant, and the electrodes for applying the initial high-voltage pulse may be arranged outside the external capsule. According to some embodiments, such electrodes may be arranged inside the external capsule and outside the internal capsule, or may be arranged inside the internal capsule, or may be arranged such that a first electrode is arranged inside or outside any of the capsules, whereas a second electrode is arranged inside or outside any of the capsules, independently and irrespectively of the first electrode.

Figure 14:
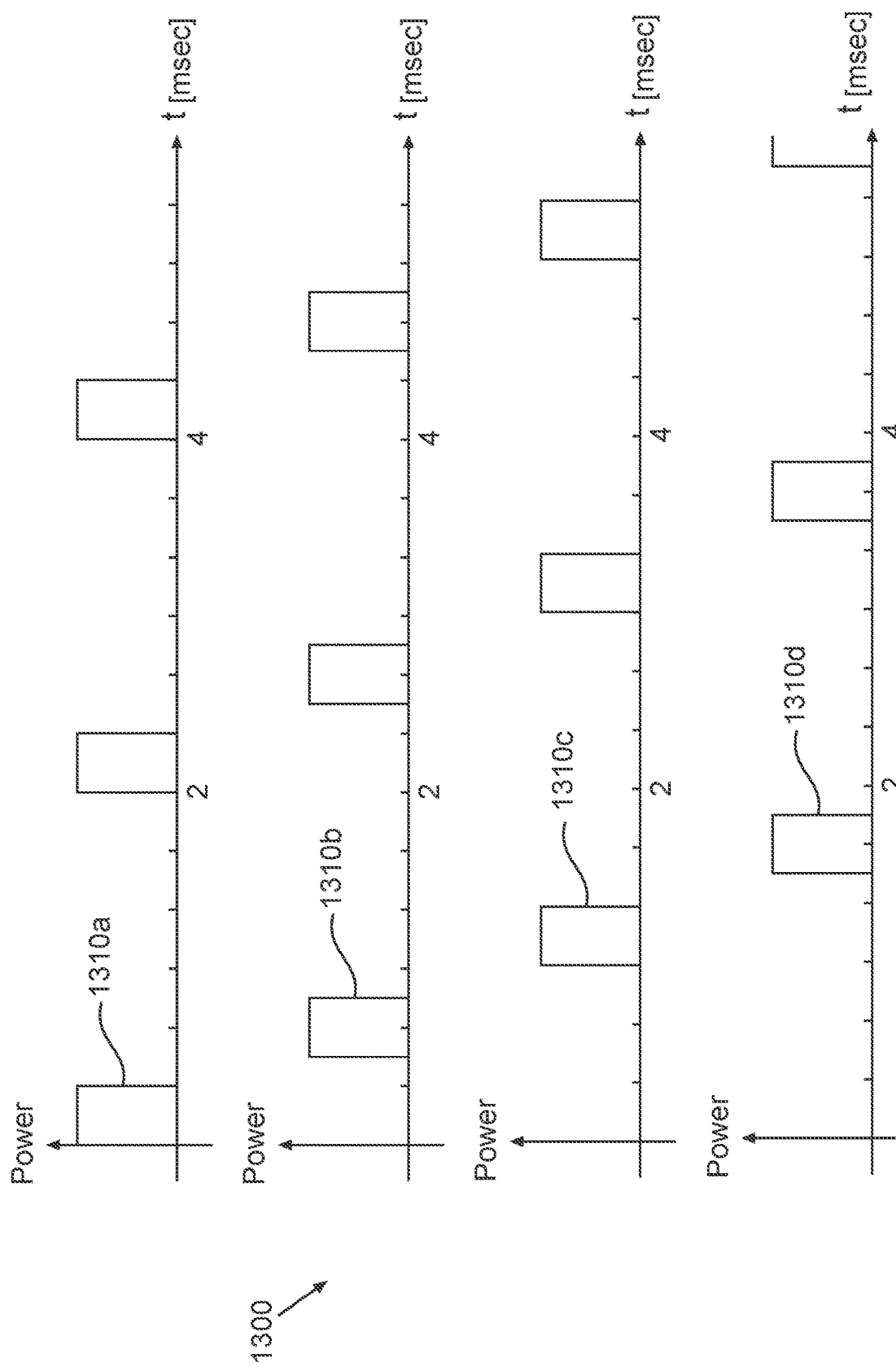
FIG. 14 depicts schematically a power distribution between four electrodes groups, such as electrode pairs, as a function of time according to some exemplary embodiments of the present invention.

According to some embodiments a high voltage high frequency signal suitable for plasma generation in container 1000 is characterized by a frequency between about 10 KHz and about 20 MHz, preferably between about 100 KHz and about 1 MHz, even more preferably a frequency between about 200 KHz and 600 KHz. It is noted that the signal's frequency may vary due to variance of specific electrical characteristics of the power source and the load (namely the electrodes and the implant), for example the inductance of coils of the step-up transformer in the power source, and capacitance of the load, particularly capacitance of the breast implant in the container. The voltage of the signal may be between about 0.5 KV to about 15 KV, preferably in the range 1-10 KV, even more preferably in the range 6-8 KV. The peak power consumed by four electrodes may be between about 0.2 W to about 20 W and according to some embodiments about 10 Watts. According to some embodiments each electrodes group may receive electric power at a duty-cycle of about 10%-20%, so that the total power consumption from the power source is at a duty cycle (DC) between 40% to 80%, for example a DC of about 60%. FIG. 14 depicts schematically a power distribution 1300 between four electrodes groups as a function of time according to some exemplary embodiments. Over a total cycle time of 2 msec the power source generates four pulses 1310a-1310d, respectively. Each pulse is distributed by the high voltage power source to one electrodes groups, for example pulse 1310a to electrodes group 1020a, pulse 1310b to electrodes group 1020b and so on. Applying plasma to a breast implant according to the parameters provided above may require no more than 5 minutes, and even no more than 2 minutes and even less than 1 minute to render a full external surface of a silicone breast implant super hydrophilic, so that the surface tension is greater than 0.072 N/m (water surface tension), in less than 40 seconds. It is noted that, typically, if the surface energy of the implant is greater than the surface energy of water, then water does not accumulate in droplets on the surface but rather wet the surface having a contact angle of substantially 0 degrees.

It is further noted that various other distribution schemes of the power between electrodes groups are contemplated, such as supplying electric power to a particular electrodes group—e.g. electrodes in electrodes group 1020b—subject to a particular modulation scheme being used. For example, plasma treatment using the first electrodes group may be conducted and completed, after which power is switched to a second electrodes group, and so on. According to such a scheme, the total time consumed for the treatment is longer compared to the distribution scheme depicted in FIG. 14, because the power source is employed at exactly the same duty cycle of a single electrodes group. Nonetheless, high-voltage switching requirements are less stringent in such a distribution scheme.

Figure 15A:
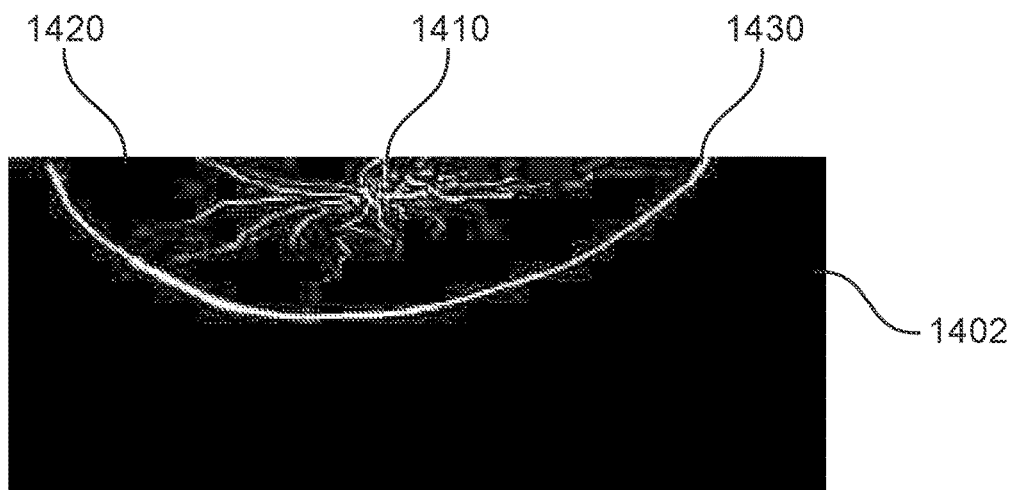
FIG. 15A is an individual image captured from a video recording, showing plasma filaments between a single pointed electrode according to the teachings herein and a silicone breast implant, distanced from the electrode by about 3 mm.
Figure 15B:
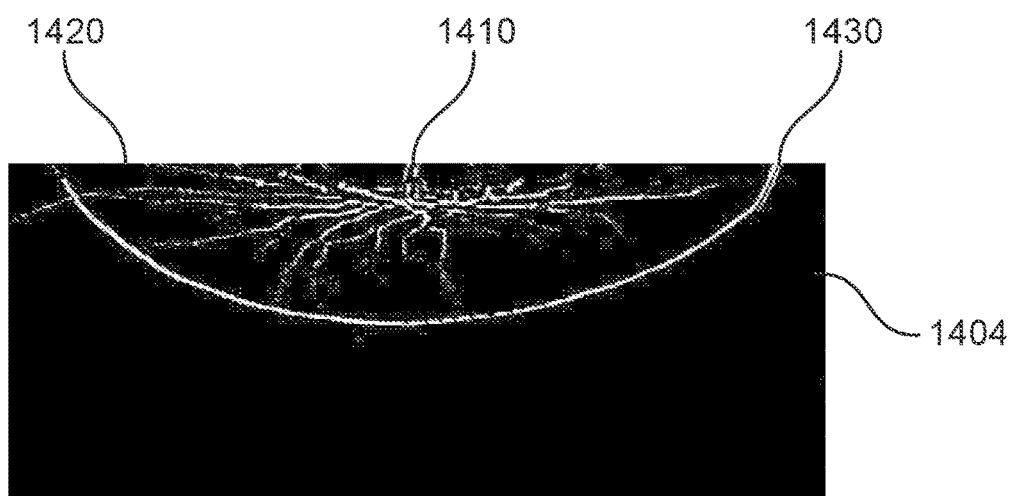
FIG. 15B is another individual image captured from the video recording of FIG. 15A.
Figure 15C:
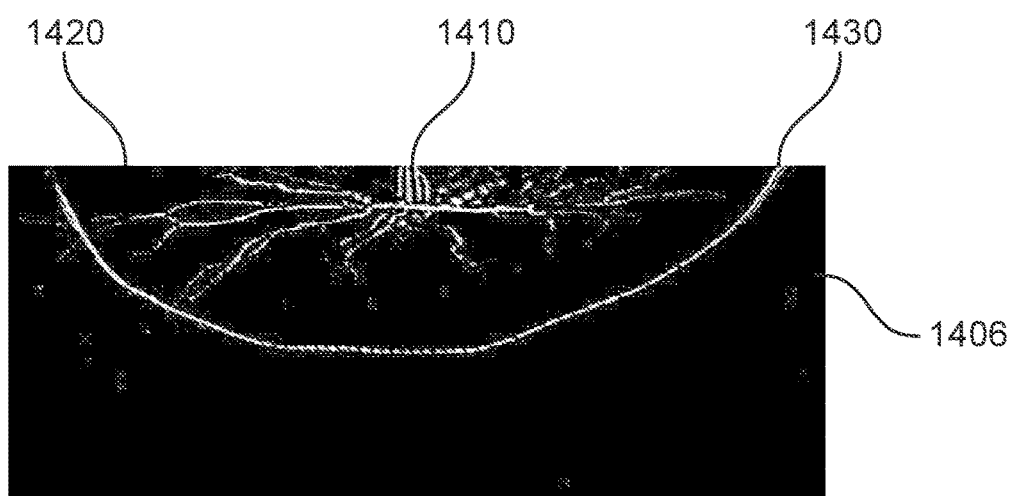
FIG. 15C is yet another individual image captured from the video recording of FIG. 15A.

FIGS. 15A, 15B and 15C are individual images 1402, 1404 and 1406, respectively, selected (captured) from a video recording, showing a single electrode 1410 positioned about 3 mm above a silicone breast implant 1420 (the border lines of the breast implant are not visible in the Figures). The electrode is supplied with an electric power suitable for producing a plasmas-generating electric field between the electrode and a portion of the surface of the implant. Glow discharge appears along flickering and swaying plasma filaments that extend from the electrode 1410 substantially downwards towards the implant, and then spread over the implant's surface in all directions until fading away on an outskirt 1430 defining a spatial area which is effectively treated.

Plasma Treatment to Breast Implants

Physical Experiments

Figure 16A:
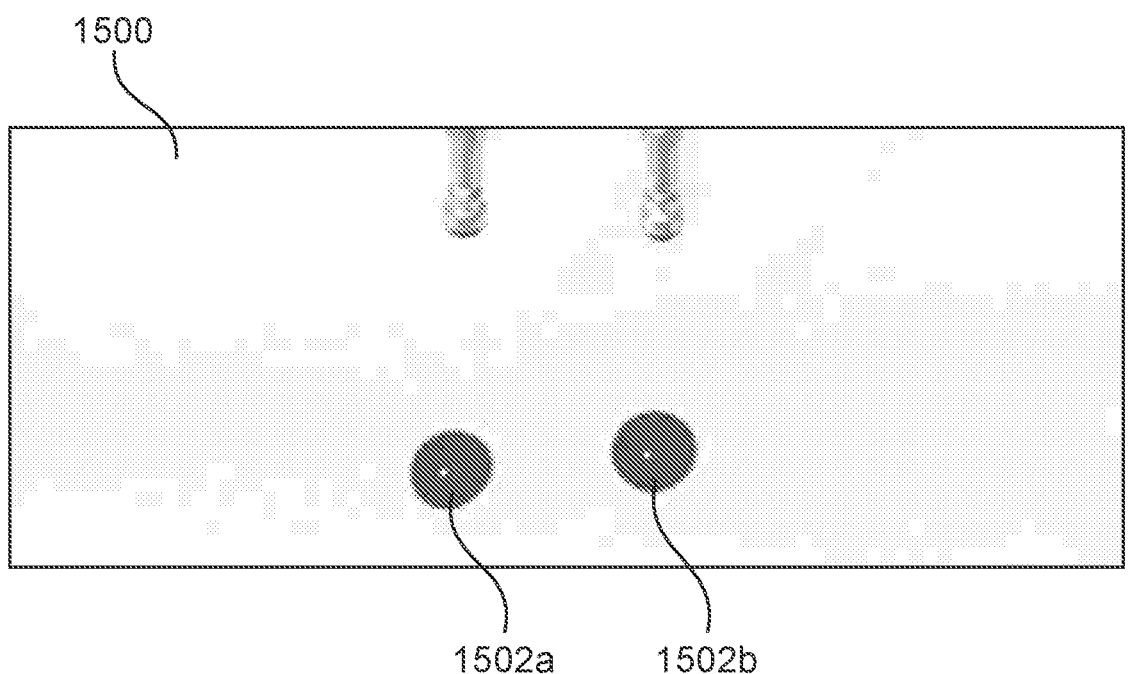
FIG. 16A depicts a photograph of two droplets of colored water on a surface portion of a silicone breast implant that did not undergo a plasma treatment.
Figure 16B:
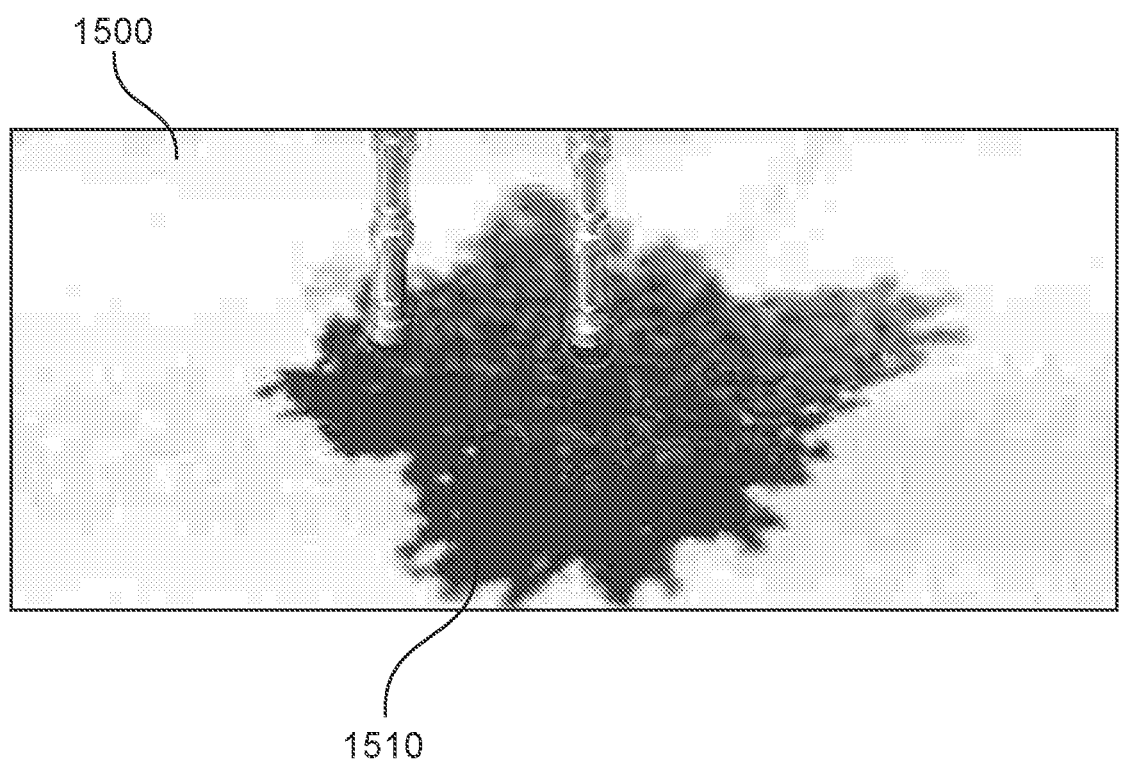
FIG. 16B depicts a photograph of a surface portion of a silicone implant that underwent a plasma treatment according to the teachings herein, followed by placement thereon of two droplets of colored water.

FIGS. 16A and 16B demonstrate an effect of plasma treating a silicone breast implant according to the teachings herein. FIG. 16A depicts a photograph of a surface portion of a silicone breast implant 1500 prior to a plasma treatment. Two droplets 1502a and 1502b of colored water are disposed gently on the surface of implant 1050 and maintain a semi-spherical shape due to a strong hydrophobicity of the surface. FIG. 16B depicts a photograph of the same surface portion of the implant 1500 following a plasma treatment according to the teachings herein of about 40 seconds. Gentle disposure of two droplets of colored water results in quick spreading of the fluid on the implant's surface and a formation of a relatively thin and relatively large-surface single stain 1510.

Figure 17:
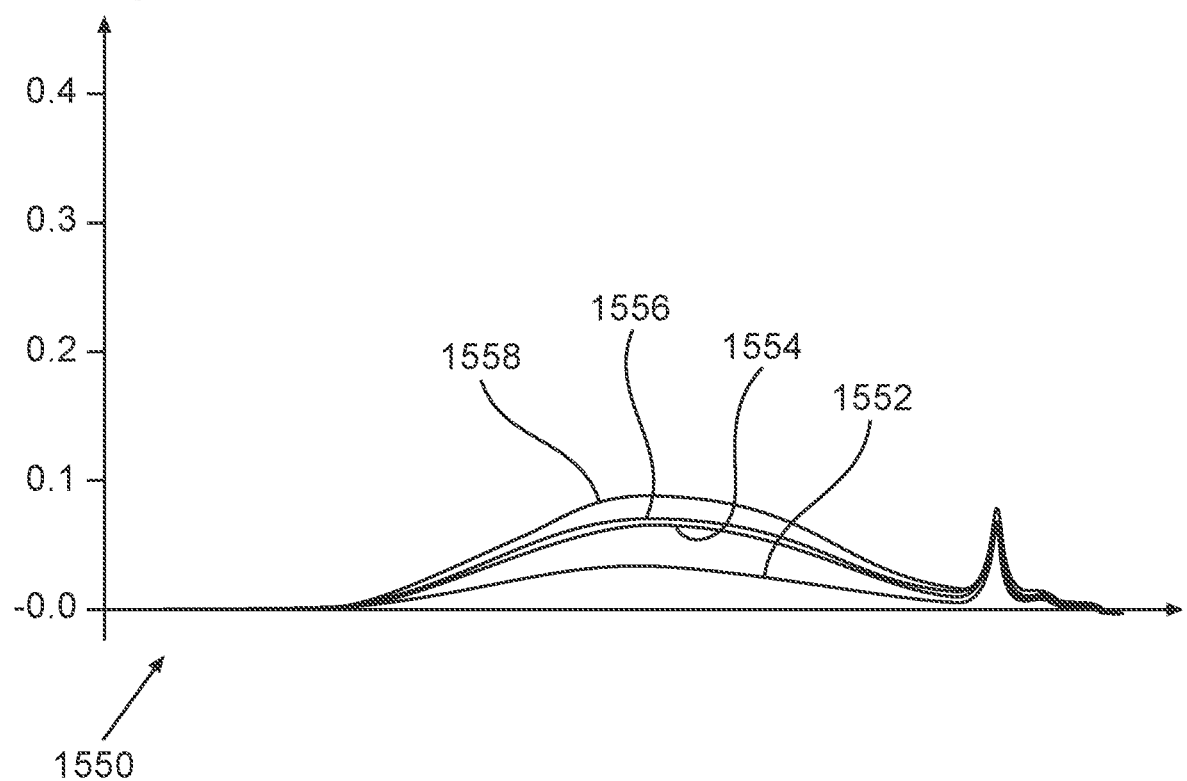
FIG. 17 schematically depicts a graph showing results of four Fourier Transform Infrared (FTIR) spectroscopy measurements, and FIG. 18 displays a photograph of a female pig following a mammary implantation surgery of a silicone implant in the course of a pre-clinical study.

FIG. 17 schematically depicts graph 1550 showing results of four Fourier Transform Infrared (FTIR) spectroscopy measurements. Curve 1552 depicts the FTIR spectroscopy results of saline disposed on a non-treated silicone implant. Curve 1554 depicts the FTIR spectroscopy results of saline disposed on a plasma-treated silicone implant. Curve 1556 depicts the FTIR spectroscopy results of an antibiotic liquid disposed on a non-treated silicone implant, and curve 1558 depicts the FTIR spectroscopy results of an antibiotic liquid disposed on a plasma-treated silicone implant. The results show that a silicone surface that underwent a plasma treatment of less than even one minute according to the teachings herein, demonstrates enhanced adhesion of saline and liquid antibiotics compared to non-treated silicone.

Without being bound to a particular theory or hypothesis, the inventors speculate that the plasma treatment may enhance or increase the surface energy of the silicone, thereby increasing the surface wettability by a polar liquid such as water or an aqueous solution or an aqueous suspension etc. They conclude that by improving the wettability of the silicone surface, enhanced transportation of agents included in the polar liquid along the surface of the silicone may be achieved. Additionally or alternatively, enhance adhesion of such agents to the silicone surface may be achieved as a result of the plasma treatment. It is noted that such beneficial effects of the plasma treatment may be limited in time, for example due to gradual decrease of surface energy of the silicone over time after the plasma treatment. Thus, significantly enhanced surface coverage of the polar liquid along the silicone surface, and/or enhanced adhesion of an agent in the liquid, may be maintained for example over one day or two days following the plasma treatment. Preparation of an implant for surgery using an effective and plausible plasma treatment followed by wetting with a polar liquid according to the teachings herein may thus be preferably carried out less than two days and even less than one day before the implantation. Most preferably, the plasma treatment and the followed wetting should be employed within a few hours before the surgery, preferably less than six hours or even less than one hour before the surgery, and preferably as an integral part of the implantation procedure and within the same premises.

In Vitro Experiments

The inventors have carried out an experiment to measure the effects of plasma treatment using the devices and methods described above to preventing possible contamination on a silicone implant. In the experiment, 8 mm silicone discs were exposed to bacterial contamination following plasma treatment and immersion in an antibiotic liquid. The results show that no bacterial contamination was found on treated silicone discs, whereas silicone discs in comparison groups that were not treated and were similarly exposed to bacterial contamination became contaminated.

Silicone discs, in a diameter of 8 mm, made of breast implant (by Mentor, Dallas, Tex.), received the different treatments as described in table 1 below.

TABLE 1

| [#] | Group | Number of samples | Plasma Treatment | Antibiotic Treatment |
|---|---|---|---|---|
| 1 | No Antibiotics (—), BC = $10^2$ (Dry) | 2 | No | No |
| 2 | No Antibiotics (—), BC = $10^5$ (Dry) | 2 | No | No |
| 3 | No Antibiotics (—), BC = $10^2$ (Saline) | 2 | No | No |
| 4 | No Antibiotics (—), BC = $10^5$ (Saline) | 2 | No | No |
| 5 | Antibiotics (A), BC = $10^2$ | 2 | No | Yes |
| 6 | Antibiotics (A), BC = $10^5$ | 2 | No | Yes |
| 7 | Antibiotics + Plasma (A + P), BC = $10^2$ | 2 | Yes | Yes |
| 8 | Antibiotics + Plasma(A + P), BC = $10^5$ | 2 | Yes | Yes |
| 9 | Plasma (P), BC = $10^2$ | 2 | Yes | No |
| 10 | Plasma (P), BC = $10^5$ | 2 | Yes | No |
| | Total Number of samples | 20 | | |

BC stands for bacterial concentration;

(−) signifies no plasma treatment and no immersion in antibiotics liquid;

(A) signifies immersion in antibiotics liquid;

(P) signifies plasma treatment;

(A+P) signifies plasma treatment followed by immersion in antibiotics liquid.

(Dry) means that a non-plasma-treated, dry silicone disk was exposed to bacterial contamination, (Saline) means that a non-plasma-treated silicone disk was wetted by sterile saline prior to being exposed to bacterial contamination.

For plasma treatment, discs (in groups 7, 8, 9, and 10 above) were subjected to direct plasma for about 40 seconds. In each plasma treatment, three discs were simultaneously treated. The disks were placed next to one another on an insulating layer about 1 mm thick above a common sheet electrode, under a pointed high voltage electrode. Plasma was ignited at a voltage of about 6 KV, a frequency of about 150 KHz, and pulsed at a rate of about 500 Hz and duty-cycle of about 30%. The atmosphere around the discs consisted substantially of Argon at Atmospheric pressure (about 1 Bar), flushing through the plasma-excited region at a rate of about 2 liters/sec. Plasma activation resulted in plasma filaments swaying along the top surface of the discs, substantially as depicted in FIGS. 15A-15C.

For immersion in antibiotics liquid, disks (5, 6, 7 and 8) were fully immersed in a tube containing an antibiotics liquid consisting of Cephalosporin 1st generation Cefamezin, at concentration of 1 g/1 liter of saline.

For preparation of a contaminated surface, two *Staphylococcus Aureus* inoculums were prepared, the first forming a $10^2$ CFU/ml and the second a $10^5$ CFU/ml. A 50 ul (micro-liter) drop from each of the inoculums where applied on a blood agar plate. The drop dispersed nicely to a diameter of about 2 cm. Three drops (from a same inoculum) where applied in each plate in even distances from each other making sure there is no contact between them. The plates where left in a sterile hood to dry for 30 minutes until complete drying.

Exposure to bacterial contamination and bacterial contamination measurement were carried out as follows: each (post treated) disk ("measured disk") was pressed onto a 12 mm sterile silicone disk ("carrier disk") until the two disks stuck together, to allow handling by holding only the carrier disk. The measured disk was rubbed gently on the agar plate contaminated area, in a circular motion, making sure each disc performs 5 circles to the right and five to the left. After contamination, the silicone discs where inserted into a growth medium in an Eppendorf tube (1 ml) for incubation. After 24 hours of incubation, samples from the growth medium were seeded and bacterial concentration where counted. Eight days post insertion of the discs into the growth medium, the discs were removed from the tube, stained by a fluorescence-staining agent and taken to be investigated by confocal microscopy.

Average results of bacteria count in a sample of the growth medium of each disk are presented in Table 2:

TABLE 2

| | (—) (CFU/ml) | A (CFU/ml) | P (CFU/ml) | A + P (CFU/ml) |
|---|---|---|---|---|
| $10^2$ | $7 \times 10^5$ | — | — | — |
| $10^5$ | $7 \times 10^6$ | $1.5 \times 10^5$ | $7 \times 10^6$ | — |

The results show that of the disks that were contaminated by the "low" bacteria contamination of $10^2$ CFU/ml (lines 1, 3, 5 7 and 9 in Table 1), the disks that were not treated at all (lines 1 and 3) were subsequently contaminated (an average $7 \times 10^5$ CFU/ml was measured) whereas disks that were immersed in antibiotics (line 5), disks that plasma-treated (line 9) and disks that were first plasma treated and then immersed in antibiotics (line 7), were found void of contaminations.

Of the disks that were contaminated by the "high" bacteria contamination of $10^5$ CFU/ml (lines 2, 4, 6, 8 and 10 in Table 1), the disks that were not treated at all (lines 2 and 4), the disks that were immersed in antibiotics (without prior plasma treatment) (line 6), and disks that plasma-treated (without a following immersion in antibiotics) (line 10) were subsequently contaminated (an average $7 \times 10^6$ CFU/ml was measured). Only the disks that were first plasma treated and then immersed in antibiotics (line 8), were found void of bacteria contamination.

Confocal microscopy measurement of disks that were kept in a growth medium for eight days following exposure to contamination, as described above, revealed substantially similar results.

In Vivo Pre-Clinical Experiments

In vivo pre-clinical experiments for studying and verifying the effects of plasma treating silicone breast implants in porcine model are currently being conducted by the inventors. The objective of the study is to test in-vivo the silicone implant surface activation followed by antibiotics immersion on *Staphylococcus* infection using an experimentally infected foreign body model in pigs. The results are assessed in terms of:

A) Reduction of infection and biofilm accumulation on the implant;

B) Reduction of capsular contraction, and

C) Safety test—unexpected safety issues following plasma surface activation followed by antibiotics immersion and implantation in pigs.

The experiment compares activated implants to non-activated implants (control) in terms of infection, inflammatory reaction, biofilm buildup and capsular contraction (it is noted that "capsule" and capsular contraction refer here to the formation of a biological capsule, typically of collagen fibers, inside the patient's body, around the installed implant). The study evaluates if there are unexpected side-effects and/or other benefits to the plasma activation process.

The model is based on the use of silicone breast implants (volume 150 cc, textured type by Mentor, Dallas, USA), identical to implants used in breast surgery. The implants are placed under the nipple using aseptic technique identical to that used in clinical practice. Each animal receives 4 to 8 implants that serve as reference one to the other. Plasma treatments to implants is given using a device such as the devices described above, e.g. in FIGS. 10 and 11, and in related electrical diagrams.

Adult, female farm pigs, weighing 150 to 250 kg (Lahav CRO, Kibbutz Lahav, Israel) are used. The pigs are housed under controlled conditions, e.g. of temperature and humidity. For surgery, the pigs are euthanized by an IV 8 ml Pental and 20 ml KCl injection. The pigs are fasted overnight before surgery. Anesthesia is induced with 1-3% Isoflurane breathing, Katamine at 10 mg/kg and ksilazen 2 mg/kg intramuscular and Asival 5 mg Intravenous. The trunk of the pig is prepared surgically using a 10% povidone-iodine wash (Orion, Welshpool, Western Australia, Australia) and a 70% alcohol rinse. Sterile surgical drapes are used to completely cover the pig while keeping the teats adequately exposed. An antimicrobial Ioban drape (3M Health Care, St. Paul, Minn.) is applied to cover all teats. Standard sterile operative techniques such as those in human implantation are used, including change of gloves and instruments with each implant placement, ensuring hemostasis before implant insertion, minimizing implant handling, and avoiding contact of the implant with skin.

A submammary pocket is fashioned using blunt dissection. The mammary implant is inserted aseptically into the submammary pocket. The surgical wound is then closed in two layers: interrupted deep layer sutures, and a continuous subcuticular closure. Absorbable sutures, 4-0 undyed Monocryl (Ethicon, Inc., Somerville, N.J.), are used.

Implants are plasma treated, immersed in antibiotics (Cephalosporin 1st generation Cefamezin, 1 g/l liter of saline), contaminated by bacteria as further detailed below, and inserted to the pocket. Plasma treatments to implants is given using a device such as the devices described above, e.g. in FIGS. 10 and 11, and in related electrical diagrams. Control implants do not receive plasma treatment. All plasma activated implants receive the same intensity and duration of plasma activation, using the same RF parameters. The implants are activated (treated) immediately prior to immersion in antibiotics, contamination and implantation, making sure that the implantation is done not more than 30 minutes after the activation.

Figure 18:
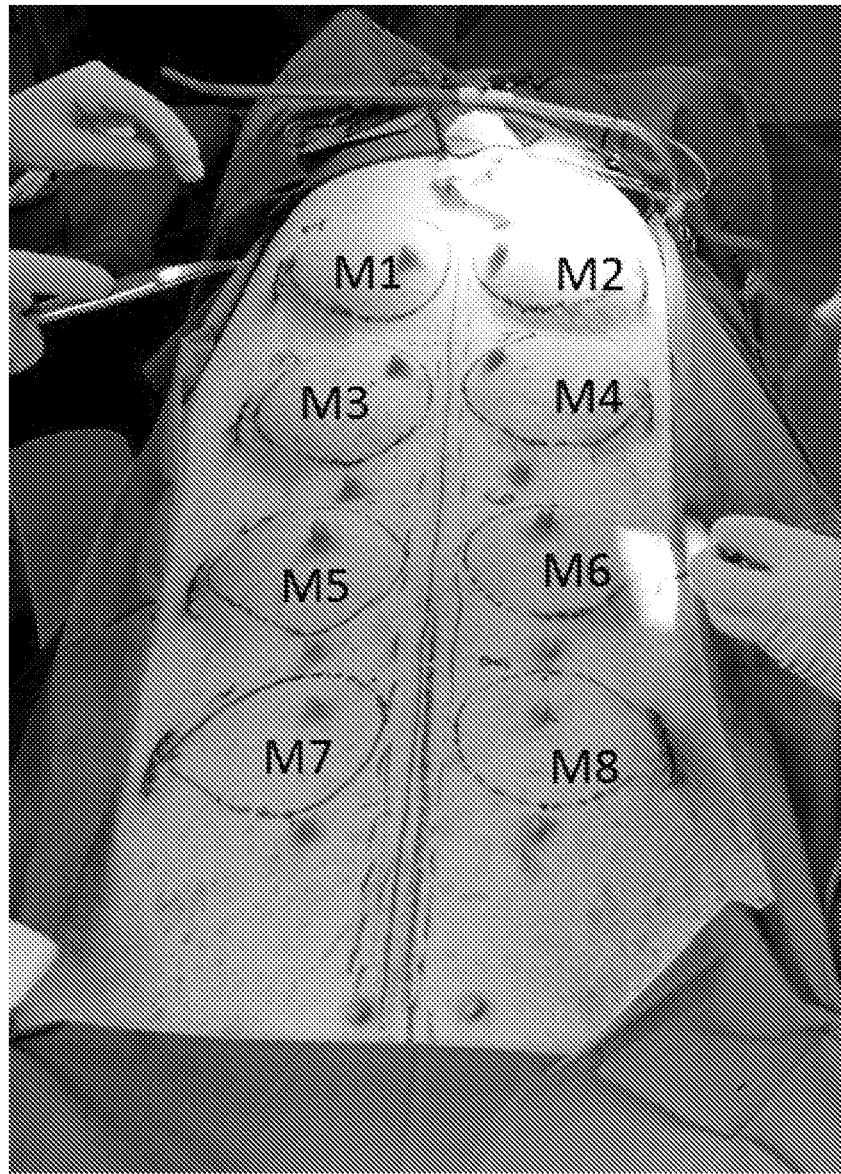

In a Pilot Study phase, a single female pig (n=1) receives 8 implants wherein 4 of them (group A) are not plasma-treated, immersed in antibiotics and *Staphylococcus Aureus*-contaminated (105 colony-forming units), and the other 4 (group B) are plasma-treated, immersed in antibiotics and *Staphylococcus aureus* contaminated (105 colony-forming units). FIG. 18 displays a photograph of the pig following the implantation surgery. Marks M1, M2, . . . , M8 on the image designate the locations where the eight implants are emplaced. Table 3 details which of the implants are plasma-treated.

TABLE 3

| Implant number | M1 | M2 | M3 | M4 | M5 | M6 | M7 | M8 |
|---|---|---|---|---|---|---|---|---|
| Plasma Treatment [Y/N] | N | Y | Y | N | N | Y | Y | N |

Implants from group A (no plasma), prior to immersion in antibiotics, are inserted into the plasma device and extracted immediately, without undergoing plasma treatment, to avoid biases such as unexpected contamination coming from the plasma device. The implants are implanted in an intermediate order such that between each plasma-treated implant, a non-treated implant is located. After surgery, the pig is monitored daily for survival, rectal temperature, weight, and surgical wound healing. The pig is monitored for 1-2 months until a significant capsular contracture can be evaluated. The differences in CC baker grade between plasma-treated and untreated implants are analyzed. After euthanasia, the following is analyzed:

1. Capsular contracture baker grade;
2. Infection evaluation—redness, secretion, edema;
3. Biofilm formation by viable bacterial counts and fluorescent confocal microscopic analysis of implants;
4. Capsular contraction—capsule surface area measurement and capsule width by histology;
5. Complete Blood Count (CBC), C-Reactive protein collection (CRP);
6. Unexpected or unpredicted effects indicating safety issues for the implant pre-treatment;
7. Implant shell intact;

If during the pilot study capsular contracture can be evaluated by feel, the "Main study" is initiated. If no CC Baker II-IV is detected, the subsequent pigs receive a higher inoculum bacterial concentration and/or a different bacteria species.

In the Main Study phase, 4 pigs (n=4) undergo the procedure of the "Pilot Study" as described above. The implants order (treated vs. non-treated) in each pig is varied between pig to pig to avoid a systematic effect and bias due to the implantation location. Table 3 summarizes the related Design of Experiments (DOE).

In an Advanced Study phase additional 5 pigs are planned to undergo the same procedure as described above for the "Main Study".

TABLE 4

| Pig Number [#] | Implant serial number | Plasma Treatment | Antibiotic Treatment | Baker grade evaluation | Viable bacterial counts | Confocal microscopy | Histology of the capsule |
|---|---|---|---|---|---|---|---|
| 1 | A1 | No | Yes | Yes | Yes | Yes | Yes |
|   | A2 | Yes | Yes | Yes | Yes | Yes | Yes |
|   | A3 | Yes | Yes | Yes | Yes | Yes | Yes |
|   | A4 | No | Yes | Yes | Yes | Yes | Yes |
|   | A5 | No | Yes | Yes | Yes | Yes | Yes |
|   | A6 | Yes | Yes | Yes | Yes | Yes | Yes |
|   | A7 | Yes | Yes | Yes | Yes | Yes | Yes |
|   | A8 | No | Yes | Yes | Yes | Yes | Yes |
| 2 | B1 | Yes | Yes | Yes | No | Yes | Yes |
|   | B2 | Yes | Yes | Yes | Yes | No | No |
|   | B3 | Yes | Yes | Yes | Yes | No | No |
|   | B4 | Yes | Yes | Yes | Yes | No | No |
|   | B5 | No | Yes | Yes | Yes | No | No |
|   | B6 | No | Yes | Yes | Yes | No | No |
|   | B7 | No | Yes | Yes | Yes | No | No |
|   | B8 | No | Yes | Yes | No | Yes | Yes |
| 3 | C1 | Yes | Yes | Yes | No | Yes | Yes |
|   | C2 | Yes | Yes | Yes | Yes | No | No |
|   | C3 | Yes | Yes | Yes | Yes | No | No |
|   | C4 | Yes | Yes | Yes | Yes | No | No |
|   | C5 | No | Yes | Yes | Yes | No | No |
|   | C6 | No | Yes | Yes | Yes | No | No |
|   | C7 | No | Yes | Yes | Yes | No | No |
|   | C8 | No | Yes | Yes | No | Yes | Yes |
| 4 | D1 | Yes | Yes | Yes | No | Yes | Yes |
|   | D2 | Yes | Yes | Yes | Yes | No | No |
|   | D3 | Yes | Yes | Yes | Yes | No | No |
|   | D4 | Yes | Yes | Yes | Yes | No | No |
|   | D5 | No | Yes | Yes | Yes | No | No |
|   | D6 | No | Yes | Yes | Yes | No | No |
|   | D7 | No | Yes | Yes | Yes | No | No |
|   | D8 | No | Yes | Yes | No | Yes | Yes |
| 5 | E1 | Yes | Yes | Yes | No | Yes | Yes |
|   | E2 | Yes | Yes | Yes | Yes | No | No |
|   | E3 | Yes | Yes | Yes | Yes | No | No |
|   | E4 | No | Yes | Yes | Yes | No | No |
|   | E5 | No | Yes | Yes | Yes | No | No |
|   | E6 | No | Yes | Yes | No | Yes | Yes |

A clinical isolate of *Staphylococcus aureus* recovered from a foreign body infection is used in all in vivo experiments. This strain was used in the in-vitro experiments described above and showed the capacity of proliferation and biofilm production on silicone implant surface.

At the Rambam medical center microbiology laboratory, a 105 CFU inoculate of the above mentioned staph bacteria is dripped, using a pipetor, on agar plates in 10 symmetrical locations, with the same drop volume for each location. The plates are left to dry in a hood for 30 minutes until a complete drying. After drying, the plates are closed and inserted in a cardboard box for transportation.

The driving duration to LRI, where the in-vivo experiments take place, is about two hours. Taking into account preparations and spares, the contaminated agar plates are thus used 3-4 hours after contamination. In this 3-4 hours period, there is no significant change in the bacteria concentration on the agar plate.

Each implant, after undergoing the preventive treatment (group A—antibiotics immersion only, group B—plasma+antibiotics immersion), is rubbed on the agar plate, in a circular motion, 5 circles to the right and 5 to the left. The implants are grabbed from its flat (anterior) side and rubbed on the agar whereas its round side comes in contact with the contamination. When inserting the implant to the implant pocket, an effort is made to touch as minimum as possible the round side.

Clinical parameters (weight, rectal temperature, and surgical wound healing) are examined daily after surgery. Wound healing is assessed on day 11 using a score scale from 0 to 3 (0, normal healing; 1, closed suture line, pus-discharge; 2, partial dehiscence, pus-discharge; and 3, complete dehiscence, abundant discharge, and tissue necrosis).

For evaluation of the implant and capsule after euthanasia, care is taken so that the implants should arrive to bacteriology analysis as fast as possible, and in less than two hours. After euthanasia, viable *Staphylococcus* counts are performed on specimens obtained from removed implants to quantify bacterial load. *Staphylococcus* counts are performed also on grounded spleen specimens removed from all animals to assess for systemic bacterial dissemination. Designated implants are removed from the pigs under sterile conditions and placed in sterile containers containing saline, washed with saline to remove planktonic bacteria, and then put through two cycles of vortex and sonication (5 minutes, 37 kHz, sonication bath) to release bacteria from matrix. The resulting suspension is serially diluted and plated onto blood agar plates for bacterial enumeration. Representative implant from each animal (according to Table 3 above) is visualized using fluorescent confocal microscopy. A small sample (1×1 cm) from each implant is sliced and inserted in formaldehyde 4%. The sample is then taken to a confocal microscope, stained and evaluated for biofilm formation.

The detailed sequence of steps taken is as follows: A clinical assessment of capsular contracture (Baker grade) is performed. The pig is sedated and placed on the euthanasia table. The pig abdomen is shaved and disinfected using the same method as customary done prior to surgery. Capsular contracture evaluation by feel is performed, as done in previous follow-up visits and Baker grade score is given to the implants. After determining baker grade by feel, the pig is euthanized.

The entire abdomen is separated using sterile tools and keeping aseptic methods as much as possible. The abdomen is inserted inside a sterile plastic bag and placed in a cooler containing ice. A thermometer is placed inside the cooler for temperature monitoring. The capsules are then transported to bacteriology assessment site in refrigerated container at 4 degrees Celsius.

The capsules-containing implants are extracted from the abdomen, onto a sterile field, using aseptic methods (sterile tools, gloves and environment). Each capsule is placed on a sterile glass plate marked with the implant number inside a hood. The capsules are positioned anterior side facing up. Representative picture of the capsule are then taken and the capsules dimeters (three (3) measurements: diameter along two orthogonal axes and height using a level placed on the capsule) are measured using a sterile caliber in a sterile fashion on the sterile plates.

Implants are extracted from the capsules inside a hood, using aseptic methods. The capsular contracture is assessed by evaluating the implant "squeeze amount". Capsules and implants are placed together, back at sterile plates in the same orientation (anterior up). The implants are inspected for visual damage and pictures from 3 different angles are taken.

Each implant surface is sampled from six (6) different sites by applying 6 different contact plates contacted with the implant surface. The contact plates are marked by "Imp X" and "Pl Y"—meaning implant number X and plate number Y. Before using the contact plates, 3 locations (1.5×1.5 cm) are marked using a marker, for the later extraction of samples for microscopy, and those locations are guarded from being contacted.

Initially, the upper and lateral sides (anterior and lateral) are contacted by four 4 plates where Pl 1 is contacted in the anterior center and plates Pl 2-4 are contacted in the lateral sides. Then the implant is lifted by hand using sterile gloves and additional two (2) plates, Pl 5, and Pl 6 are contacted with the posterior side. The contact plates are placed in incubation at 37° C. for 18 hours and monitored for growth. If single colonies are obtained after ON incubation, bacterial counts are performed. If confluent growth is obtained, a semi quantitative analysis is performed indicating the grade of growth (+++ heavy growth, ++ medium+growth but uncountable colonies).

Three (3) capsule specimen in a diameter of 7 mm are cut using a sterile puncher, one from posterior side, one from anterior side and one from lateral side. The capsule specimen are homogenized for determination of bacterial counts by placing each specimen in a sterile manner in a sterile eppendorf with 1 mL sterile saline, and are homogenized using a pestel motor mixer equipped with 1.5 mL pestel. Homogenized suspensions is serially diluted and plated onto blood agar plates. Three (3) capsule samples in a size of 1×2 cm are also cut, one from posterior side, one from anterior side and one from lateral side. Each sample is attached to a flat cardboard to keep it stretched. Samples are inserted into pre-marked vails containing formaldehyde 4%. The vials are marked by "Imp X", "His Y", meaning implant number X and histology sample number Y. The samples are then taken to histology lab.

Three (3) Implant shell samples in a size of 1×1 cm are cut and peeled of the implant, from the locations previously marked, one from posterior side, one from anterior side and one from lateral side. The samples are inserted into pre-marked vails containing formaldehyde 4%. The vials are marked by "Imp X", "Mic Y", meaning implant number X and Microscopy sample number Y. The samples are then taken to Microscopy evaluation. Each capsule is also measured using a caliber, for wall thickness in 3 locations—anterior, posterior and one side. The data are collected and analyzed.

According to some embodiments a method of treating an implant made of an electrically isolating material prior to a medical procedure involving emplacement of the implant in a body of a live subject is provided. According to some embodiments the implant is made of silicone or has a silicone external shell or external surface. According to some preferred embodiments the implant is a breast implant. The method may comprise the following steps (without loss of generality, and for the sake of clarity, the description herein is directed to a breast implant):

(a) A device for plasma-treating the breast implant according to the teachings herein is provided in a clinic where the medical procedure is intended to be carried out. The device may include a container, e.g. like container 1000 described herein, having a compartment configured to contain therein the implant and electrodes for generating plasma in the compartment near the implant. The device may further comprise an electric power source configured to generate electric power suitable to produce a plasma-generating electric field when supplied to the electrodes of the container. According to some embodiments the container is a disposable component and configured substantially for a single use. According to some embodiments the container is portable and configured to store the implant therein e.g. in a manufacturing site of the implant and during shipment of the implant to the clinic. In embodiments wherein the container is portable, the container may be electrically connected to the power source stationed in the clinic for operation and use. Thus, according to some embodiments, an implant intended to be implanted may be received from shipment, being stored and shipped inside the container within which plasma will be generated. According to some embodiments, an implant intended to be implanted may be received from shipment removed from the package within which the implant was shipped and be disposed inside the container of the invention for being plasma-treated.

According to some embodiments the device may include an operating unit, the operating unit including the power source, a controlling unit and also including a gas pump or a gas reservoir. According to some such embodiments the operating unit may be connected to the container via an electric cable and possibly via a tube for carrying gas from the gas reservoir to the container or/and for pumping the compartment.

(b) According to some embodiments the container may be located in the clinic in a sterile area possibly in the operation room. The power source that supplies to the container electric power, and/or the controlling unit of the device, associated with the power source and configured to allow a user to command the device, may be situated in a non-sterile region of the clinic and may accordingly be operated by a "non-sterile" operator. In the sterile area near the container, the breast implant (that has been received in the clinic for the emplacement) may be removed from a package in which the implant was shipped to the clinic, and disposed inside the compartment of the container.

(c) The compartment may be closed and sealed, and an ionisable gas may be flown into the compartment. Alternatively or additionally pumping the compartment may be employed to reduce the pressure or partial pressure of the gas (e.g. air or an admixture of the ionizable gas and air) in the interior of the compartment. Alternatively or additionally plasma may be ignited and maintained at ambient conditions, namely at atmospheric pressure and composition of the gas (air) inside the compartment.

(d) The electric power source may be activated thereby effecting plasma generation inside the compartment substantially around the implant, e.g. between the electrodes (or, in some embodiments, between some of the electrodes) and the implant.

(e) After plasma generation is completed, the breast implant may be wetted by a liquid containing a therapeutically effective agent (or more than one). Therapeutically effective agents may include antimicrobial agents (including antibiotics, antiseptics, and disinfectants), anesthetics, analgesics, anti-inflammatory agents, anti-scarring agents, anti-fibrotic agents, anti-cancer compounds, hemostatic material for controlling bleeding, hormone therapeutics, stem cells, and cellular precursors. Examples for antiseptic agents include cefamizine, ghentamicin vancomicine, rifampin, minocycline and cloxacillin. An example for antiseptic agent is betadin. Anti-inflammatory agents include, but are not limited to, prednisone, dexamethasone and zafirlukast. Anti-cancer compounds include, bur are not limited to alkylating agents, antibiotic agents, antimetabolic agents, hormonal agents, plant-derived agents and their synthetic derivatives, anti-angiogenic agents, differentiation inducing agents, cell growth arrest inducing agents, apoptosis inducing agents, cytotoxic agents, agents affecting cell bioenergetics i.e., affecting cellular ATP levels and molecules/activities regulating these levels, biologic agents, e.g., monoclonal antibodies, kinase inhibitors and inhibitors of growth factors and their receptors, gene therapy agents, cell therapy, e.g., stem cells, or any combination thereof.

(f) The implant may be rinsed with the liquid or sprayed onto with the liquid or immersed in the liquid. According to some embodiments the implant may be removed from the container prior to wetting the implant and the implant is wetted outside the compartment. According to some embodiments, a suitable liquid may be injected into the compartment of the container to wet the implant through the liquid port of the container as described above.

(g) Following wetting the implant, e.g. by an antibiotic liquid, the implant may be taken for surgery and emplaced in a body of a live subject. According to some embodiments, the plasma treatment may be provided to the implant prior to the surgery, e.g. less than 48 hours or even less than 24 hours before the surgery.

According to some embodiments, the plasma treatment may be provided to the implant just prior to such a medical procedure, namely on the same day of the surgery e.g. less than six hours before the medical procedure and preferably less than one hour before the surgery. It is noted that beneficial effects of the plasma treatment decay, fade away and disappear gradually following the plasma treatment hence it is advantageous to shorten the time between the plasma treatment and the implantation.

There is thus provided according to an aspect of the invention an apparatus (100, 200, 400, 500, 800, 800a-800g) for plasma treatment of an implant prior to installing the implant in a live subject. The apparatus comprises an activation device (110, 210, 410, 510, 810, 810a-810g) and a portable container (120, 120c, 220, 220a-220c, 300, 420, 600, 650, 680, 820, 820a-820g) detachable from the activation device. The portable container comprises a closed compartment (130, 230, 310, 430, 620, 652, 682, 830, 830a-830g) containing the implant immersed in a fluid. The activation device comprises a slot (140, 240, 450, 840, 840a-840g) configured to receive the portable container. The activation device further comprises an electrical circuit (150, 250, 460, 846, 846a-846g) configured to be electrically associated with at least one electrode (160, 170, 180a, 180b, 260, 270, 280a, 280b, 464, 630, 662, 684, 860, 860a-860g) and configured to provide to the at least one electrode electric power suitable for applying a plasma generating electric field in the closed compartment, when the portable container is disposed in the slot.

According to some embodiments the closed compartment (130, 230, 310, 430, 620, 652, 682, 830, 830a-830g) may be ventilated to ambient atmosphere while being microbially sealed, the fluid being thereby maintained at ambient pressure and composition.

According to some embodiments the portable container (300, 420, 600) further comprises a valve (330, 440, 640) operable to be opened and closed and is fluidly associated with the closed compartment. According to some embodiments the portable container (300) further comprises a gas reservoir (320) containing pressurized gas and in fluid communication with the valve, wherein opening the valve allows fluid communication between the gas reservoir and the closed compartment.

According to some embodiments the activation device (410, 510) has a fluid port (470), being configured to fluidly connect to the valve (440) when the portable container is disposed in the slot (450). According to some embodiments the fluid port is fluidly associated via a controlled valve with a fluid source (480) of the activation device. According to some embodiments the fluid source is a gas reservoir. According to some embodiments the fluid port (470) is fluidly associated via a controlled valve with a gas pump (520) of the activation device.

According to some embodiments the at least one electrode (160, 260) consists of a single electrode.

According to some embodiments the at least one electrode (160, 260, 684) comprises an elongated conductor (172, 262, 686) substantially wound around the implant when the portable container is disposed in the slot (140b, 240). According to some embodiments the elongated conductor (172, 262) is wound around the closed compartment. According to some embodiments the elongated conductor (262) is comprised by the activation device (210), being wound around the closed compartment when the portable container is disposed in the slot (240).

According to some embodiments the at least one electrode (170, 270, 662) comprises a cylindrical conductor (172, 272) substantially enveloping the implant when the portable container is disposed in the slot (140, 240).

According to some embodiments the apparatus (activation device 110 with portable container 680) is configured for plasma generation inside the sealed compartment in an Inductive Coupled Plasma (ICP) mode of operation.

According to some embodiments the at least one electrode comprises two electrodes (170 and implant 132 in FIG. 1C, 180A and 180B in FIG. 1D, 270 and implant 132 in FIG. 2C, 280A and 280B in FIG. 2D) electrically disconnected from one another, configured to apply a plasma-generating electric field therebetween in a Capacitance Coupled Plasma (CPC) mode of operation. According to some embodiments the two electrodes (180A and 180B in FIG. 1D) are comprised by the activation device, being configured to apply the plasma-generating electric field when the portable container is disposed in the slot.

According to some embodiments at least one of the electrodes (FIGS. 1B-1D, 2B-2D, 5B) of the portable container are electrically isolated from the fluid contained in the closed compartment, being thereby configured to generate plasma in the closed compartment in a Dielectric Breakdown Discharge (DBD) mode of operation.

According to some embodiments the plasma generating electric field is a DC electric field. According to some embodiments the plasma generating electric field is an AC electric field. According to some embodiments the plasma generating electric field generates plasma in the closed compartment at a voltage lower than 5 KV between any of the at least one electrode.

According to some embodiments the apparatus (100, 200, 400, 500, 800, 800a-800g) further comprises an initial high voltage pulse generator (1250), the initial high voltage pulse generator being configured to electrically associate with at least one dedicated ignition electrode positioned proximal the closed compartment when the portable container is disposed in the slot, thereby being configured to generate a high voltage ignition field inside the closed compartment through the at least one ignition electrode.

According to some embodiments (FIG. 1C, FIG. 2C, FIG. 5B, FIG. 6, FIG. 8B) the at least one electrode comprises at least a portion of a surface of the implant when the portable container is disposed in the slot.

The apparatus of claim 1 wherein the portable container (220b, 220c, 220d, 600, 650, 680) further comprises at least one electrode (260, 270, 280a, 280b, 630, 662, 684) electrically associated with an at least one electric conductor (254, 274, 284, 432, 690) outside the closed compartment and configured for applying a plasma-generating electric field inside the closed compartment.

According to some embodiments the portable container (600, 650) further comprises an external capsule (610) containing therein the closed compartment (620, 652). According to some embodiments the external capsule is configured for freely releasing the closed compartment therefrom. According to some embodiments the portable container (600, 650) further comprises at least one electrode (630, implant 132 in container 650), disposed inside the external capsule (610) and being electrically associated with an at least one electric conductor (432) outside the external capsule and configured for applying a plasma-generating electric field inside the closed compartment. According to some embodiments the portable container (650) further comprises at least one floating electrode (660) disposed inside the external capsule, being thereby electrically isolated from any conductor outside the external capsule, and shaped to envelope or encircle the closed compartment (652).

There is further provided according to an aspect of the invention an activation device (700, 750) for plasma treatment of an implant prior to installing the implant in a live subject. The activation device comprises an implant holder 134 configured to support the implant in a chamber 720 during plasma treatment. The activation device further comprises an initial high voltage pulse generator 792, configured to electrically associate with at least one ignition electrode 790 positioned proximal the implant holder, and preferably in the chamber. The initial high voltage pulse generator is thereby being configured to generate a high voltage ignition field near the implant when the implant is supported by the implant holder through the ignition electrodes. The activation device further comprises an electrical circuit 710 comprising an electric power source 714 and at least one electrode 712 electrically associated with the electric power source. The electrical circuit is configured to provide to the at least one electrode 712 electric power suitable for applying a plasma generating electric field near the implant, while preventing arcing through the electrode, when the implant is supported by the implant holder and being immersed in fluid at ambient (atmospheric) pressure.

According to some embodiments the activation device (750) further comprises a fluid transfer system 760 and a closeable chamber 720 containing the implant holder and having a fluid communication with the fluid transfer system. The fluid transfer system is associated with a fluid source 764 being thereby configured to supply to the closeable chamber an ionizable fluid suitable for plasma generation therein by the plasma-generating electric field. According to some embodiments the fluid source is a gas reservoir. According to some embodiments, one of the at least one electrodes electrically contacts the implant when the implant is supported by the implant holder.

There is further provided according to an aspect of the invention a portable container (820, 820a-820g) for handling an implant configured to be installed in a live subject. The portable container comprises a closed compartment (830, 830a-830g) containing therein the implant, the closed compartment being configured to be opened by a user, thereby enabling removing the implant from the portable container. The portable container further comprises a field transponder (854, 854a-854g) configured to transmit a signal, the signal being configured to certify an identity of the portable container or a position thereof relative to a receiver (852, 852a-852g) configured to receive the signal. The portable container is further configured to enable plasma excitation of an ionizable fluid near the implant inside the closed compartment when the ionizable fluid is subject to a plasma-generating electric field generated by an activation device (810, 810a-810g) detachable from the portable container.

According to some embodiments the field transponder is selected from the group consisting of a magnet, a mirror, a light source, an optical filter, a code sticker, a RFID chip, and a contact identification chip. According to some embodiments the field transponder is electromagnetically shielded to prevent interference of the plasma-generating filed in an operation thereof.

According to some embodiments the portable container (820a) further comprises at least one electrode (860a) made of an electrical conductive material, electrically associated with an electric conductor (862a, 862b) outside the closed compartment, and configured for applying a plasma-generating electric field inside the closed compartment.

According to some embodiments the field transponder (854*d*) is active. According to some embodiments the portable container further comprises a battery for energizing the field transponder.

According to some embodiments the closed compartment (830, 830*a*-830*g*) is sealed, enclosing an ionizable fluid of a pre-defined composition. The portable container is thereby configured to enable storing the implant inside the sealed compartment, shipping the portable container with the implant being stored therein, and, without compromising the sealing of the closed compartment, generating plasma in the fluid using an electric field, thereby surface-treating the implant.

According to some embodiments the closed compartment (830, 830*a*-830*g*) is encapsulated within a closed external capsule (610). According to some embodiments the portable container further comprises at least one floating electrode (660) disposed inside the closed external capsule being thereby electrically isolated from any conductor outside the closed external capsule, and shaped to envelope or encircle the closed compartment.

According to some embodiments the portable container further comprises at least one ignition electrode protruding into the closed compartment (similarly to ignition electrodes 1032 in compartment 1010 of container 1000) and configured to generate an ignition field inside the closed compartment when being supplied with a high voltage ignition pulse at a voltage above 5 KV.

There is further provided according to an aspect of the invention a plasma chamber (1000) for plasma treating an implant made of an electrically isolating material prior to implanting the implant in a live subject. The plasma chamber comprises a closable compartment (1010) having walls (1012, 1014) defining an internal space (1060) adapted to house the implant therein. The plasma chamber further comprises a spacer (1080) projecting from a floor (1082) of the compartment and configured to support the implant above the floor while contacting the implant along a surface area smaller than about 5% of a total surface area of the implant. The plasma chamber further comprises at least two electrodes (1020) positioned on the walls facing one another across the internal space (1060) of the closable compartment. Each electrode has a tip (1096) positioned in a hollow cavity (1094) depressed in the wall on an internal side thereof (namely the side that faces the internal space 1060). The electrodes are configured to electrically associate with an EM power source to generate a plasma generating EM field inside the closable compartment.

According to some embodiments the implant is a polymer mesh such as a hernia mesh. According to some embodiments the implant is a breast implant and the internal space (1060) is shaped as a dome.

According to some embodiments the tip 1096 is pointed. According to some embodiments the tip is blunt. A pointed tip enhances the field generated by the voltage supplied to the electrode; however a pointed tip may pose some risk of protruding beyond the cavity 1094, contacting the implant or puncturing a breast implant.

According to some embodiments the plasma chamber further comprises a liquid port 1042, configured to prevent spontaneous entering of foreign substances into the closable compartment when closed, and to enable introduction of a liquid into the closable compartment, for rinsing the implant, when open. According to some embodiments the liquid port is closed by a seal, the seal being configured to be irreversibly broken for opening the liquid port.

According to some embodiments the plasma chamber further comprises a gas port 1040, configured to enable flushing the closable compartment with a gas from a gas source external to the compartment, or pumping gas from the closable compartment.

According to some embodiments the electrodes comprise a multitude of electrodes (1020) dispersed on the walls of the compartment.

According to some embodiments the plasma chamber further comprises a high-voltage power source (1100, 1200, 1230) configured to electrically associate with the electrodes and to supply the electrodes with electric power suitable for generating a plasma-generating electric field. According to some embodiments the high-voltage power source (1100, 1200, 1230) is configured to sequentially distribute the supply of electric power between the electrodes.

According to some embodiments the plasma chamber further comprises at least one ignition electrode (1032*a*, 1032*b*) protruding into the internal space (1060) of the closable compartment (1010) and configured to generate an ignition field inside the closeable compartment when being supplied with a high voltage ignition pulse at a voltage above 5 KV. According to some embodiments the plasma chamber further comprises a high voltage pulse generator 1250 configured to generate a high voltage ignition pulse above 5 KV and electrically associated with the at least one ignition electrode. According to some embodiments the high voltage pulse generator 1250 is configured to generate a high voltage ignition pulse above 10 KV or above 20 KV or above 50 KV or even above 100 KV.

There is further provided according to an aspect of the invention a method for preparing a silicone implant to implanting the implant in a live subject. The method comprises a step of generating plasma in a plasma chamber housing the implant. The method further comprises a step of wetting the implant with a polar liquid comprising at least one therapeutically effective agent after the step of generating plasma. The method further comprises a step of removing the implant from the plasma chamber, after the step of generating plasma, for installing the implant in the live subject.

According to some embodiments the wetting is performed prior to the removing of the implant from the plasma chamber. According to some embodiments the removing of the implant from the plasma chamber is performed prior to the wetting.

According to some embodiments the polar liquid is water. According to some embodiments the water comprising a therapeutically effective agent, is an aqueous solution.

According to some embodiments the at least one therapeutically effective agent is selected from the group consisting of antimicrobial agents, anesthetics, analgesics, anti-inflammatory agents, anti-scarring agents, anti-fibrotic agents, anti-cancer compounds, hemostatic material for controlling bleeding, hormone therapeutics, stem cells, and cellular precursors. According to some embodiments the at least one therapeutically effective agent is an antimicrobial agent selected from the group consisting of antibiotics, antiseptics, and disinfectants. According to some embodiments the at least one therapeutically effective agent is an antibiotics selected from the group consisting of cefamizine, ghentamicin vancomicine, rifampin, minocycline and cloxacillin.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A method for preparing a silicone implant for implantation into in a live subject, the method comprising:
    generating plasma in a plasma chamber housing the implant;
    after said generating plasma and prior to removing the implant from the plasma chamber, wetting the implant with a polar liquid; and
    after said wetting, removing the implant from the plasma chamber, for installing the implant in the live subject.

2. The method of claim 1 wherein said polar liquid includes at least one therapeutically effective agent.

3. The method of claim 2 wherein said polar liquid is water.

4. The method of claim 2 wherein said at least one therapeutically effective agent is selected from the group consisting of antimicrobial agents, anesthetics, analgesics, anti-inflammatory agents, anti-scarring agents, anti-fibrotic agents, anti- cancer compounds, hemostatic material for controlling bleeding, hormone therapeutics, stem cells, and cellular precursors.

5. The method of claim 1, further comprising evacuating the plasma chamber prior to said generating plasma.

6. The method of claim 1, further comprising flushing the plasma chamber with an inert gas during said plasma generation.

7. The method of claim 1 wherein the implant includes a breast implant.

8. The method of claim 7 wherein plasma is generated by a plasma-generating EM field applied by pairs of electrodes, the pairs of electrodes being supplied with electric power sequentially.

9. A method for preparing a silicone implant for implantation into a live subject, the method comprising:
    generating plasma in a plasma chamber housing the implant without introducing coating material into the plasma chamber;
    after said generating plasma, wetting the implant with a polar liquid; and
    after said generating plasma, removing the implant from the plasma chamber, for installing the implant in the live subject.

10. The method of claim 9 wherein said polar liquid comprises at least one therapeutically effective agent.

11. The method of claim 10 wherein said at least one therapeutically effective agent includes at least one of antimicrobial agents, anesthetics, analgesics, anti-inflammatory agents, anti-scarring agents, anti-fibrotic agents, anti-cancer compounds, hemostatic material for controlling bleeding, hormone therapeutics, stem cells, or cellular precursors.

12. The method of claim 9 wherein said wetting is performed prior to said removing the implant from the plasma chamber.

13. The method of claim 9 wherein said removing the implant from the plasma chamber is performed prior to said wetting.

14. The method of claim 9 wherein the implant includes a breast implant.

15. A method for preparing a silicone implant for implantation into a live subject, the method comprising:
    in a plasma chamber housing the implant, generating plasma in a space adjoining the implant, thereby increasing the implant's surface tension to 0.072 N/m or more;
    after said generating plasma, wetting the implant with a polar liquid; and
    after said generating plasma, removing the implant from the plasma chamber, for installing the implant in the live subject.

16. The method of claim 15 wherein said wetting is performed prior to said removing the implant from the plasma chamber.

17. The method of claim 15 wherein said removing the implant from the plasma chamber is performed prior to said wetting.

18. The method of claim 15 wherein said polar liquid is water.

19. The method of claim 15 further comprising flushing the plasma chamber with an inert gas during said plasma generation.

20. The method of claim 15 wherein the implant includes a breast implant.

* * * * *